(12) United States Patent
Fabijanski et al.

(10) Patent No.: US 7,112,721 B2
(45) Date of Patent: Sep. 26, 2006

(54) METHODS AND CONSTRUCTS FOR PLANT TRANSFORMATION

(75) Inventors: Steven F. Fabijanski, Ottawa (CA); Laurian Robert, Gatineau (CA); Johann Schernthaner, Orleans (CA); Tong Wu, Gatineau (CA)

(73) Assignee: Sakata Seed Corporation, Yokohama (JP)

( * ) Notice: Subject to any disclaimer, the term of this patent is extended or adjusted under 35 U.S.C. 154(b) by 492 days.

(21) Appl. No.: 10/182,616

(22) PCT Filed: Feb. 7, 2001

(86) PCT No.: PCT/CA01/00136

§ 371 (c)(1), (2), (4) Date: Nov. 20, 2002

(87) PCT Pub. No.: WO01/59086

PCT Pub. Date: Aug. 16, 2001

(65) Prior Publication Data

US 2003/0159184 A1    Aug. 21, 2003

Related U.S. Application Data

(60) Provisional application No. 60/181,063, filed on Feb. 8, 2000.

(51) Int. Cl.
*C12N 15/84* (2006.01)
*C12N 15/82* (2006.01)
*C12N 15/31* (2006.01)

(52) U.S. Cl. ............ 800/294; 800/288; 800/290; 800/306; 435/462; 435/469

(58) Field of Classification Search .......... 800/278, 800/288, 294, 290, 287, 306; 435/468, 469, 435/462
See application file for complete search history.

(56) References Cited

U.S. PATENT DOCUMENTS

| | | | | |
|---|---|---|---|---|
| 5,463,174 | A | * | 10/1995 | Moloney et al. ............ 800/294 |
| 5,635,381 | A | | 6/1997 | Hooykaas et al. |
| 5,658,772 | A | | 8/1997 | Odell et al. |
| 5,965,791 | A | * | 10/1999 | Ebinuma et al. ............ 800/278 |
| 6,063,985 | A | * | 5/2000 | Chua et al. ................. 800/278 |
| 6,326,192 | B1 | * | 12/2001 | Sugita et al. ............ 435/320.1 |
| 6,849,778 | B1 | * | 2/2005 | Staub et al. ................. 800/278 |

FOREIGN PATENT DOCUMENTS

EP    0716147    12/1996

OTHER PUBLICATIONS

Zhang et al. Theoretical and Applied Genetics 107(7): 1157-1168 (Nov. 2003).*
Ebinuma et al. pp. 25-46 In: Molecular Biology of Woody Plants, vol. 2, Jain et al, eds., Kluwer Academic Publishers: Dordrecht, The Netherlands (2000).*
Ebinuma et al. pp. 95-117 In: Molecular Methods of Plant Analysis, vol. 22, Jackson et al, eds., Springer-Verlag: Berlin (2002).*
Ebinuma et al. In Vitro Cellular Development and Blology—Plants 37(2): 103-113 (Mar.-Apr. 2001).*
Hiroyasu Ebinuma et al., Selection of marker-free transgenic plants using the isopentenyl transferase gene, Proc. Natl. Acad. Sci. USA, vol. 94, pp. 2117-2121, Mar. 1997, Applied Biological Sciences.
Alan M. Lloyd et al., Functional expression of the yeast FLP/FRT site-specific recombination system in *Nicotiana tabacum*, Mol. Gen Genet. (1994) 242:653-657.
John I. Yoder et al., Transformation Systems for Generating Marker-Free Transgenic Plants, Bio Technology vol. 12 Mar. 1994 pp. 263-267.
Emily C. Dale et al., Gene transfer with subsequent removal of the selection gene from the host genome, Proc. Natl. Acad. Sci. USA, vol. 88, pp. 10558-10562, Dec. 1991, Applied Biological Sciences.
Andrew P. Gleave et al., Selectable marker-free transgenic plants without sexual corssing: transient expression of *cre* recombinase and use of a conditional lethal dominant gene, Plant olecular Biology 40: 223-235, 1999.
Koichi Sugita et al., A transformation vector for the production of marker-free transgenic plants containing a single copy transgene at high frequency, The Plant Journal (2000) 22(5), 461-469.
Dudkowska, M., et al., "Cross-talk between steroid-receptor-mediated and cell-membrane-receptor-mediated signally pathways results in the *in vivo* modulation of c-Met and ornithine decarboxylase gene expression in mouse kidney", Biochem. J. (2001) vol. 353, p. 317-323.
Fukuda, R., "The expression of RNA polymerase genes carried by composite plasmids in *Escherichia coli*", Annual Report of the Institute for Virus Research, Kyoto University (1978) vol. 21, p. 27-32, Abstract Only (Accession No. 91:35553).

* cited by examiner

*Primary Examiner*—David T. Fox
(74) *Attorney, Agent, or Firm*—Bacon & Thomas, PLLC

(57) ABSTRACT

The present invention relates to novel methods for the transformation of crop species, novel methods for the selection and identification of transformed plant cells and novel methods for recovery of regenerated whole plants. The method also relates to the development of plants with novel traits and plants that contain novel recombinant DNA constructs.

11 Claims, 33 Drawing Sheets pRBC-1

METHODS AND CONSTRUCTS FOR PLANT TRANSFORMATION

CROSS-REFERENCE TO RELATED APPLICATIONS

The present application claims the benefit of U.S. Provisional Patent Application Ser. No. 60/181,063, filed Feb. 8, 2000, which is incorporated herein by reference in its entirety.

FIELD OF THE INVENTION

The present invention relates to novel methods for the transformation of plant species and methods to produce transgenic plant species free of selectable marker genes. The present invention also relates to novel *Agrobacterium* vectors and uses thereof.

BACKGROUND OF THE INVENTION

The development of transgenic crops requires methods for the stable insertion of recombinant DNA, a process typically referred to as transformation. Transformed plant cells are generated by the use of a variety of methods to insert foreign DNA into plant cells. These methods further employ the use of genetic constructs which contain genes encoding resistance to chemical selection agents such as antibiotics (e.g. kanamycin or hygromycin) or herbicides. Plant cells expressing selectable markers are preferentially obtained by culturing a population of plant cells subjected to a transformation process in the presence of media which contains, in addition to the selective agent, specific combinations of phytohormones and nutrients to allow cells to grow and regenerate to intact plants. Thus, the process of producing a transformed cell requires a means to physically insert foreign DNA as well as a means to select for those cells which have incorporated the DNA in an expressible and stable form.

Following the stable insertion and expression of the foreign DNA, regeneration of cells containing the foreign DNA leads to the recovery of whole plants, usually following shoot-, embryo- or organo-genesis. The regenerated plant tissue is induced, by a number of different means, typically by the alteration of tissue culture conditions, more typically by manipulation of phytohormones, to form a whole plant capable of forming seed and/or pollen, which can transfer the foreign DNA to subsequent generations. In some plant species, a major limitation is efficient selection and regeneration of plant cells following transfer of DNA, as opposed to the actual transfer of DNA into the cell. Thus, practical limitations on the use of standard transformation methods generally relate to the efficiency of selection and identification of transformed plant cells, not necessarily the transfer of DNA into the plant cell. Another step in the process that is often problematic is the regeneration of transformed cells into whole plants in the presence of a selective agent.

One potential problem related to the selection of plant cells is the effect of the selective agent on non-transformed cells, i.e. plant cells that do not contain the selectable marker. Often the selection process kills the majority of non-transformed cells, a process that, for a variety of physiological reasons, often reduces the efficiency or frequency of regeneration of transformed cells. Thus, the selective pressure needed to identify the cells containing the foreign DNA often proves to be an inhibitory factor to the efficient regeneration of plant cells.

Thus, methods that allow for the selection of plant cells without a direct lethal effect on the non-transformed cells may provide a means to reliably recover transformed plant cells. In addition, regeneration may prove to be more efficient, especially in those plant species, varieties or cells that are difficult to transform by means conventionally practiced. This problem is a major limitation for the routine and economical production of transformed plants.

It is believed that transformation of plant tissue results in only a small percentage of the total number of cells subjected to the transformation process actually incorporating the DNA into their nuclear DNA. Upon application of the selective agent, most plant cells die and may release substances (such as ethylene or senescence related compounds) that affect other nearby cells, including those containing the selectable marker gene and thus prevent efficient regeneration of these transformed cells. It appears that the death of the non-transformed cells may release substances inhibitory to the survival of the transformed cells. Accordingly a primary limitation for efficient production of transformed plants is the recovery of transformed plant cells and subsequent regeneration to whole plants. Methods which permit the rapid and efficient recovery of plant cells containing foreign DNA under conditions where the selection process does not lead to the death of non-transformed cells, (with subsequent inhibition of regeneration) would provide a convenient and efficient means to recover plants, particularly in those plant species where transformation has proven to be costly and time-consuming. Many plant species are capable of being transformed by introduced DNA, however the efficiency of the regeneration process is exceedingly low and prohibits the development of transgenic crops. Furthermore, the significant variation in tissue culture response or regeneration potential in tissue culture found within species, subspecies or varieties within a specific crop genus severely restricts the effective range of current transformation processes.

*Brassica* species are of special interest. Transformation of members of the Cruciferae family by *Agrobacterium* and other methods has been reported. A significant body of scientific work has accumulated that describes various methodologies, techniques and studies related to the generation of transgenic *Brassica* plants that contain foreign DNA of commercial interest and utility. A significant effort to achieve this was made through the early 1980's and still is being made. The technology has been advanced to the point where transformation is now routine for certain narrow genotypes of a species within the *Brassicacea,* however, it remains difficult within other species in the same family. In addition there is a strong influence of genotype on transformation success within those *Brassicas* that have been successfully transformed and technology that is more widely applicable to even the "recalcitrant" genotypes would be of great value to the industry. While there are many transgenic *Brassica* undergoing field evaluation, analysis of the field trial data clearly indicates that the majority (>95%) of the transgenic *Brassica* are *B. napus* types, much of the material has been derived from a narrow range of germplasm within *B. napus*. Part of the reason for this has been the difficulty of routinely obtaining transformed *B. rapa* and *oleracea* types as well as the fact that the development of commercial transgenic plants is still relatively recent.

However, many of the reports that relate specifically to *Brassica* transformation have detailed the difficulty in routinely obtaining transformed *Brassica* species by *Agrobacterium* mediated transformation. Many of the reports have shown success with one or two particular varieties, but there is no teaching of detailed methods that are generally applicable to all species within the *Brassica* genus. Although many manipulations of culture conditions can be employed, some varieties have proven to be extremely difficult to transform by previously reported methods.

Many of the initial *Brassica* transformation studies were carried out with *B. napus* cv Westar (Radke et al, *Theor. Appl. Genet.* 75:685–694, 1988; Moloney et al., *Plant Cell Reports* 8:238–242, 1989; Moloney et al., 1989, U.S. Pat. No. 5,188,958; Moloney et al., 1989, U.S. Pat. No. 5,463,174). Westar was a convenient choice since it responded to tissue culture and transformation protocols described in the references cited above and allowed recovery of transgenic plants. However; many *Brassica* transformation studies conducted using the described methods, or variations thereof, have produced results that are highly variable and are dependent upon the innate response of the specific plant materials to the transformation protocol. As an example, the transformation frequencies that have been achieved for *Brassica napus* are sometimes variable and very low (Fry et al., *Plant Cell Reports* 6:321–325, 1987; Mehra-Palta et al., *In Proc 8th Int. Rapeseed Congress,* Saskatoon, Saskatchewan, 1991; Swanson and Erickson, *Theor. Appl. Genet.* 78:831–835, 1989). Variable and often low transformation frequencies have also been observed with other *Brassica* species, such as *B. oleracea* (Christie and Earle, *In Proc 5th Crucifer Genetics Workshop,* Davis, pp 46–47, 1989; Metz et al., *Plant Cell Reports* 15: 287–292, 1995; Eimert and Siegemund, *Plant Molec. Biol.* 19:485–490, 1992; DeBlock et al., *Plant Physiol.* 91:694–701, 1989; Berthomieu and Jouanin, *Plant Cell Reports* 11:334–338; Toriyama et al, *Theor. Appl. Genet.* 81:769–776, 1991); *B. rapa* (Radke et al., *Plant Cell Reports* 11:499–505, 1992; Mukhopadhyay et al, *Plant Cell Reports* 11:506–513, 1992); *B. juncea* (Barfield and Pua, *Plant Cell Reports* 10:308–314, 1991; Deepak et al., *Plant Cell Reports* 12:462–467, 1993; Pua and Lee, *Planta* 196:69–76, 1995); *B. nigra* (Gupta et al, *Plant Cell Reports* 12:418–421, 1993); and *B. carinata* (Narasimhulu et al., *Plant Cell Reports* 11:359–362, 1992; Babic, M.Sc. Thesis, Univ of Saskatchewan, 1994).

The many *Brassica* species, varieties and cultivars represent a very diverse group with radically different morphologies and physiological characteristics. In addition to oilseed *Brassica,* the vegetable *Brassicas* represent a crop with significant economic value. This value could be enhanced by the addition of certain novel traits such as disease and insect resistance, male sterility systems for hybrid seed production, certain quality traits, and the like. Accordingly efficient transformation systems for broccoli, cabbage, cauliflower, kale and other *Brassica* vegetables would be valuable. Many *Brassica* vegetable species of commercial interest do not respond well or at all to the methods previously described. A transformation method is required which is useful for substantially all of the *Brassica* species and especially those previously recalcitrant to transformation.

In addition to obstacles encountered within the genus *Brassica,* other plant genera have exhibited similar phenomena. Many commercially important plant species or genera are difficult to transform and typically only a narrow range of specific genotype is amenable to transformation. This includes crops such as cotton, soybean, sunflower, cereal crops such as wheat, barley, rice and corn as well as many ornamental and vegetable crops. Often, a wide range of genotypes are amenable to culture and regeneration, but the combination of the selection and transformation process eliminates efficient regeneration and hence leads to extremely inefficient transformation of elite lines. Thus most transformation processes are conducted with a narrow germplasm, followed by characterization of the line and extensive backcrossing. Many transgenic crop varieties produced to date have been made by transformation of a specific variety that has been demonstrated as being amenable to transformation followed by extensive crossing to those varieties most suitable for widespread cultivation. This trait introgression is time-consuming and expensive.

Accordingly, methods that permit the efficient transformation of a wide range of crop species and individual varieties, are essentially genotype independent and capable of being used to impart a variety of novel traits will be of significant benefit to the industry. Furthermore, methods that avoid, as a primary step in the process, the use of a toxic selective agent which kills non-transformed cells, may provide opportunities to achieve the efficient regeneration of plants in species where this has been found to be difficult or in those plant varieties where this is currently not possible.

It has been noted that one of the most efficient transformation processes is the natural infectivity process of *Agrobacterium* species. *Agrobacterium* is a free-living Gram-negative soil bacterium. Virulent strains of this bacterium are able to infect plant tissue and induce the production of a neoplastic growth commonly referred to as a crown gall. Virulent strains of *Agrobacterium* contain a large plasmid DNA known as a Ti-plasmid that contains genes required for plasmid transfer and replication as well as a region of DNA that is called T-DNA. The T-DNA region is bordered by T-DNA border sequences that are crucial to the DNA transfer process. These T-DNA border sequences are recognized by the vir genes encoded on the Ti-plasmid and the vir genes are responsible for the DNA transfer process. Thus the native Ti-Plasmid contains the vir genes as well as the T-DNA region and the T-DNA borders required for efficient DNA transfer to a recipient plant cell. The entire complement of these genetic elements, in conjunction with genes encoded on the bacterial chromosome allow the efficient transfer of the T-DNA region into plant cells with subsequent stable integration and expression of the various genes encoded by the T-DNA.

The T-DNA transferred and integrated into the plant cell nucleus contains a number of genes that encode enzymes for the production of unusual amino acids (opines) and genes that encode enzymes capable of producing plant hormones and genes responsible for the modulation of plant development. As such, there are a relatively large number of genes within the T-DNA that are transferred to the plant cell, the function of all of genes has not been completely elucidated in the *Agrobacterium* genus. However, the primary effect of the genes in the T-DNA are at the level of plant cell growth and development. Following infection by *Agrobacterium,* the plant cells infected with the T-DNA undergo an uncontrolled proliferation due to the activity of the T-DNA genes. These genes, referred to as "oncogenes" because of the phenotype they confer, permit hormone-independent growth of transformed cells in culture. The expression of these various oncogenes causes the formation of gall callus, callus that is not capable of regeneration to differentiated complex plant structures such as fertile shoots, or whole plants.

The process of gall or tumor formation is very efficient, essentially 100% of inoculated *Agrobacterium* susceptible plant tissue will form a tumor. Thus the natural *Agrobacterium* DNA transfer process is exceedingly efficient. In addition, the physiological processes of crown gall formation are also very efficient in conferring a transformed phenotype. Furthermore, most wild-type *Agrobacterium* have broad host range and are capable of transferring large segments of DNA, typically T-DNA transferred to plant cells contains up to 25 kilobases of DNA (e.g. nopaline strains) or more (e.g. octopine strains). Thus the naturally occurring DNA transfer system of *Agrobacterium* provides an efficient means to transfer DNA into a plant cell and the subsequent formation and identification of transformed tissue.

Accordingly, numerous methods of using *Agrobacterium* to transfer DNA into plant cells have been developed. Typically these have been based on the engineering of the Ti-plasmid to no longer contain the genes responsible for altered morphology ("oncogenes") and replacing these genes with a recombinant gene encoding a trait of interest. Linked to this trait of interest is a gene encoding a selectable marker such that cells that receive the DNA can be selected. Usually the vir genes are left intact, however some methods include the alteration of the vir genes in one form or another.

There are two primary types of *Agrobacterium* based plant transformation systems, binary and co-integrate methods. The use of the binary transformation system is described by Schilperoort et al in U.S. Pat. No. 4,940,838. An example of the co-integrate system is found in Fraley et al., Biotechnology, 3:629–635, 1985. Both the co-integrate and binary systems are based on replacing the normally oncogenic complement of *Agrobacterium* genes with engineered, non-oncogenic DNA, typically DNA that comprises a selectable marker and a gene encoding a novel trait. The T-DNA border repeats are maintained in both systems and the natural DNA transfer process is used to transfer the portion of DNA located between the T-DNA borders into the plant cell. Thus, these transformation methods avoid the problems associated with recovery of morphologically normal plant cells when using methods wherein the oncogenic region of the Ti-plasmid is inserted into a plant cell. Therefore, these methods rely on the presence of a selectable marker to recovery transformed cells since the selection based on the activity of the oncogenes can no longer be used.

It has been recognized that the presence of oncogenes within the DNA transferred to plant cells prevents the regeneration of morphologically normal plants. It has also been recognized that each of the various oncogenes encoded by the T-DNA has a different role and the total activity of the various oncogenes leads to crown gall formation. Independently each of the primary oncogenes has a defined function and typically the presence of only one or two functional oncogenes leads to the formation of morphologically abnormal plants. This is in contrast to the crown galls produced by the activity of all of the oncogenes, crown galls (or callus derived from crown gall tissue) cannot regenerate or form morphologically normal plants. Indeed, crown gall tissue is not capable of regeneration to differentiated plant tissue. Accordingly crown gall tissue has been considered to represent a terminal tissue in the *Agrobacterium* infectious process. Thus it has been recognized in the art that the full complement of oncogenes contained within the T-DNA eliminates the potential for recovery of morphologically normal plants.

However, it has been shown in the art that one or two oncogenes can be included in a transformation vector for plants and the activity of these oncogenes used as a method to screen for transformed cells. For example, Ebunuma et al., (Proc. Natl. Acad. Sci. USA 94:2117–2121, 1997, U.S. Pat. No. 5,965,791) describe a plant transformation vector that comprises the isopentyl transferase gene from *Agrobacterium* (typically referred to as oncogene 4) as a means to identify transformed plant cells. In this method, the activity of the oncogene causes the production of cytokinin, a plant hormone that causes shoot production. In this case, a "shooty" mutant is produced (a morphologically abnormal shoot) and the plant cells are selected on the basis of abnormal shoot formation as well as selection for resistance to kanamycin or herbicides. As an added feature of the method, the oncogene is bordered by transposition elements that permit the eventual loss of the oncogene from the transformed plant cell. The arrangement of DNA in the vector is such that the gene of interest remains in the transformed plant cell.

Although this method relies on the activity of oncogene 4 to discriminate transformed versus non-transformed cells, the method requires visual discrimination of regenerating plant shoots, can lead to the formation of chimaeric plants and requires various tissue culture manipulations to recover single cell derived transgenic plants.

Indeed the method described in U.S. Pat. No. 5,965,791 relies on the regeneration of morphologically abnormal plant structures as a marker for transformation. The morphological abnormality induction gene causes the formation of abnormal plant structures, and in many cases somaclonal and culture variation lead to the same phenotypic effect, thus further analysis is required to fully obtain transgenic plants. Thus the method has limitations and may not provide a convenient means to transform recalcitrant plant species or varieties. The method still relies on the use of a dis-armed *Agrobacterium* strain and the efficiency of transformation is correspondingly reduced relative to the natural formation of crown galls.

Similarly, it has been shown that the oncogene 2 can be used for discrimination of transformed plant cells, and recovery of transgenic plants following regeneration and selection of transgenic cells on appropriate media or under appropriate selective conditions. Keller et al., (International Publication No. WO 00/37060) demonstrates that the isolated oncogene 2 can be used for discrimination of transgenic plant cells following transformation and culturing on selective media. Abnormal plantlets are produced in the presence of the oncogene 2 enzyme and an appropriate substrate for the enzyme. As above, the selection of a transformed plant relies on the formation of a morphologically abnormal structure.

In both of these examples, the usual transfer process of DNA from *Agrobacterium* to a plant cell occurs as a result of the modification of a plant transformation vector to comprise a binary vector system and a dis-armed T-DNA region. These modifications have typically included the elimination of most if not all of the natural sequences found within the T-DNA, including many open reading frames and genes whose function is not well understood but likely to play an important role in the efficiency of the transfer and integration process. These oncogenes utilized are modified and outside of the normal environment that characterizes their naturally occurring roles in the formation of crown gall tissue.

However, the natural T-DNA transfer process and subsequent formation of crown galls or plant tumors with wild-type T-DNA is a highly efficient process. The process is usually very efficient even on plant varieties and species that are recalcitrant to usual tissue-culture protocols for the introduction of DNA by *Agrobacterium* and recovery of transgenic plants (for example various *Brassica* species or cotton). In most instances crown galls will form easily on decapitated plants or wounded stems, even on plant genotypes recalcitrant to transformation using typical dis-armed vectors. Crown gall formation is also easily scored and true galls (i.e., those carrying the entire T-DNA region) are not capable of forming any differentiated plant tissue. Although spontaneous shoots or roots can form with some *Agrobacterium* strains, usually crown galls do not form differentiated cells, even morphologically abnormal differentiated cells unless one or more of the encoded oncogenes undergoes a mutation or loss of function. Crown galls can also be easily cultured by simple growth on hormone free minimal media. Crown galls can also be made bacteria free by culturing in antibiotic solution for a period of time. Thus it is a trivial process to obtain bacteria-free, transformed plant cells from many different plant species comprising intact oncogenic T-DNA.

Thus, a method for plant transformation that could take advantage of this efficient process, along with the easy means of identifying the transformed cells (by hormone-independent growth in culture) can provide many advantages including efficiency of transformation and selection of transformed plant cells. However, the art teaches that when the naturally occurring oncogenic region is used, recovery of morphologically normal plant cells is not possible. Thus, methods for recovering morphologically normal plant cells following the formation of crown galls are not available and hence the efficiency and wide host range of the natural T-DNA transfer process cannot be used as a means to produce morphologically normal transformed plants from a wide range of plant species.

SUMMARY OF THE INVENTION

The present invention provides a novel method to produce and recover transformed plants that are morphologically normal and free of selectable markers. The invention utilizes the efficient and convenient process of T-DNA transfer as found in wild-type *Agrobacterium* to produce plant cells capable of growth under-hormone free conditions, leading to the formation of cells that can be conveniently identified by visual characteristics and under simple culture conditions. The plant cells are then selected from non-transformed cells and induced to regenerate into whole plants.

The methods of the invention can avoid the antibiotic or herbicide selection of plant cells and offers an efficient means to recover transformed plants, particularly with those plant species that are difficult to transform by standard *Agrobacterium* and selection techniques.

The broad method of the present invention utilizes transformation of plant cells with *Agrobacterium* oncogenes to produce a population of cells that contain oncogenes and are able to grow under conditions insufficent for the growth of untransformed cells, such as conditions lacking plant growth hormones. This results in the selection of transformed cells. Preferably, the cells are transformed with the full complement of oncogenes found in wildtype *Agrobacterium* T-DNA.

Although the transformed cells can grow under conditions insufficient for the growth of untransformed cells, the presence of the oncogenes usually prevents the transformed cells from regenerating to form morphologically normal plants. Therefore, the transformed cells are then further modified to eliminate oncogene function, thus restoring the ability to regenerate and grow normally, so that a morphologically normal plant can be recovered. Hence, in a broad aspect, the invention provides a method for preparing a transformed plant, comprising:

(a) introducing into plant cells a construct comprising at least one *Agrobacterium* oncogene to obtain transformed cells comprising the construct, the expression of the *Agrobacterium* oncogene in the transformed cells enabling the cells to grow under conditions insufficient for the growth of untransformed cells, whereby transformed cells are selected; and (b) negating the effect of the at least one *Agrobacterium* oncogene in the transformed cells and regenerating a morphologically normal transformed plant from the transformed cells.

In one aspect, the construct comprises, in the 5' to 3' direction, a first recombinase recognition site, at least one *Agrobacterium* oncogene, and a second recombinase recognition site. The negating step then comprises excising the *Agrobacterium* oncogene(s) or a portion thereof from the construct with a recombinase which recognizes the first and second recombinase recognition sites. The recombinase may be encoded by a recombinase coding sequence contained in the original construct containing the oncogene, or it may be introduced into the transformed plant cells in a second construct. The recombinase coding sequence may be under the control of an inducible promoter, and it may contain a plant intron.

Preferably, either the construct containing the oncogene or the second construct includes a novel trait coding sequence which, when expressed in a plant, confers a novel trait on the plant. When the novel trait coding sequence is contained in the construct containing the *Agrobacterium* oncogene or oncogenes, the ability of the transformed cells to grow under conditions under which untransformed cells cannot grow (e.g. in the absence of plant growth hormones), results in selection of the cells transformed with the novel trait coding sequence when the cells are grown without plant growth hormones, or with levels of hormones insufficient for the growth of untransformed cells. The use of an additional selectable marker is therefore not required.

In a particularly preferred method, the construct carrying the oncogene is a modified *Agrobacterium* T-DNA region comprising, in the 5' to 3' direction, a right T-DNA border sequence, a first recombinase recognition site, at least one oncogene, a second recombinase recognition site, and a left T-DNA border sequence. Preferably, the construct is introduced into the plant cells by *Agrobacterium*-mediated transformation.

In another aspect, the recombinase recognition sites are replaced with transposase recognition sites, and a transposase enzyme which recognizes the transposase recognition sites is used to excise the one or more oncogenes or a portion thereof.

In yet another aspect, the negating step comprises contacting the construct containing the *Agrobacterium* oncogene with a DNA binding protein to inhibit the expression of the product encoded by the oncogene. The construct containing the *Agrobacterium* oncogene may include a DNA binding protein coding sequence which encodes the DNA binding protein, or the DNA binding protein coding sequence may be contained in a second construct introduced into the plant cells in a second transformation event.

In a further aspect, the negating step comprises contacting the *Agrobacterium* oncogene or a transcript thereof with an antisense polynucleotide which inhibits transcription of the oncogene or inhibits translation of the transcript thereof.

The use of recombinases, transposases, DNA binding proteins and antisense polynucleotides are merely some of the suitable methods for negating the effect of the *Agrobacterium* oncogenes in the transformed cells in accordance with the invention. Other methods for negating the effect of the *Agrobacterium* oncogenes will be apparent to those of skill in the art, including the use of co-suppression or ribozyme techniques.

The methods of the invention are suitable for use with monocot or dicot plants, preferably dicot plants. Preferred plants include members of the family Malvaceae, Linaceae, Compositae, Solanaceae, Fabaceae, Euphorbiaceae, Oleaceae, or Brassicaceae. Preferably, the plant is a member of the genus *Brassica*, such as, without limitation, broccoli, cabbage, cauliflower, kale, Chinese kale, collard, kohlrabi, Chinese cabbage, pak choi, or turnip.

The invention also provides plants, plant seeds, plant embryos, plant cells, or plant tissues, prepared according to the methods of the invention.

The invention also provides various vectors, constructs, and modified Ti-plasmids useful for practicing the methods of the invention.

In one aspect, the invention provides a DNA vector comprising, in the 5'-3' direction, a DNA sequence homologous to a left portion of the right border region of the T-DNA region of a Ti-plasmid, a recombinase recognition site, and a region of DNA homologous to a right portion of the right border region of the T-DNA region of a Ti-plasmid.

In another aspect, a DNA vector comprising, in the 5'-3' direction, a DNA sequence homologous to a left portion of the left border region of the T-DNA region of a Ti-plasmid, a recombinase recognition site, and a region of DNA homologous to a right portion of the left border region of the T-DNA region of a Ti-plasmid, is provided.

The DNA vector may further comprise an antibiotic resistance marker useful for selection in *Agrobacterium*.

In another aspect a modified Ti-plasmid comprising a recombinase recognition site 3' to the right T-DNA border is provided.

In yet another aspect, the invention provides a modified Ti-plasmid comprising a recombinase recognition site 5' to the left T-DNA border.

In yet another aspect, the invention provides a modified Ti-plasmid comprising a recombinase recognition site 3' to the right T-DNA border and a recombinase recognition site 5' to the left T-DNA border.

The modified Ti-plasmid may further comprise a recombinase coding sequence expressible in plant cells, and/or a scorable marker coding sequence expressible in plant cells.

Particularly preferred vectors and plasmids include: modified Ti-plasmid pTi-C58 CIMB; modified Ti-plasmid pTi-C58 TIMB; modified Ti-plasmid pTi-C58 RBC-1; DNA vector pRBC-1; DNA vector pLBC-1; and DNA vector pLBC-2, as described herein.

The invention further provides a construct for transformation of plant cells comprising, in the 5' to 3' direction, a first recombinase recognition site, at least one oncogene, and a second recombinase recognition site. The construct may further comprise a recombinase coding sequence which encodes a recombinase. Preferably, the construct further comprises a novel trait coding sequence located either 5' to the first recombinase recognition site or 3' to the second recombinase recognition site, the expression of the novel coding sequence in a plant conferring a novel trait on the plant. The recombinase coding sequence may be under the control of an inducible promoter, and may include a plant intron.

A particularly preferred construct is a modified *Agrobacterium* T-DNA region comprising, in the 5' to 3' direction, a right T-DNA border sequence, a first recombinase recognition site, at least one oncogene, a second recombinase recognition site, and a left T-DNA border sequence.

In another aspect, transposase recognition sites may be substituted for the recombinase recognition sites, and a transposase coding sequence substituted for the recombinase coding sequence.

The invention also provides a construct comprising at least one oncogene and a DNA binding protein coding sequence which encodes a DNA binding protein. Preferably, the construct further comprises a novel trait coding sequence the expression of which in a plant conferring a novel trait on the plant.

The invention also provides plants, plant seeds, plant embryos, plant cells, or plant tissues, comprising a construct or vector according to the invention.

The invention further provides an *Agrobacterium* cell, comprising a construct, vector, or a Ti-plasmid according to the invention.

The invention also provides a method for modifying a Ti-plasmid to contain recombinase or transposase recognition sites comprising:

(a) introducing a first DNA vector into *Agrobacterium* cells comprising a Ti-plasmid under conditions sufficient for a homologous recombination event to occur between the DNA vector and the Ti-plasmid, the first DNA vector comprising, in the 5'-3' direction, a DNA sequence homologous to a left portion of the right border region of the T-DNA region of said Ti-plasmid, a recombinase or transposase recognition site, and a region of DNA homologous to a right portion of the right border region of the T-DNA region of the Ti-plasmid, to obtain Agrobacterium cells comprising a modified Ti-plasmid with a recombinase or transposase recognition site within the T-DNA region and in proximity to the right T-DNA border sequence; and, (b) introducing a second DNA vector into the *Agrobacterium* cells from step (a) under conditions sufficient for a homologous recombination event to occur between the second DNA vector and the modified Ti-plasmid, the second DNA vector comprising, in the 5'-3' direction, a DNA sequence homologous to a left portion of the left border region of the T-DNA region of the modified Ti-plasmid, a recombinase or transposase recognition site, and a region of DNA homologous to a right portion of the left border region of the T-DNA region of the modified Ti-plasmid, to obtain *Agrobacterium* cells comprising a further-modified Ti-plasmid, the further-modified Ti-plasmid comprising a recombinase or transposase recognition site within the T-DNA region of and in proximity to the left T-DNA border sequence of the further-modified Ti-plasmid and a recombinase or transposase recognition site within the T-DNA region of and in proximity to the right T-DNA border sequence of the further-modified Ti-plasmid.

Preferably, the Ti-plasmid further comprises within the T-DNA region a recombinase or transpose enzyme coding sequence under the control of an inducible promoter. The Ti-plasmid may further comprise within the T-DNA region a scorable marker gene expressible in plant cells.

DETAILED DESCRIPTION OF THE INVENTION

Figure 1:
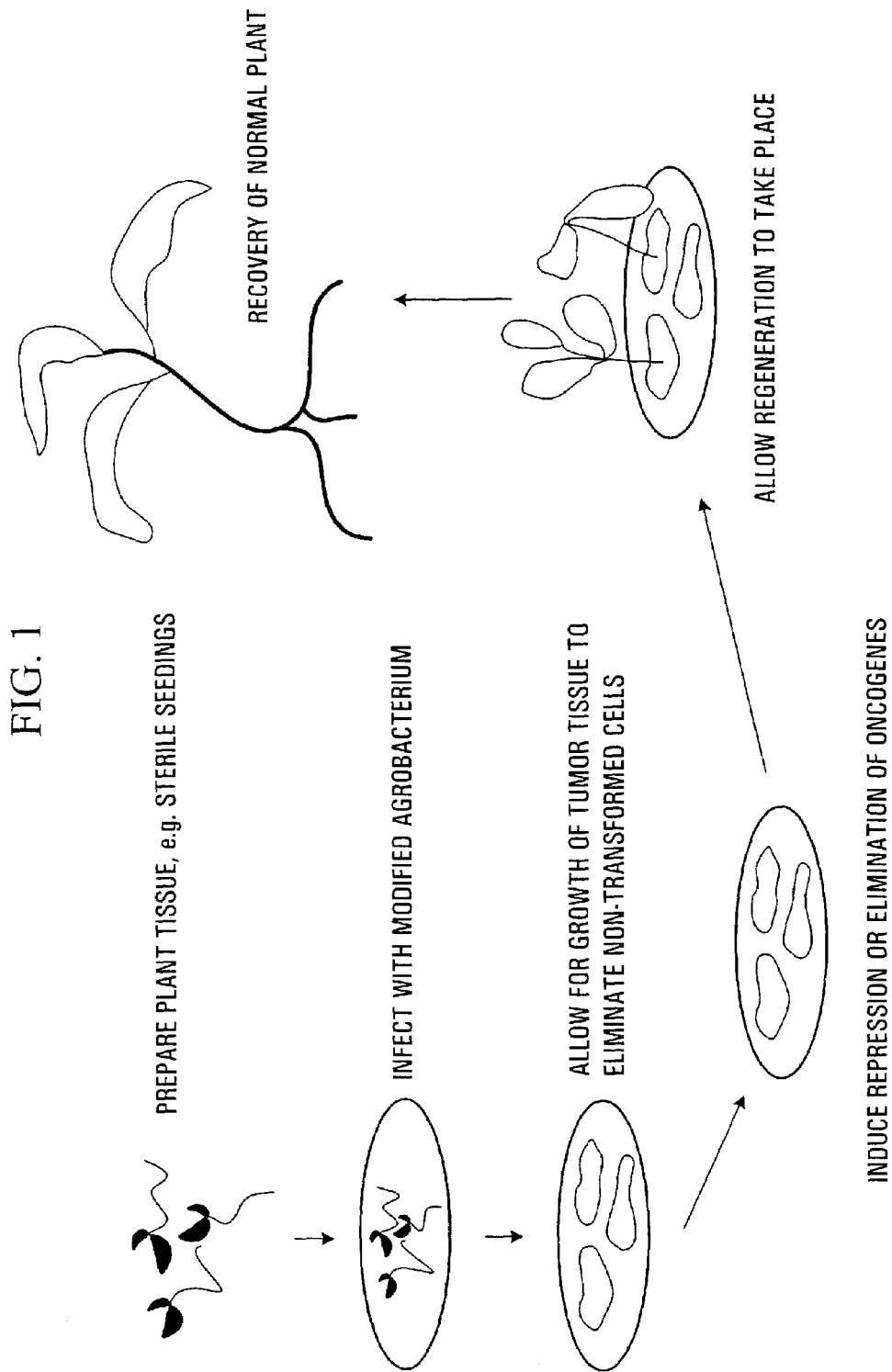
FIG. 1 illustrates a general approach to using the methods of the invention to recover transformed plant cells and whole plants.
Figure 2:
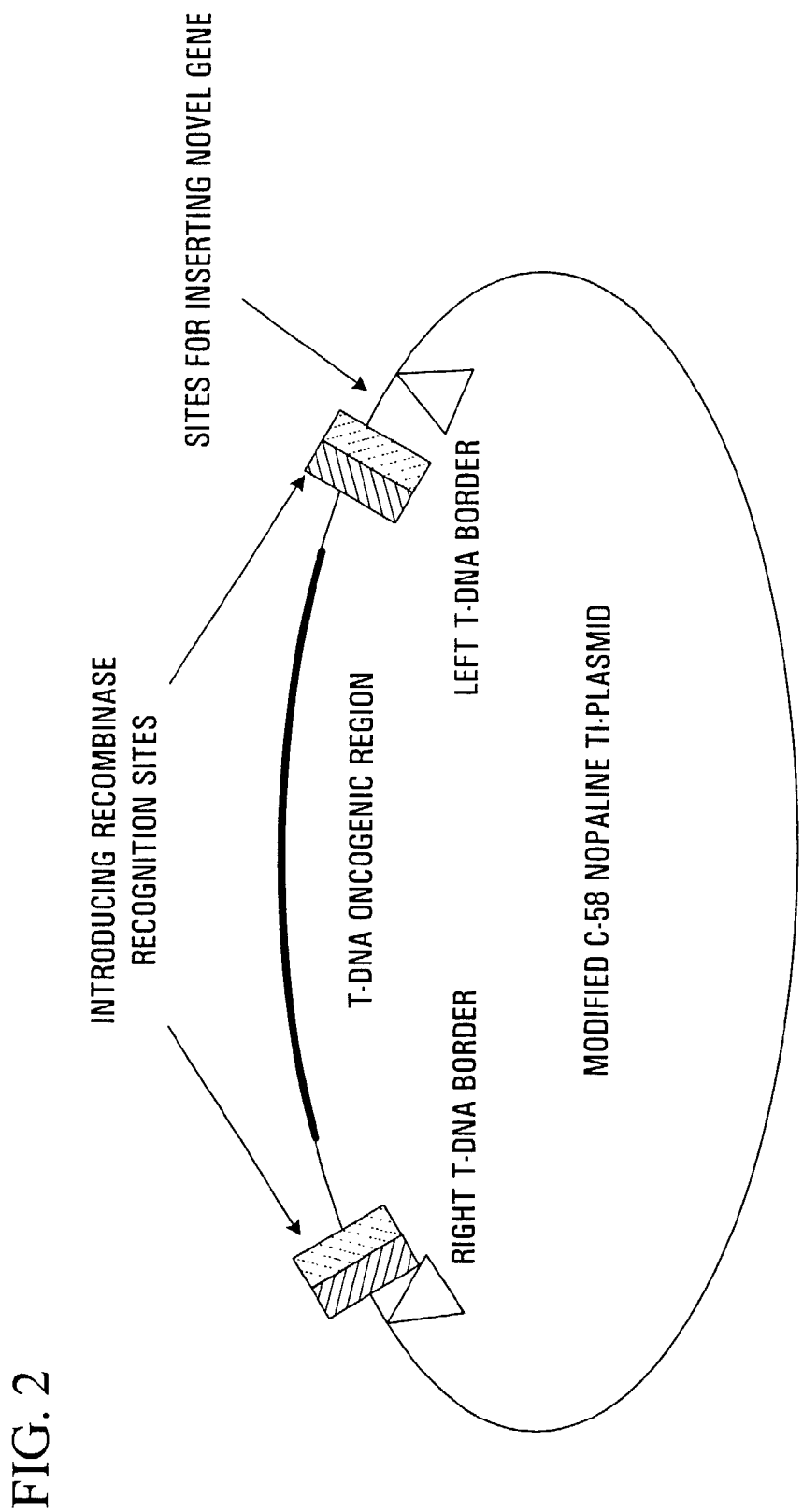
FIG. 2 illustrates the derivation of a modified Ti-plasmid comprising recombinase recognition sites.

In order to provide a clear and consistent understanding of the specification and claims, including the scope to be given certain terms used therein, the following definitions are provided.

The singular forms "a," "an," and "the" include plural reference unless the context clearly dictates otherwise.

A "coding sequence" or "coding region" is the part of a gene that codes for the amino acid sequence of a protein, or for a functional RNA such as a tRNA or rRNA.

A "complement" or "complementary sequence" is a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

"Expression" refers to the transcription of a gene into structural RNA (rRNA, tRNA) or messenger RNA (mRNA) with subsequent translation into a protein.

Polynucleotides are "functionally equivalent" if they perform substantially the same biological function.

Polynucleotides are "heterologous" to one another if they do not naturally occur together in the same arrangement in the same organism. A polynucleotide is heterologous to an organism if it does not naturally occur in its particular form and arrangement in that organism.

Polynucleotides or polypeptides have "homologous" or "identical" sequences if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a comparison window to identify and compare local regions of sequence similarity. The comparison window is generally from about 20 to about 200 contiguous nucleotides or contiguous amino acid residues. The "percentage of sequence identity" or "percentage of sequence homology" for polynucleotides and polypeptides, such as 50, 60, 70, 80, 90, 95, 98, 99 or 100 percent sequence identity may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences.

The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al. 1990. J. Mol. Biol. 215:403; Altschul, S. F. et al. 1997. Nucleic Acids Res. 25: 3389–3402) and ClustalW programs. BLAST is available on the Internet at http://www.ncbi.nlm.nih.gov and a version of ClustalW is available at http://www2.ebi.ac.uk. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

The terms "stringent conditions" or "stringent hybridization conditions" includes reference to conditions under which a probe will hybridize to its target sequence, to a detectably greater degree than other sequences (e.g. at least 2-fold over background). Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The Tm is the temperature (under defined ionic strength and pH at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. Hybridization procedures are well-known in the art and are described in Ausubel et al., (Ausubel et al., Current Protocols in Molecular Biology, John Wiley & Sons Inc., 1994).

"Isolated" refers to material that is: (1) substantially or essentially free from components which normally accompany or interact with it as found in its naturally occurring environment; or (2) if in its natural environment, the material has been non-naturally altered to a composition and/or placed at a locus in the cell not native to a material found in that environment. The isolated material optionally comprises material not found with the material in its natural environment. The alteration to yield synthetic material can be performed on the material within or removed from its natural state. For example, a naturally occurring nucleic acid becomes an isolated nucleic acid if it is altered, or if it is transcribed from DNA which is altered, by non-natural, synthetic methods performed within the cell from which it originates. Likewise, a naturally occurring nucleic acid becomes isolated if it is introduced by non-naturally occurring means to a locus of the genome not native to that nucleic acid.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polynucleotide" is a sequence of two or more deoxyribonucleotides (in DNA) or ribonucleotides (in RNA).

A "construct" is a nucleic acid molecule that is isolated from a naturally occurring gene or which has been modified to contain segments of nucleic acid which are combined and juxtaposed in a manner which would not otherwise exist in nature.

A "polypeptide" is a sequence of two or more amino acids.

A "promoter" is a cis-acting DNA sequence, generally located upstream of the initiation site of a gene, to which RNA polymerase may bind and initiate correct transcription.

A "recombinant" polynucleotide, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

A "recombinase recognition site" is a sequence of nucleotides that is recognized by and acted upon by a site-specific recombinase enzyme.

"Transformation" means the directed modification of the genome of a cell by the external application of recombinant DNA from another cell of different genotype, leading to its uptake and integration into the subject cell's genome.

A "transgenic" organism, such as a transgenic plant, is an organism into which foreign DNA has been introduced. A "transgenic plant" encompasses all descendants, hybrids, and crosses thereof, whether reproduced sexually or asexually, and which continue to harbour the foreign DNA.

A "vector" may be any of a number of nucleic acid sequences into which a desired sequence may be inserted by restriction and ligation. A vector typically carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmids, phage, phasmids, and cosmids.

A "transposase recognition site" is a sequence of nucleotides, which, in nature, is found at the 5' and 3' ends of a transposable element, and which are acted upon by a transposase enzyme during transposition of the transposable element.

Unless defined otherwise, all technical and scientific terms used herein have the same meaning as commonly understood to one of ordinary skill in the art to which this invention belongs.

In accordance with the subject invention, methods and compositions are provided for a novel means of producing transgenic plants and transgenic plants with novel DNA compositions.

In a most preferred embodiment of the present invention, oncogenic function is permanently inhibited by the use of repression strategies that delete or genetically interrupt the oncogenic region itself. In another embodiment of the invention, the oncogenes themselves are engineered to be responsive to novel repression strategies. In still other embodiments of the invention selected oncogenes are used rather than the entire complement of genes normally transferred to plant cells via wild-type *Agrobacterium*.

It is known that wild-type *Agrobacterium* generally transforms many different crop species at high efficiency. Numerous *Agrobacterium* species and strains have been described, the transfer of T-DNA and subsequent tumor formation process is generally conserved and dependent on the function of the introduced oncogenes of which there are many contained within the T-DNA region. It is also known that many *Agrobacterium* strains, such as nopaline or succinamopine can transform (i.e. form tumors) on many different plant species and virtually any genotype of *Brassica* species with high efficiency. The present method utilizes this efficiency as means to first derive a population of transformed cells from any species or genotype capable of being infected by *Agrobacterium*. These cells preferably contain the full complement of oncogenes and are not capable of regeneration to morphologically normal plants. Preferably, the oncogenes are introduced to the plant cell by *Agrobacterium*-mediated transformation in which the *Agrobacterium* used is an armed strain capable of conferring hormone independent growth on appropriate media.

In a most preferred embodiment of the method, the *Agrobacterium* strain is modified to include a Ti-plasmid that has been altered by the addition of recombinase recognition sites flanking the oncogenic region and a recombinase gene, capable of expression in a plant cell, under the control of an inducible promoter. In this embodiment, induction of the recombinase gene, leads to the expression of the recombinase in a transformed plant cell, causing the loss of the oncogenic region and allowing the plant cells to regenerate into whole plants. A preferred further method further comprises the introduction of a novel DNA sequence within the Ti-plasmid that is outside of the region excised by the recombinase but within the T-DNA border repeats of the Ti-plasmid. In this fashion, loss of the oncogenic region from the inserted DNA produces a plant cell wherein the novel DNA sequence is stably inserted into the plant genome.

Since this method does not require regeneration from the first transformation event, and utilizes regeneration of normal plants as the selective step in the second transformation event, many common steps and components that are of variable or low efficiency in typical transformation protocols are avoided. The general outline of the method is shown in FIG. 1.

This method also provides certain advantages in relation to selection. First, it is not required to have a selective agent as part of the procedure. The initial transformation event relies on the hormone independent growth of the transformed cells due to the expression of the oncogenes. These cells can be selected for by simply plating on hormone free media. This process has been used for many years to score *Agrobacterium* infectivity. Only transformed cells (cells with oncogenes) grow on hormone free media. Thus it is a simple matter to obtain a population of cells, all of which are transformed. As part of the present method, these populations of cells are further manipulated by a transient expression event (which activates a DNA construct capable of causing loss of the oncogenic region) that generates cells capable of regeneration, usually directly from a population of cells originally containing oncogenic region, typically without the needs for added hormones or prolonged and complicated tissue culture procedures.

The elimination of selection can provide higher regeneration efficiencies since the need to balance the toxic effects of the antibiotic and the death of non-transformed cells (with subsequent negative effects on transformed cells) is eliminated. This particular step (selection vs. regeneration) has been difficult for many plant species and in particular *Brassica* genotypes. Indeed, selectable markers based on killing non-transformed cells can be efficient, but also require significant manipulation in culture and time in order to be used.

This new method provides many advantages in developing transgenic lines since less tissue culture experimentation with new genotypes is required and prolonged regeneration protocols are minimized.

The attributes of this system include:

(a) the elimination of selectable markers as the selection process is based on regeneration.

(b) genotype independent transformation. Wild type *Agrobacterium* has been shown to transform nearly all varieties within a genus or species. Even difficult to transform crops such as sunflower will benefit from such an approach.

(c) minimal tissue culture manipulations. The elimination of toxic selective agents allows for simpler tissue culture protocols to be used.

(d) rapid generation of transformed plants. With minimal tissue culture manipulations and no need for selection, it is possible to rapidly recover transgenic plants.

(e) reduced effort in generating transgenic plants. With the present method, numerous independent transformation events can be conveniently cultured in liquid or solid cultures and induced to regenerate at once.

Thus the present method finds utility for producing transgenic plants in many plant species.

In accordance with the invention, various methods may be employed to (1) produce plant cells that initially comprise oncogenic activity convenient for the selection of transformed plant cells, and are (2) subsequently modified to eliminate the activity of the oncogenic region of the T-DNA to permit regeneration to morphologically normal plants.

The initial step formation of tumor cells) can be carried out in a number of different ways. These include direct inoculation of whole plants, inoculation of sterile plant tissue or plant explants, or inoculation of decapitated plantlets. Tumor cells are simply cultured on minimal media, or in some cases tumor cells are allowed to grow directly on the inoculated plant.

Once oncogene function is inhibited or eliminated, standard regeneration protocols for that plant species are applied, since the entire population of cells will be transformed and there is no need to apply a selective agent. In this fashion, it is a simple matter to alter tissue culture conditions to lead to regeneration of plants, and all plants regenerated will be transformed. In some instances, the regeneration of transgenic shoots may occur directly on infected plants, i.e., in those plants where the inoculation is performed on decapitated plants shoots are able to form directly from crown gall tissue following inactivation of the oncogenic region.

This transformation and regeneration procedure is in contrast to toxic selection techniques where plant cells are first subjected to the transformation process and then subjected to the presence of a phytotoxic agent and introduced genes are linked to a selectable marker that detoxifies the agent. Regeneration is therefore dependent on the selection of transformed cells within a population of non-transformed cells. The present invention allows the formation of a population of cells that are substantially all transformed, and regeneration takes place without the selective pressure of a phytotoxic agent.

A first aspect of the present invention contemplates the use of naturally occurring oncogenes, found in wild-type T-DNA of *Agrobacterium* and the naturally occurring highly efficient plant transformation process of the *Agrobacterial* genus to first produce transformed plant cells, which because of the hormone independent growth of said cells as a result of the expression of the oncogenes, permit the easy identification of transformed cells.

Indeed, it has been found that the wild-type *Agrobacterium* transformation process, which leads to the formation of galls, is often efficient and capable of forming tumors on a wide variety of plant species and varieties, including those generally recalcitrant to transformation with dis-armed strains of *Agrobacterium* (e.g. strains where the oncogenes have been deleted from the T-DNA). Accordingly, plant cells carrying the oncogenic T-DNA can be easily obtained and identified without the need for a toxic selective agent.

In the second step, novel strategies for the elimination of the oncogenic region, or elimination of oncogene function are employed to produce cells transformed and capable of regeneration to morphologically normal plants.

In a most preferred embodiment of the invention, the Ti-plasmid is modified to comprise recombinase recognition sites and a recombinase gene that can be expressed in the plant cell under appropriate conditions. Upon expression, the oncogenic region, or portions thereof are excised, eliminating the tumor phenotype and allowing for the regeneration of whole plant cells from the initially transformed plant cells. Inclusion of a DNA sequence in the Ti-plasmid encoding a novel trait permits the recovery of whole plants comprising a novel trait inserted into the plant genome.

In another embodiment of the present invention, the cells transformed with the oncogenic region of the T-DNA are then subjected to a second transformation event with a DNA construct that inhibits the activity of the oncogenes such that morphologically normal plants can be conveniently induced to form from the population of cells initially expressing the oncogenes.

In both above embodiments of the method, the use of direct selection on a population of transformed cells is avoided. The method allows for the recovery of transformed morphologically normal plants from transformed oncogene containing cells since inhibition of the oncogenes allows cells to regenerate into morphologically normal plants. By avoiding the use of selective agents that kill non-transformed cells, and relying on a conversion from a morphologically abnormal state to a morphologically normal state, recovery of whole plants occurs in a convenient and efficient fashion.

In a most preferred embodiment of the present invention, the use of a site-specific recombinase is contemplated as a means to eliminate oncogene activity. The use of recombinases can provide a direct means to eliminate oncogene function in transformed cells. Furthermore, if a transgene of interest is included between the *Agrobacterium* T-DNA borders (but outside of the region that is excised by the site specific recombinase), the resultant cells, following exposure to the recombinase, contain only the transgene. The cells are then capable of regeneration to morphologically normal plants.

For example, the T-DNA can be modified (for example site-specific mutagenesis or homologous recombination as a means to introduce new DNA sequences) to provide sites capable of recognition by site specific recombinases. These DNA sequences, which are typically short (less than 40 base pairs, often less) can be introduced as flanking regions within the T-DNA borders (i.e. within the portion of DNA transferred to plant cells), oncogenes being contained between two of these sequences. Introduction of a recombinase activity would cause the specific excision of the oncogenes, leaving the T-DNA borders (and any associated novel transgene) in place. The recombinase activity could be introduced by stable transformation, transient expression of DNA, such as by biolistics or even viral infection of said cells with recombinant virus containing the recombinase gene, or by introduction of the recombinase enzyme through various means such as electroporation. In a most preferred embodiment, the recombinase gene is included in a Ti-plasmid, but is under the control of an inducible plant promoter such that expression of the recombinase (and loss of the oncogenic region) can be accomplished by placing the cells containing the oncogenic region under appropriate induction conditions.

The steps employed to derive such a vector can include the construction of a vector comprising a recombinase recognition site flanked by two regions of homology to a border region. In this fashion, a double crossover event causes the insertion of the recombinase recognition site into the border region of the T-DNA. The region of homology can be anywhere within the border region, but it must be chosen to leave the T-DNA border repeat intact and lie within the region of DNA typically transferred to plant cells. For convenience, an antibiotic selectable marker is included to facilitate the recovery of cells containing the modified Ti-plasmid. It is convenient to carry out the modification in steps, typically modification of a first border, for example the right border region, recovery of a modified Ti-plasmid comprising a recombinase sequence at the right border. The modified right border Ti-plasmid is then subjected to a second round of modification, using regions of homology to the left border region to introduce a recombinase site at the left border region as before, to recover a Ti-plasmid modified at both the left and right borders.

Additional variations are contemplated for convenience. In one variation, the first antibiotic marker is flanked by identical recombinase recognition sites, such that the removal of the antibiotic marker by expression of the recombinase in the bacteria allows the recovery of a first modified Ti-plasmid free of antibiotic marker genes. By employing such a strategy it is possible to use the same marker to introduce both recombinase sites, following the removal of the first antibiotic marker introduced by the first homologous recombination event. It is also possible to include a plant marker gene in the DNA constructs used for modification of the Ti-plasmid. The plant marker gene is arranged to be activated upon successful excision of the T-DNA in the plant cell by induced or introduced recombinase activity. In this fashion, loss of oncogenic function can be conveniently scored.

Many site specific recombinases have been described in the literature (Kilby et al., *Trends in Genetics*, 9(12): 413–418, 1993). The three recombinase systems that have been extensively employed include: an activity identified as R encoded by the pSR1 plasmid of *Zygosaccharomyes rouxii*, FLP encoded for the 2 m circular plasmid from *Saccharomyces cerevisiae* and Cre-lox from the phage P1. All of these recombinase systems have been shown to function in heterologous hosts. For example R has been demonstrated to work in tobacco cells (Onouchi et al., *Nucl. Acids. Res.* 19(23):6373–6378, 1991, incorporated herein by reference). FLP has been shown to be functional in tobacco and Arabidopsis (Kilby et al., *The Plant Jour.* 8(5):637–652, 1995, incorporated herein by reference), and Cre-lox has been shown to be functional in tobacco (Russell et al., *Mol. Gen. Genet.* 234:49–59, 1992, Odell et al., *Mol. Gen. Genet.* 223:369–378, 1990, Dale and Ow, Gene 91:79–85, 1990, Dale and Ow, *Proc. Natl Acad. Sci. USA* 88:10558–10562, 1991, Haaren and Ow, *Plant Molecular Biology* 23:525–533, 1993, incorporated herein by reference). Accordingly the use of site specific recombinases for directing homologous recombination in higher cells is well documented. Within the scope of the present invention the excision function of site-specific recombinases is contemplated as a means to assist in the elimination of oncogene activity.

The recombinase gene is typically modified to prevent expression in bacterial cells, and restrict expression to plant cells. This is particularly important for those embodiments where the recombinase gene is contained within the border regions of the modified Ti-plasmid, since expression of the recombinase gene in bacterial strains, such as the *Agrobacterium* strain comprising the modified Ti-plasmid would lead to the loss of the T-DNA. Thus, in these cases the recombinase gene is modified to contain an intron to restrict the expression in bacteria. The intron typically is modified to contain at least one stop signal to ensure no expression of the recombinase activity in bacteria.

The modification of the Ti-plasmid can take place with any *Agrobacterium* species capable of conferring a phenotype that includes hormone independent growth and inability to regenerate to morphologically normal plants. Wild-type T-DNA or Ri-DNA can be used as well as modified forms thereof. A combination of oncogenes normally found within the T-DNA or Ri-DNA can be used. The actual combination will be dependent on the particular plant species to be transformed as well as convenience. The *Agrobacterium* species contemplated for use in the present invention includes *A. rhizogenes, A tumefaciens* (nopaline, octopine, agropine strains) *A. vitis,* or any other strain capable of transferring oncogenes to plant cells. In particular the use of the nopaline strain C58 is preferred. These *Agrobacterium* strains are commonly available from the American Type Culture Collection.

The method to modify the Ti-plasmid can comprise many different steps, but in general the following steps are employed (these are illustrated diagrammatically in FIGS. 4–7):

construction of a vector, containing regions of homology to the T-DNA region of a Ti-plasmid said regions flanking a recombinase recognition site;
 triparental mating to introduce the vector comprising the recombinase recognition site into an *Agrobacterium* strain comprising a Ti-plasmid and recovery of a Ti-plasmid modified to contain a recombinase recognition site;
 repeating the procedure again with a different region of homology to derive a Ti-plasmid with two recombinase recognition sites located in the desired positions.

It is common practice in the art to utilize homologous recombination in bacteria to derive extrachromosomal elements that have new DNA sequences inserted as a result of the recombination event. In the present case, two regions of homology are used to flank the recombinase recognition site to ensure that only the region between the two homologous sequences is inserted into the Ti-plasmid. It has been found convenient to include an antibiotic resistance marker to select for stable recombinants. As described, it is possible to flank the antibiotic marker with recombinase recognition sites to allow for the deletion of the marker once inserted into the Ti-plasmid. For most recombinase enzymes, the deletion of a sequence bound by two recombinase sites leads to the formation of a single recombinase site subsequent to the deletion.

It has also been found convenient to include the recombinase gene itself in one of the vectors used to insert a second recombinase recognition site in a Ti-plasmid. The recombinase gene is modified to contain a plant intron to prevent expression in bacterial cells, and is under the control of an inducible plant promoter. In exemplified cases, two inducible promoters are used for demonstration, the cold-inducible promoter from Brassica (Genbank Acc. N. U14665) and the tet operator/repressor system (Gatz and Quail, Proc. Natl. Acad. Sci. USA 85: 1394–1397, 1988, incorporated herein by reference). Other inducible or controllable promoters known in the art may be used within the scope of the present invention. For example, Mett et al., (Proc. Natl. Acad. Sci. USA 90 4567–4571, 1993, incorporated herein by reference) describe a gene expression system derived from the yeast metallothionin gene. The authors demonstrated that a chimeric plant promoter containing a DNA sequence referred to as ACE 1 can be repressed by metallo-active transcription factor and de-repressed in the presence of copper ions. Additionally a mammalian derived gene expression system has been shown to function in plant cells. Schena et al., (Proc. Natl. Acad. Sci. USA 88: 10421 10425, 1991, incorporated herein by reference). In this gene expression system the glucocorticoid transcriptional factor and DNA encoding the glucocorticoid responsive elements are utilized with plant genes to provide a gene expression system that inhibits gene expression but can be de-repressed in the presence of steroid hormones.

The recombinant DNA molecule comprising the modified T-DNA of the Ti-plasmid can additionally comprise a gene encoding a "novel trait" which could be any recombinant protein or peptide of interest, typically this "novel trait" could be a heterologous protein of commercial interest or a protein that confers an agronomically useful trait such as herbicide tolerance. These traits could include insect resistance, such as the Bt insecticidal protein gene, examples of the methods for modification and use of Bt coding sequences in plants can be found in U.S. Pat. No. 5,380,381, incorporated herein by reference. Other strategies for control of insect predation in plants include genes encoding protease inhibitors (U.S. Pat. No. 5,436,392, incorporated herein by reference), insect venom proteins (U.S. Pat. Nos. 5,441,934 and 5,177,308, incorporated herein by reference) and various other proteins. Still other traits could comprise genes encoding fungal or disease resistance, (for example see *Defense-related proteins in higher plants*. Bowles, D. J., Annual Review of Biochemistry 1990 59: 873–907; or U.S. Pat. Nos. 5,703,044 and 5,607,919, all of which are incorporated herein by reference), genes encoding a trait related to quality such as reduction of ethylene formation to retard ripening (e.g. as described in U.S. Pat. Nos. 5,998,702; 5,859,330; and 5,916,250, incorporated herein by reference), genes encoding an enzyme capable of making a nutraceutical product such as increased vitamins (e.g., International Publication No. WO 99/53041 incorporated herein by reference) or increased production of secondary metabolites of commercial value, or genes controlling the biochemistry or physiology of plant development, such as delayed or induced flowering, (e.g., homeotic genes such as LEAFY (Weigel and Nilsson, Nature 277:495–500, 1995, Session et al., Science 289: 779–781, 2000, incorporated herein by reference) reduction of seed in fruit (e.g., International Publication No. WO 97/40179, incorporated herein by reference), etc. The scope of the invention is not limited by the novel trait. Indeed, it is contemplated that even large genomic DNA fragments comprising a multiplicity of genes can be transferred by the present system, given the ability of *Agrobacterium* to transfer large regions of DNA.

It is clear that a gene encoding a novel trait can be added to the plasmids used to modify the wild-type C-58. Said novel trait may be added upon modification of the right border sequences or the left border sequences. Thus, it is possible to add any number of genes encoding novel traits by orienting the gene encoding the novel trait relative to the recombinase recognition site such that upon activation of the recombinase enzyme the wild-type T-DNA and recombinase enzyme coding region is excised, leaving the novel trait or traits flanked by the T-DNA borders.

Figure 8:
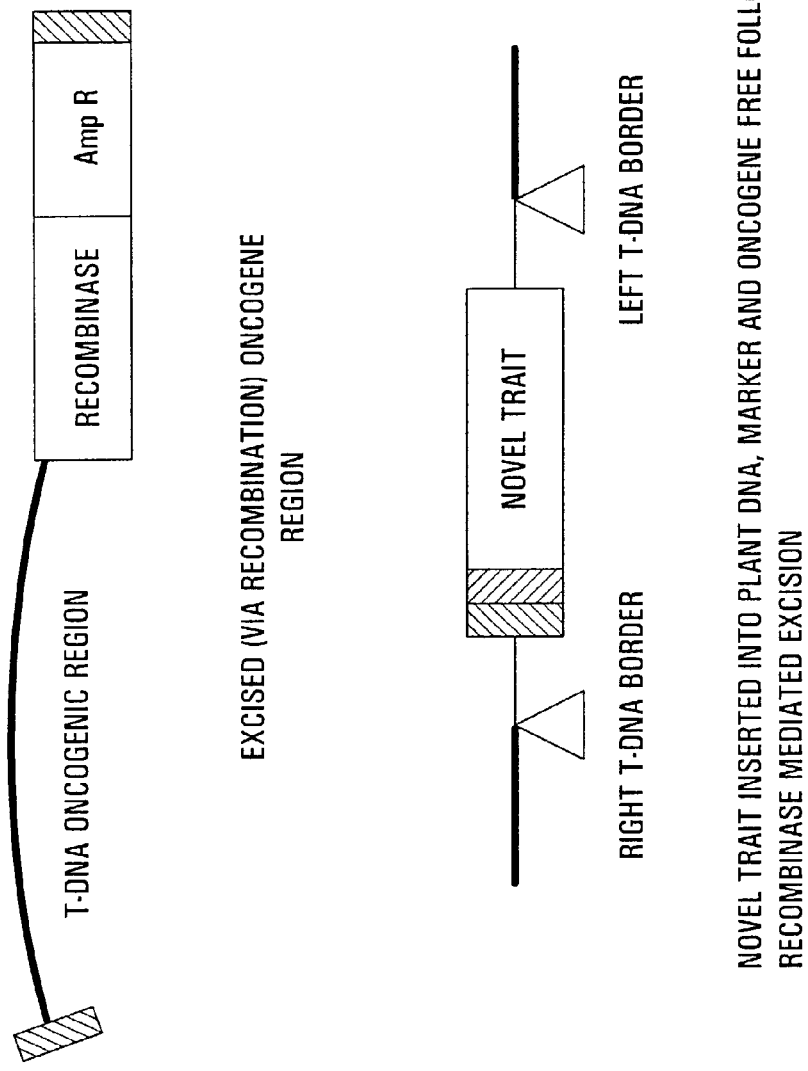
FIG. 8 illustrates the result of the expression of the recombinase gene in plant cells transformed with the modified Ti-plasmid. The oncogenic region is lost and the plant DNA contains only the gene encoding the novel trait.
Figure 9A:
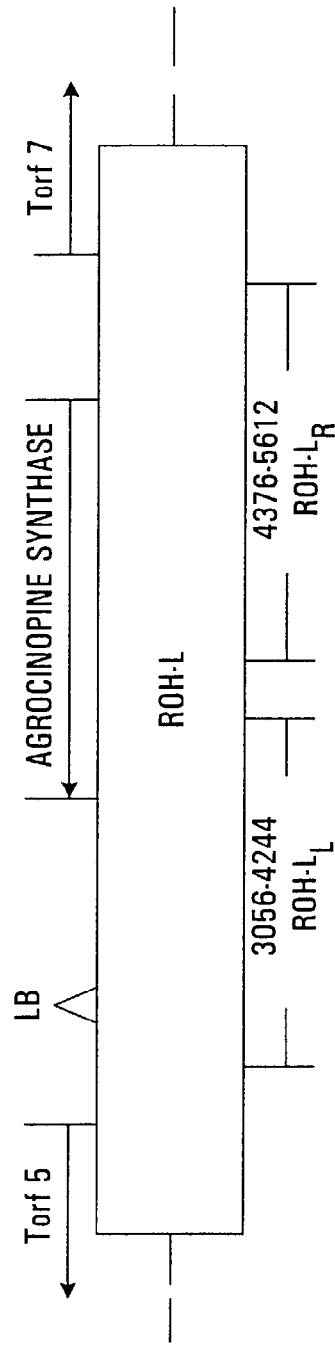
FIGS. 9A and 9B illustrate the regions of homology used for the construction of modified Ti-plasmids. The regions of the nopaline Ti-plasmid used are shown. ROH refers to region of homology, the "-$R_L$, -$R_R$, -$L_L$ and -$L_R$" refer to the sub-regions (i.e. portions) of homology (right (9B) and left (9A) regions) used in the construction of vectors for homologous recombination in *Agrobacterium*.
Figure 9B:
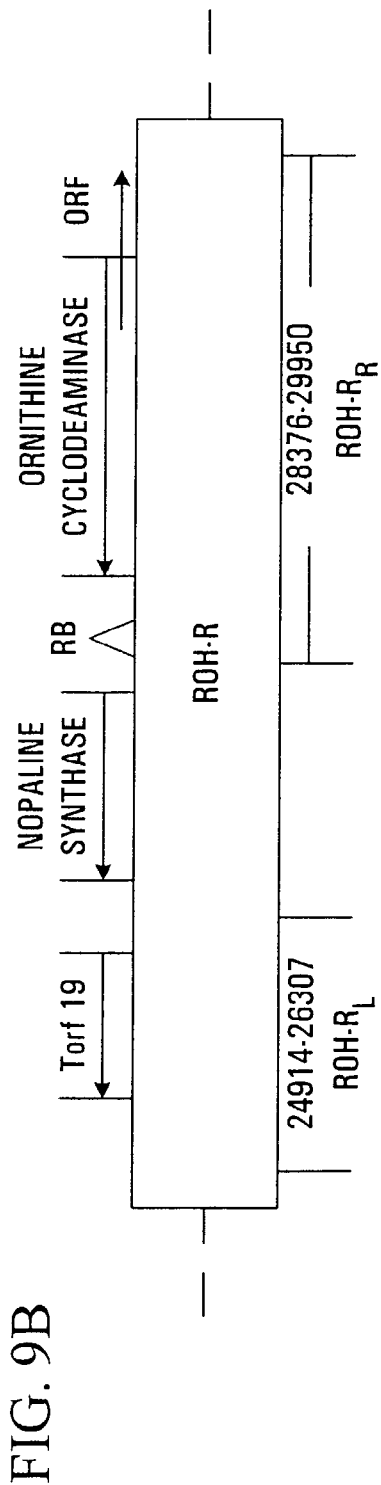

Following recovery of the modified Ti-plasmid, *Agrobacterium* strains are prepared, plant cells are transformed, cells containing the oncogenic region are cultured under hormone free conditions, or minimal media conditions, and transformed cells are allowed to proliferate, while non-transformed cells are eliminated. After this period of time, the recombinase activity is induced. The recombinase activity eliminates the oncogenic region, leaving behind the novel trait and a small region of the T-DNA bounded by the Left and Right T-DNA borders. This is shown in FIG. 8.

It should be noted that in some instances it may be desirable to leave only the recombinase site in the plant DNA following excision of the oncogenic region. In this fashion, it is possible to utilize the recombinase site for the further introduction of genes via the use of a recombinase-mediated integration of DNA. Further, the recombinase sites may be scattered throughout the genome of the plant by selecting various transformed cell lines, each with a different site of insertion. These individual plant lines may be regenerated and crossed, leading to the formation of plant lines that comprise many recombinase recognition sites, scattered throughout the genome of the plant. It is then possible to utilize the recombinase enzyme to re-arrange, duplicate or delete regions of the plant genome, allowing for the generation of new genotypes and genetic combinations. Thus, the invention has a further utility in plant genetics, namely the use of the method to introduce a multiplicity of recombinase recognition sites in a plant genome, the sites able to be utilized by a recombinase to alter the arrangement of the plant genome by the use of a recombinase activity. The recombinase can be introduced in a second transformation event, or can be present in the plant genome under the control of an inducible promoter such as those described herein. The recombinase can also be introduced by crossing with a plant engineered to express the recombinase, either constitutively or more preferably under the control of an inducible promoter or a tissue specific promoter. A pollen-specific or microspore specific promoter controlling the expression of the recombinase is preferred as this will lead to the production of a population of pollen cells comprising novel genetic arrangements following the introduction of the pollen-expressed recombinase in plant cells wherein the genome contains a multiplicity of recombinase sites.

Although the art has described the use of the Cre-lox recombinase system to cause a chromosome recombination event (Qin et al, Proc. Natl. Acad Sci., USA 91:5, 1706–1710, 1994), the art does not appear to contemplate a method to conveniently insert numerous recombinase recognition sites into a plant genome without the use of a selectable marker. The need for a selectable marker limits the number of events one can produce carrying a recombinase site, thus limiting the utility of the procedure. In the present invention any number of recombinase sites can be introduced, and the method can be adapted to produce plant cells with genomes altered to only contain recombinase sites without addition coding sequences. Another use for an introduced recombinase site is to provide a region for site-specific integration of a novel trait by the use of recombinase mediated gene insertion.

The region that remains in the plant chromosome can also comprise a gene from the oncogenic region, or a portion of a gene from the oncogenic region. There are many different oncogenes within the oncogenic region, including genes encoding the formation of opines, thus it may be preferred in some cases to insert the recombinase recognition site to allow for removal of a portion of the oncogenic region while leaving one or a portion thereof of an oncogene normally found in the oncogenic region.

In addition to recombinases, the use of transposases to eliminate or excise oncogenic regions of a modified Ti-plasmid is contemplated. Known transposons and associated transposase activities include Ac/Ds and En/Spm elements from maize (e.g. see Federoff, N. *Maize Transposable Elements*. In Berg, D. E. and Howe, M. M. (eds) Mobile DNA, pp. 375–411, American Society for Microbiology, Washington, D.C., 1989), Tam-1 and Tam-3 from snapdragon (e.g. see Sommer et al, Transposable Elements of *Antirrhinum majus*. In *Plant Transposable Elements*, O. Nelson, ed, Plenum Press, New York, pp.227–235, 1988), Tnt-1 from tobacco (Pouteau, S. et al, *Mol Gen Genet.* 228:233–239, 1991), Tph-1 from petunia (Gerats A. G. M. et al, *The Plant Cell* 2:1121–1128, 1991) and the Tst-1 element from potato (Koster-Topfer, et al, *Plant Mol. Biol* 14:239–247,1990), all of which are incorporated herein by reference.

A transposon has certain features such as a central coding region encoding a transposase enzyme and DNA sequences at the 5' and 3' end of the transposon that are recognized by the specific transposase. When the transposase acts upon these sequences, transpostion of the transposable element occurs. Artificial transposons have been constructed which comprise heterologous genes. These recombinant transposons can transpose in the presence of the transposase enzyme. In accordance with the invention, the sequences recognized by the transposase can be linked to the oncogenes in a fashion that permits the excision of the oncogenes by the transposase enzyme. The transposition or excision event irreversibly inactivates the oncogene function. Transposons can be modified to reduce or eliminate re-insertion into other chromosomal locations, or the arrangement of the transposase recognition sites is structured to irreversibly delete a portion of the oncogene. For example, oncogenes can be modified to have transposase recognition sites between the promoter of a modified oncogene and the coding region, such that transposition effectively eliminates a portion of the coding region or promoter, thus inactivating the oncogene. Any number of strategies may be employed to utilize transposition as a means to inactivate oncogene function.

The use of transposase activities to specifically cause transposition (or loss) of oncogenes is contemplated within the scope of the invention. Indeed, it is possible to modify the T-DNA to contain DNA sequences capable of being recognized by a transposase enzyme such that upon exposure to the transposase enzyme, the oncogenes are excised from the original location of insertion, with subsequent loss or low frequency of transposition to another site. Thus, transposons, when properly modified, can be used as a means to favor the excision of the oncogenes within the scope of the invention.

The oncogenic T-DNA region of the nopaline strain of *Agrobacterium* provides preferred DNA components. The art has described the structure and function of these genes, allowing the skilled artisan to devise specific DNA constructs and culture conditions that provide optimum transformation efficiency. The nopaline strain is preferred as the T-DNA of the nopaline strain C-58 is a single T-DNA region as contrasted to octopine strains that comprise a pseudo duplicated T-DNA such that there is a "right" and "left" T-DNA region. Within the C-58 nopaline T-DNA there are oncogenes of known function such as oncogenes 1,2 & 4, as well as oncogenes of undefined function such as 5, 6b, as well as genes encoding nopaline synthase (nos), agrocinopine synthase (acs), octopine, nopaline secretion (ons) and others. Combined, the activities of these oncogenes lead to the formation of crown galls.

Oncogene 1 encodes the enzyme Indole Acetamide Synthase (IAMS) that converts tryptophan, an amino acid normally found in plant cells to indole acetamide. The function of oncogene 1, that is the conversion of tryptophan (a endogenous amino acid contained within all plant cells) to indole acetamide is described by Van Onckelen et al., *FEBS lett.* 198, 357–360, 1986, incorporated herein by reference.

Oncogene 2 encodes the enzyme Indole Acetamide Hydrolase (IAMH) which converts indole acetamide to indole acetic acid. The function of gene 2, that is the ability to convert indole acetamide to indole acetic acid, was demonstrated by Tomashow et al., *Proc. Natl. Acad Sci. USA* 81, 5071–5075, 1984 and Schroder et al., *Eur. J. Biochem.* 138, 387–391, 1984, incorporated herein by reference. Specifically oncogene 2 in concert with oncogene 1 provide for the synthesis of the plant growth regulator indole acetic acid from tryptophan via a pathway found in bacterial cells but not in plant cells. Related oncogene activities are found in *A. rhizogenes, A. vitis* (Canaday, J. et al., *Mol. Gen. Genet.* 235:292–303, 1992) and *Pseudomonas savastanoi* (Yamada et al., *Proc. Natl. Acad. Sci. USA,* 82:6522–6526,1985), incorporated herein by reference.

Oncogene 4, encodes isopentyl transferase and can synthesize a cytokinin activity.

In addition to these well-defined individual oncogenes, the T-DNA region contains a number of other genes that are involved in the oncogenic process and hence are considered oncogenes. Many of the genes are involved in the regulation of the formation of tumors and hence play an important role in the efficiency of tumor formation. Thus the cells transformed with the entire complement of oncogenes can grow very rapidly and under conditions that favor their growth at the expense of non-transformed cells, but only in a disorganized fashion leading to the formation of crown galls. In total, the complement of oncogenes found in the C58 strain provide the genetic function required for the formation of crown gall tissue.

For some plant species, a portion of the normal complement of oncogenes may be employed. Indeed, one or more oncogenes may be used, and the culture media adjusted to provide a level of phytohormone that would normally be found by expression of all of the normally expressed oncogenes. Thus plant cells resultant from the first transformation event may not exhibit complete hormone independent growth, but under certain conditions of culture exhibit a phenotype which is similar to hormone independent growth and incapable of regeneration to morphologically normal cells. These cells would then be subject to expression of the recombinase and culture conditions would then be selected to provide said transformed cells with the ability to regenerate to morphologically normal cells. In this fashion, the use of a limited number of oncogenes is contemplated, thus simplifying the method.

For these embodiments of the invention, the oncogene activities of choice are the oncogenes 1 and 2 from the Ti or Ri plasmid of *Agrobacterium* and the oncogene 4, which causes the production of cytokinins as well as the other oncogenes commonly found associated with these other oncogens within the Ti- or Ri-DNA region. The activity of these genes combined leads to hormone independent growth. The phytohormone activity of these genes can be substituted in many cases by endogenously applied phytohormones.

Figure 3:
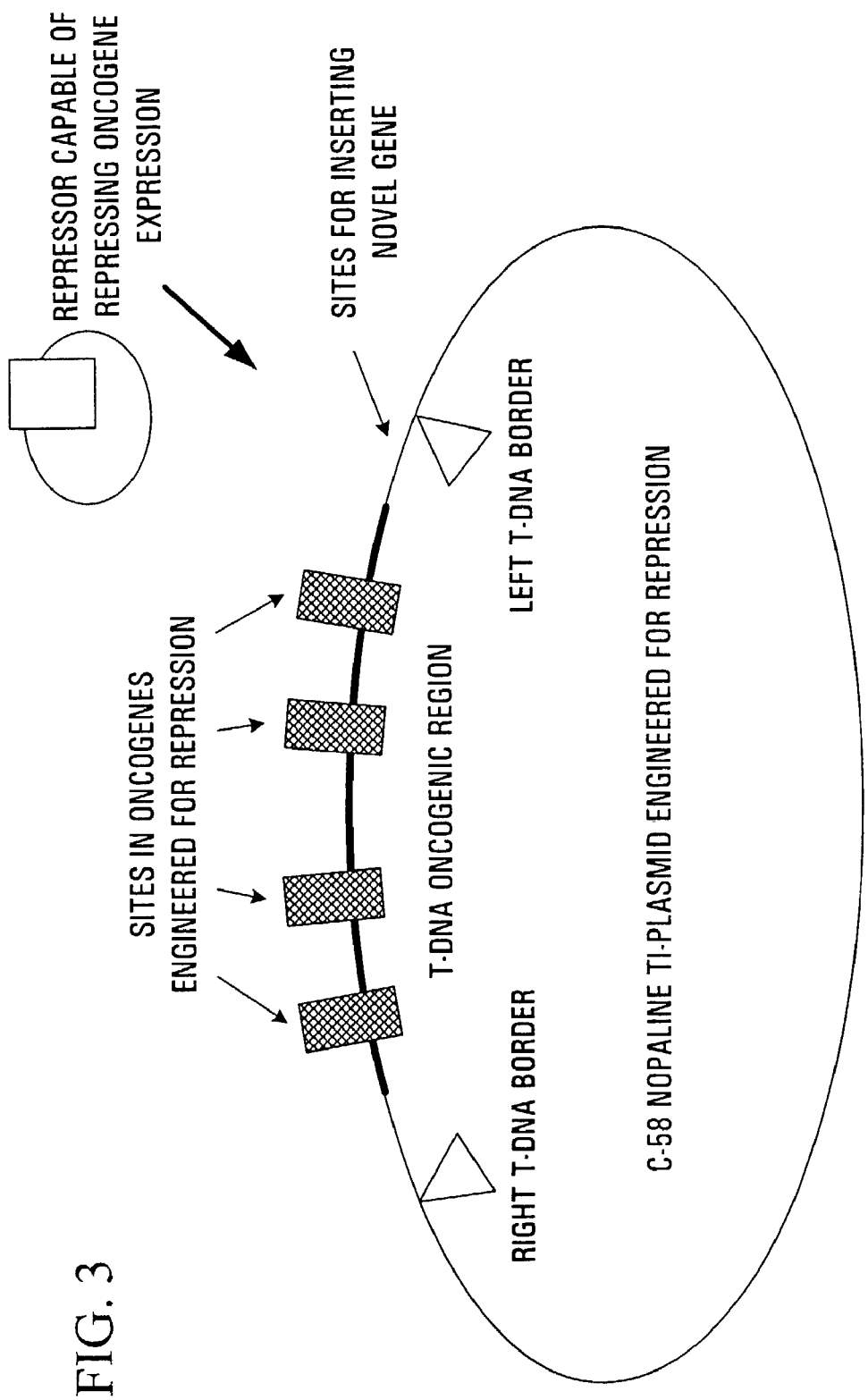
FIG. 3 illustrates the use of a repression strategy that may be employed to eliminate oncogene function in plant cells transformed with oncogenes.
Figure 4:
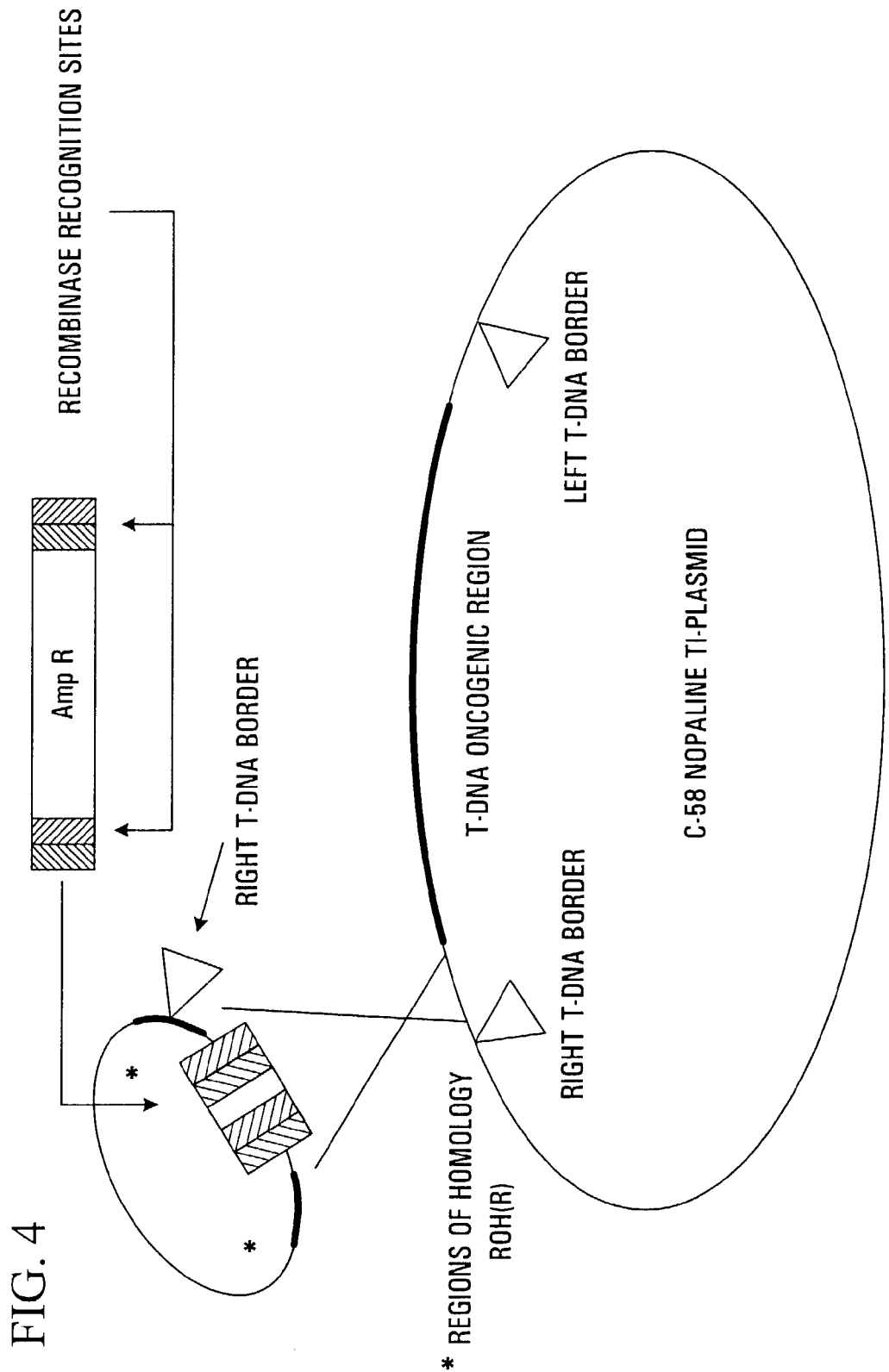
FIG. 4 illustrates the derivation of a modified Ti-plasmid comprising a recombinase recognition site at the Right T-DNA border. The use of an ampicillin marker gene to first select for the homologous recombination event is shown.
Figure 5:
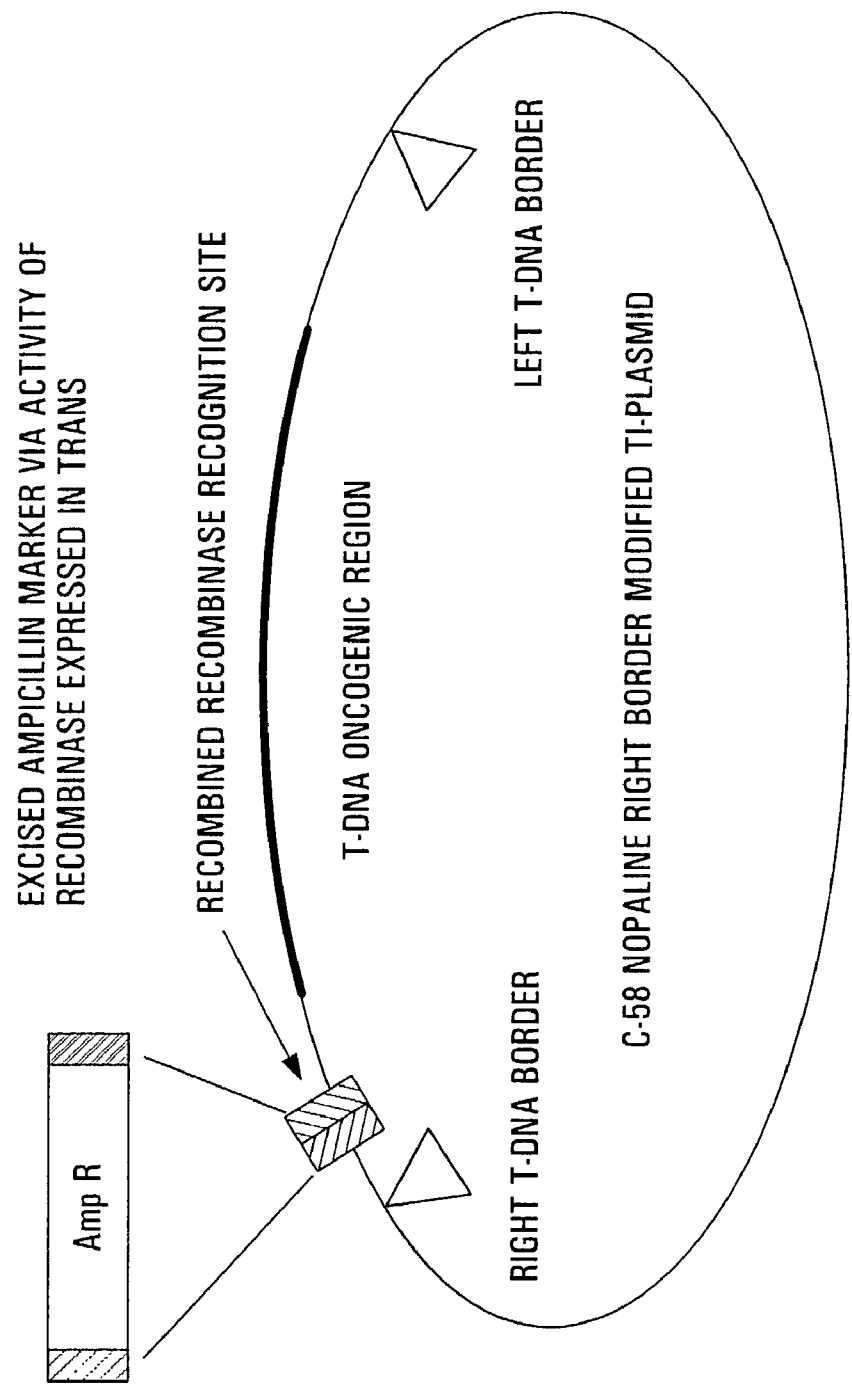
FIG. 5 illustrates the use of a recombinase enzyme to excise an ampicillin marker gene to derive a modified Ti-plasmid that comprises a recombinase recognition site at the Right T-DNA border.
Figure 6:
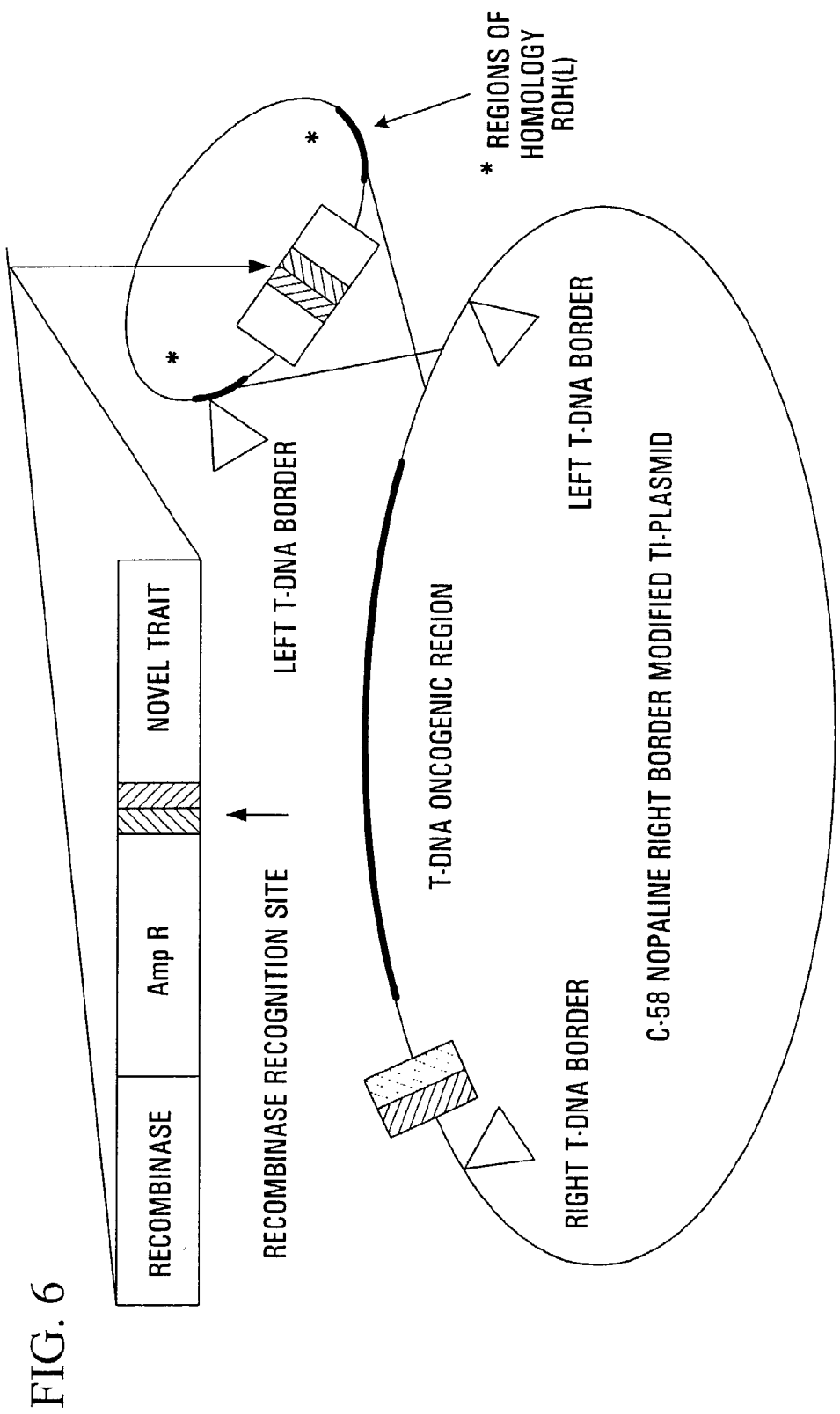
FIG. 6 illustrates the derivation of a modified Ti-plasmid comprising a recombinase recognition site, recombinase gene and ampicillin marker at the Left T-DNA border.
Figure 7:
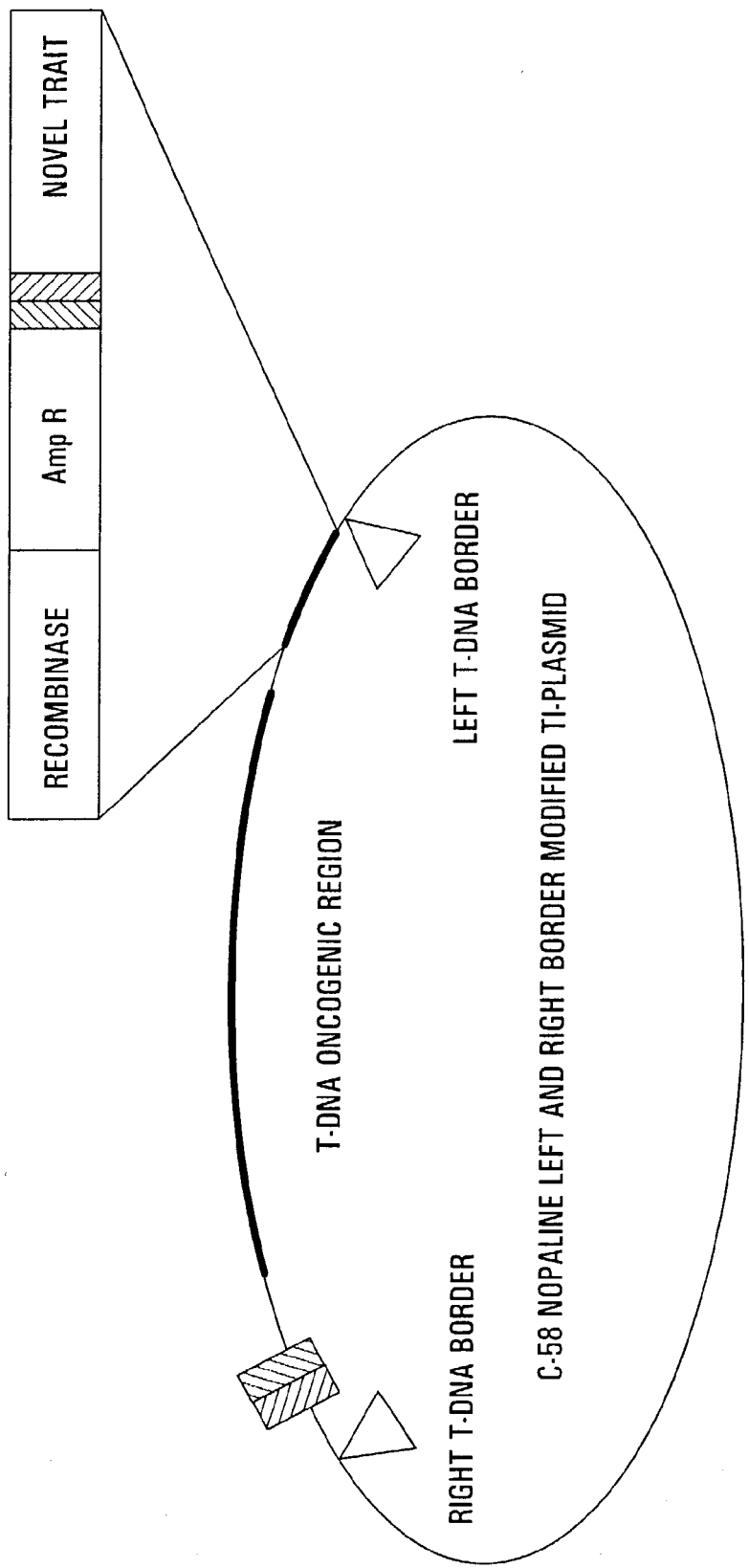
FIG. 7 illustrates the use of the ampicillin marker gene to select a modified Ti-plasmid that comprises recombinase sites at the Left and Right T-DNA borders as well as a bacterial marker and plant expressible recombinase gene.

When these oncogenes genes are turned off, or silenced in one manner or another, the cells can grow normally and in many cases cells can regenerate to morphologically normal plants. Thus the silencing of the oncogenes can be used as a selectable event in tissue culture. The various means that can be used to silence such as repression are illustrated in FIG. 3. In this aspect of the invention, a second DNA is expressed that encodes a repressor capable of eliminating oncogene expression or function.

There are many ways in which a gene can be silenced or the activity repressed. In the context of the present invention any mechanism that effectively blocks the accumulation of the product of said oncogenes in a cell comprises repression. Said methods may include: the binding of a specific "repressor protein or factor" to a DNA region or "operator" within the promoter of said oncogene. The promoter region of the oncogene can be conveniently modified to be responsive to this repressor element. Examples of these DNA binding proteins described in the art include bacterial repressor elements and associated DNA binding regions (operator DNA) such as the Lac Z repressor or the tet repressor or other bacterial repressors. Other examples of bacterial repressors may be found in the class of repressor proteins includes: LacR, GutR, DeoR, FucR and GlpR that regulate sugar catabolism in bacterial systems (van Rooijen, R. J. and de Vos, W. M., *J. Biol. Chem.* 265:18499–18503, 1990, incorporated herein by reference) or the *Agrobacterium* repressor known as accR that regulates the biosynthesis of agrocinopines and conjugal transfer (Bodman et al., *Proc. Natl Acad Sci USA* 89:643–647, 1992 incorporated herein by reference). Any other repressor may be employed within the scope of this invention. Other sources of repressors can be employed including those found in fungi such as yeast or any other organism. One example of a gene expression mechanism capable of inhibiting the expression of a gene is the LexA system (U.S. Pat. No. 4,833,080, incorporated herein by reference). The LexA mechanism utilizes a repressor and a specific DNA operator sequence to control gene expression. Other sources may include a yeast derived system (Mett et al., Proc. Natl. Acad. Sci. USA 90 4567–4571, 1993, incorporated herein by reference) a mammalian derived gene expression system (Schena et al., Proc. Natl. Acad. Sci. USA 88: 10421 10425, 1991, incorporated herein by reference), and artificial systems. For example, U.S. Pat. No. 5,198,346, incorporated herein by reference describes methods to generate novel DNA binding proteins, in particular repressors of gene expression that can be employed within the scope of the present invention. In the present invention, the repressor may be capable of binding a specific DNA sequence that can be inserted into the transcriptional control sequences of the oncogene(s), the binding capable of substantially inhibiting the expression of the oncogene.

Other DNA binding proteins that have been modified to bind strongly to specific DNA sequences, so called "transdominators" may also be employed. Other repressors may include antisense RNA directed to the oncogene. Other repression strategies aimed at elimination of gene expression can be employed within the scope of the method. Three predominant methods have been described for achieving inhibition of gene expression, anti-sense RNA, co-suppression and ribozyme technologies. Methods for utilizing anti-sense RNA have been described for example U.S. Pat. Nos. 4,801,540 and 5,107,065, incorporated herein by reference. The process of co-suppression of gene activity is described by Jorgensen et al, 1991, U.S. Pat. Nos. 5,034,323 and 5,283,184, incorporated herein by reference. The use of ribozymes is described by Cech et al U.S. Pat. Nos. 4,987, 071 and 5,116,742, incorporated herein by reference.

Thus there are many ways that method of the present invention can be used to derive transgenic plants. Accordingly, the invention finds utility across a range of species and plant varieties. Any plant species capable of being transformed by wild type *Agrobacterium* can be subjected to the present method and morphologically normal transformed plants can be easily obtained. Any number of repression schemes can be used including repression of gene activity, elimination of oncogenes through recombination or transposition, or addition of a protein that negates the activity of the oncogenes. This could include a protein capable of binding the products of the oncogene, such as auxin or cytokinin binding proteins, or an enzymatic activity capable of conjugating or metabolizing products of the oncogenes, such as an auxin conjugating enzyme or a cytokinin conjugating enzyme. Thus the method finds utility across a range of crops and for various purposes, including the introduction of novel genetic traits.

In certain embodiments of the invention the oncogene activity is repressed in a reversible fashion. Thus a combination of an oncogene and a repressor gene allows normal plant cell growth and development leading to plants with normal morphological characteristics. Separation of the two genetic constructs, for example via segregation or crossing over leads to de-repression and morphologically abnormal plants which can be easily discriminated. Thus the method may provide utility for maintaining certain genetic combinations.

In another embodiment of the invention, a gene encoding a novel trait is linked to the oncogene introduced in the first transformation step or linked to a repressor gene introduced in a second transformation event. In another embodiment of the invention, more than one gene encoding a novel trait is linked to the repressor and the oncogene, thus permitting a convenient means to assemble and maintain a variety of genetic traits in a single plant line. For example, a number of novel traits could be added individually to a cell line that is derived from a crown gall. Each of the novel traits would be linked to a repressor molecule that inhibits only one or two of the oncogenes present in the cell line. Morphologically normal plant cells could only form upon introduction of all of the required oncogene repressors linked to the various novel traits. In this fashion, simultaneous introduction of a predetermined number of novel traits would be a prerequisite for regeneration of morphologically normal plant cells. In this fashion multiple genes could be introduced into plant cells and recovery of plants containing all of the novel traits would be inherent in the system.

Thus a new utility for oncogenes and the T-DNA oncogenic region in the production of transgenic plants is derived. In particular, the method allows for the selection of plant cells first obtained by the natural ability of *Agrobacterium* to efficiently transfer DNA containing one or more active oncogenes or the entire oncogenic region, thus producing a population of plant cells containing oncogenes, which can grow under conditions insufficient for the growth of untransformed cells. Once these cells are established, a cell line useful for the introduction or any number of transgenes is derived.

The method then employs a second DNA transfer event which utilizes a genetic construct capable of inhibiting the activity of one or more of the oncogenes such that plant cells containing the second DNA are capable of regenerating into morphologically normal plants. Depending upon the particular plant and tissue culture methods employed, selection via the use of traditional toxic selection may or may not be used.

Certain aspects of the method also rely on the controlled expression of a DNA construct that permanently deletes the oncogenes to allow regeneration to take place. The DNA construct encoding the deletion function may be included in the initial construct or may be added to the plant cell via subsequent transformation event.

The oncogenes of the tumorigenic *Agrobacterium* strains have been extensively studied. Generally, there are two types of oncogenes on the *Agrobacterium* plasmid: the tmr oncogene and the tms oncogenes. The tmr oncogene (also known as the ipt gene) encodes an enzyme that synthesizes isopentyl-adenosine 5'-monophosphate, a cytokinin plant hormone that induces shoot formation in a suitable host. The oncogenes referred to as tms (comprising tms oncogene 1 and tms oncogene 2) encode enzymes responsible for auxin overproduction in suitable hosts, leading to the production of roots. When combined, the tms and tmr genes usually lead to the production of a form of crown galls on suitable hosts.

Some of the other oncogenes found within the T-DNA act as modifiers or potentiators of crown gall formation. Usually plant cells containing oncogenes contained within an intact T-DNA exhibit hormone-independent growth in culture. Said plant cells in culture usually are in a de-differentiated state, e.g. callus, said callus capable of growth without exogenous phytohormones. However, if oncogene function is inhibited, the plant cells are then able to differentiate into cells capable of regeneration under appropriate conditions, in some cases regeneration occurs upon the crown gall callus itself.

Although the combined activity of the tms and tmr genes may be sufficient for hormone independent growth, clearly the entire complement of oncogenes has been shown to be highly efficient in the formation of crown galls. Thus, for the most preferred and widely applicable aspects of the present invention, the entire complement of genes encoded within the T-DNA region is used rather than modification of the region to delete one or more oncogenes. This will include the other oncogenes within the T-DNA region including those specifying the synthesis of opines and other T-DNA encoded products.

The present method takes advantage of the fact that regeneration of normal plants from oncogene containing callus may require no additional manipulation other than elimination of oncogene activity. There is precedent for this in the art as "revertants", e.g. shoots or roots have been have been observed to form from oncogene containing callus in culture. Usually these structures are formed from cells that have lost the oncogene function through mutation. Indeed, U.S. Pat. No. 4,658,082 describes a method for the selection of such shooty revertants as a means of using in vivo infection of plant tissue to derive plants containing heterologous DNA. However, U.S. Pat. No. 4,658,082 does not contemplate the repression of oncogene function with a second transformation event nor does it allow one to conveniently recover plants that are morphologically normal. The methods described in U.S. Pat. No. 4,658,082 anticipate recovery of plants where the tumorogenic DNA (e.g. oncogenes) are randomly lost during culture or by mutation or other random events. This method does not allow efficient transformation nor does it allow for selection of plant cells that contain one or more oncogenes, the cells capable of regeneration to morphologically normal plants. The recovery of plants as described in U.S. Pat. No. 4,658,082 relies on the use of T-DNA conferring a shooty phenotype. The shoots are not morphologically normal.

In general, plants which contain one or more of the Ti oncogenes are phenotypically abnormal having crown gall tumors or curled and twisted leafs due to growth hormone imbalance. These abnormal plants are unsuitable for commercial applications. Accordingly, the art specifies modification of the *Agrobacterium* Ti plasmid in a variety of ways, typically by removal of the oncogenes, to become a tool for the introduction of DNA into plant cells. Generally, *Agrobacterial* transformation methods that have been used to date have used Ti plasmids in which the genes that result in the formation of cytokinins and auxins, other open reading frames within the T-DNA of unknown function and the genes for opine synthesis have been removed. Such plasmids are generally referred to as being "dis-armed". Accordingly, an "armed" Ti plasmid is generally considered to contain a gene normally found within the T-DNA or a gene called an oncogene. The present invention contemplates the use of "armed" plant vectors.

Because the first step in the process is the transformation of plants by the highly efficient process of natural crown gall formation, the present method also finds utility for the transformation of other crop species that are difficult to transform by conventional means using dis-armed plasmids and selection. These crops include sunflower, cotton, soybean, safflower, for example. As a result, the method allows for the formation of a population of cells essentially completely transformed and these cells can then be induced to delete or inactivate the oncogenic activity of the T-DNA region, making regeneration possible without application of selection. This method provides a convenient means to recover a morphologically normal transgenic plant from any crop species capable of being transformed by wild-type *Agrobacterium*. The ability to generate plant cells free of selectable markers is of great value to the industry.

In particular, the invention finds utility for transformation of a wide range of species including: *Brassica oleracea* species such as broccoli, cabbage, cauliflower, kale, Chinese kale, collard, and kohlrabi; *Brassica rapa* species including Chinese cabbage, pak choi, and turnip. The invention also finds utility for transformation of other vegetable crops such as: Tomato (*Lycopersicon esculentum*), *Cucumis* spp., including *C. melo* (melon) and *C. sativus* (cucumber), *Cucurbita* spp. (squash), including *C. maxima* and *C. pepo*, Spinach (*Spinacia oleracea*), Carrot (*Daucus carota*) Peppers including *Capsicum* spp. (pepper), including *C. annuum, C. frutescens,* and *C. chinense,* onions such as *Allium* spp. (onion), including *A. cepa* (bulb onion) and *A. fistulosum* (bunching onion), Radish (*Raphanus sativus*), Watermelon (*Citrullus lanatus*), and Lettuce (*Lactuca sativa*). The invention also finds utility for transformation of onamental species such as Impatiens, Pansy (*Viola×wittrockiana*) and Lisianthus (*Eustoma grandiflorum*).

The present method differs from the art in many ways. The present invention does not require the construction of a vector where the oncogenic region of the T-DNA is deleted from within the Ti-plasmid. The present method also allows for the use of the natural form of the Ti-plasmid rather than the use of a binary or co-integrate type plasmids. The present invention may utilize the entire natural DNA transfer process and in the most elemental embodiment comprises the entire oncogenic region of the Ti-plasmid and the wild-type T-DNA that carries all of the genes required for tumor formation, not just one (e.g. the cytokinin biosynthesis gene as described by Ebinuma et al, ibid). Whole plants, plant explants or plant cells can be conveniently transformed with armed *Agrobacterium* strains. In the present invention cells may be selected on the basis of tumor formation and growth on hormone free media, plants can not regenerate from transformed cells until the tumor forming genes are eliminated or their activity inhibited. In the art, the use of certain oncogenes, e.g., the oncogene 4, is used as a visual marker for transformed cells, as transformed cells form morphologically abnormal shoots. In the present method, transformed cells are unable to undergo any differentiation and are first identified by the formation of undifferentiated tissue (e.g. crown gall). In the present method, normal plants are regenerated in a single step from this tissue by elimination of the activity of the tumor forming genes, without the need for a selectable marker.

Thus, in one embodiment, the present invention combines the natural T-DNA transfer process, the known activity of the oncogenic T-DNA region and the ability to conveniently identify crown gall tissue with new techniques in molecular biology to derive a novel transformation process that incorporates the efficiencies of the natural process with techniques that allow for the convenient transformation and recovery of morphologically normal plants from many different plant species.

The transformed plants produced in this fashion will have stably inserted into their genome a DNA region composed of a right and left T-DNA border flanking a novel DNA sequence heterologous to plant cells and at least a portion of an oncogene from the oncogenic region of a Ti-plasmid. In some instances the entire complement of oncogenes normally found in the T-DNA will be present. In other embodiments only a portion of an oncogene will remain. Thus plants produced may at least contain oncogenic regions from the T-DNA but will be capable of normal growth and exhibit normal morphology. These plants are capable of transferring the inserted DNA through normal reproductive methods to progeny and can produce seed containing the inserted DNA. The sexual transfer of the inserted DNA allows for introduction of the inserted DNA into other sexually compatible plant species or varieties.

The following examples serve to illustrate the method and in no way limit the scope of the invention.

EXAMPLE 1

The construction of a modified wild-type *Agrobacterium* Ti-plasmid is described in the following examples. This example describes the construction of a vector for the introduction of a recombinase site into the right border region of the Ti-plasmid from the wild-type C-58 nopaline *Agrobacterium*.

The modification of the Ti-plasmid is carried out by the construction of a vector comprising a recombinase site and regions of homology that permit the introduction of the site by homologous recombination within the *Agrobacterium* strain. In this example, the vector used in the construction of a wild-type C-58 Ti-plasmid modified to contain, at the right border region, DNA sequences recognized by a site-specific recombinase.

Figure 21:
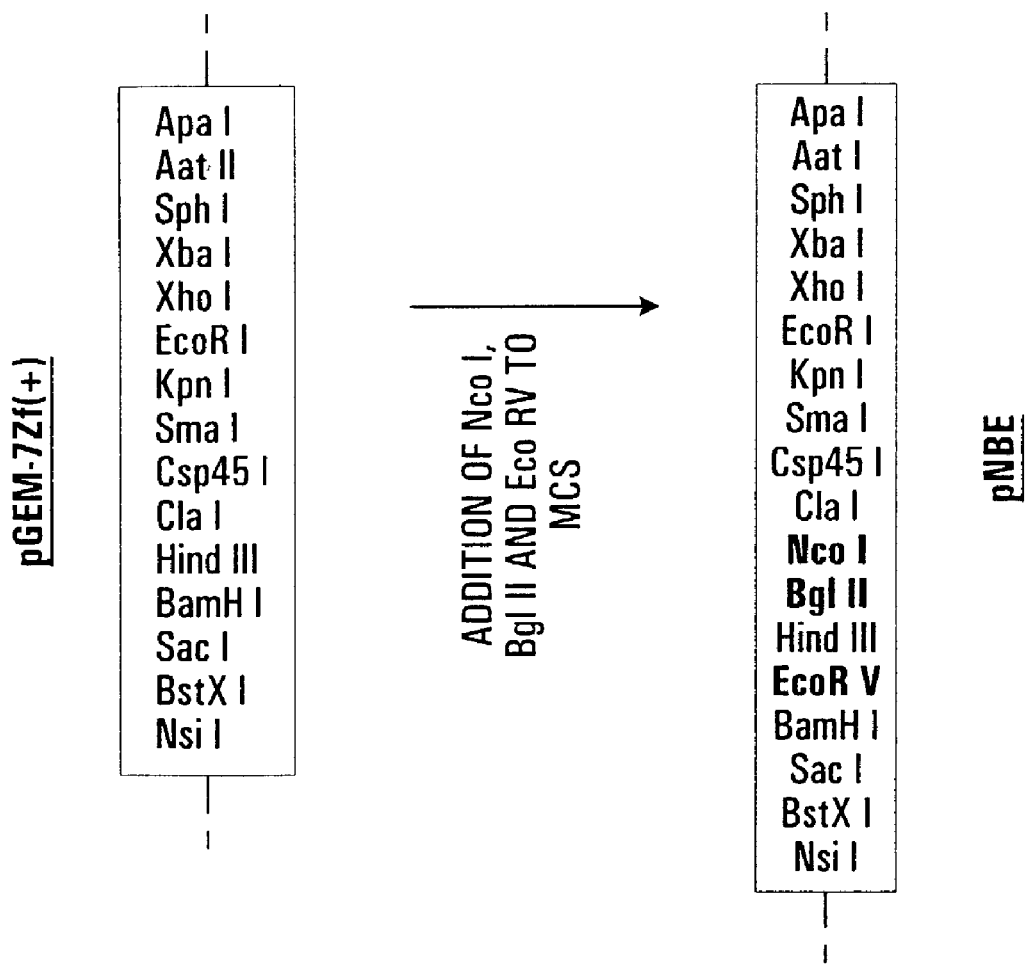
FIG. 21 provides restriction maps and a representation of the modified pGEM7Zf(+) vector used to construct the modified Ti-plasmids.
Figure 28:
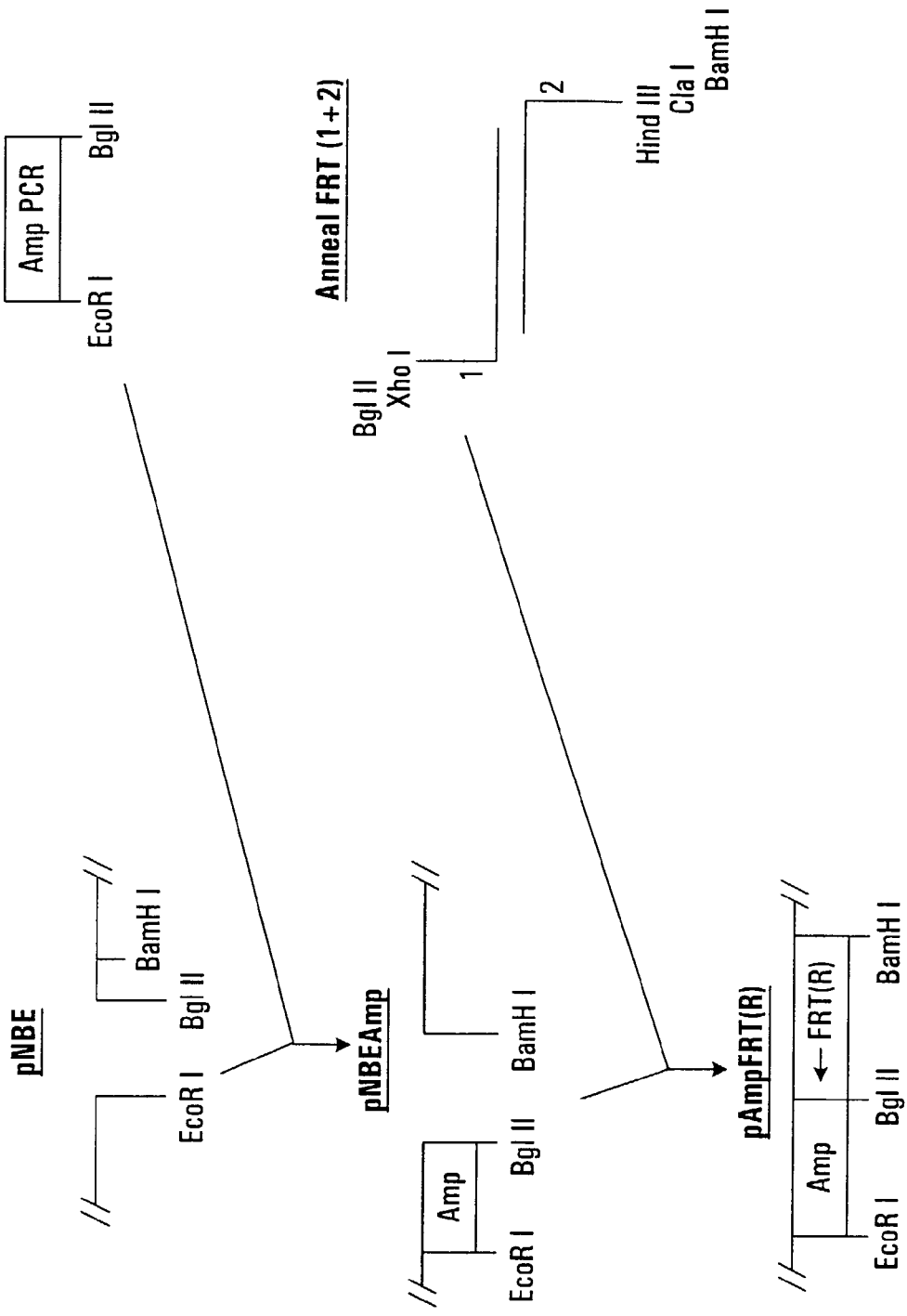
FIG. 28 illustrates the steps used to construct one of the intermediate vectors (pAmpFRT(R)) used for the modification of the right border region of the T-DNA of the C58 Ti-plasmid.
Figure 29:
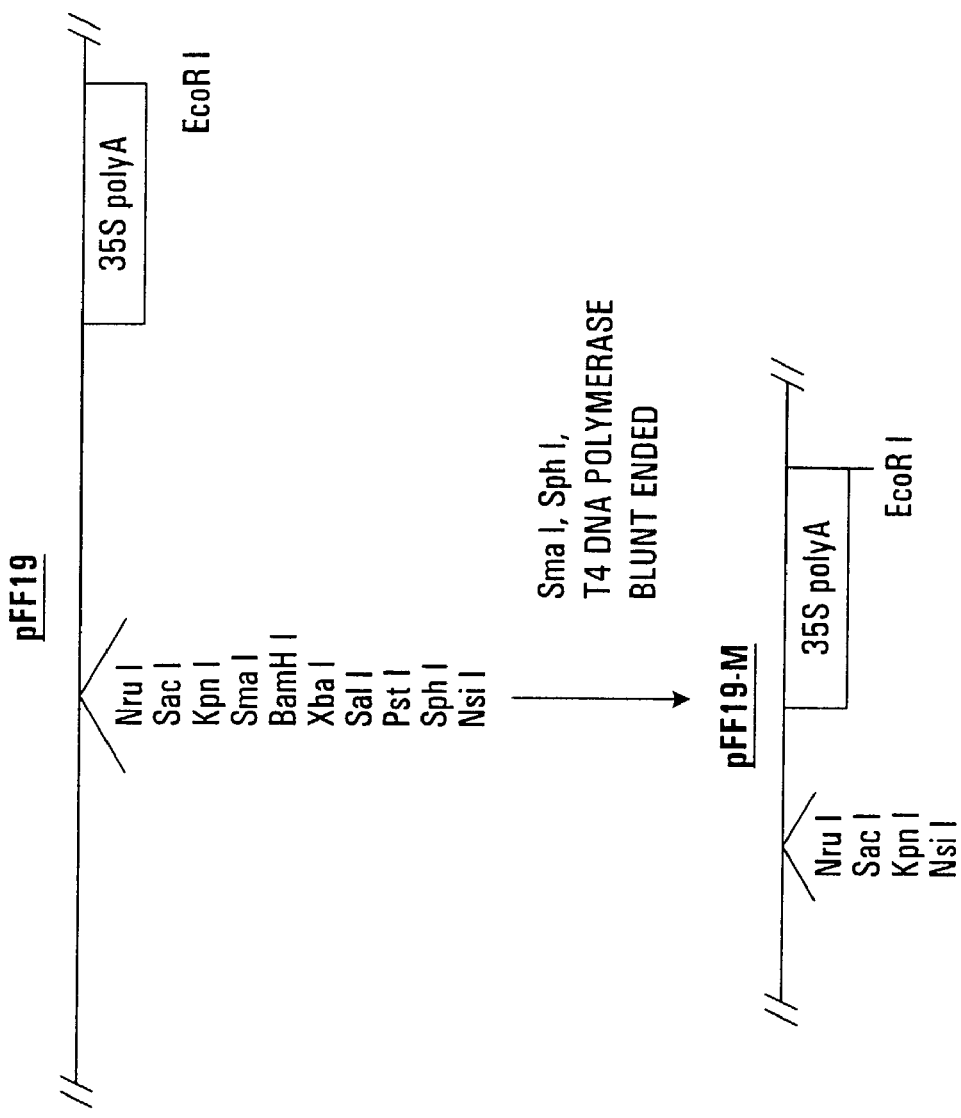
FIG. 29 illustrates the steps used to construct one of the intermediate vectors used for the modification of the right border region of the T-DNA of the C58 Ti-plasmid (construction of a 35S polyadenylation signal).

To modify the Ti-plasmid, a vector named pRBC-1 (Right Border Construct) was constructed for the homologous recombination with a wild-type C-58 Ti-plasmid. A number of cloning steps were employed. The steps employed are outlined in FIGS. 28–33. These steps involved the assembly of various DNA components as follows:

The common plasmid vector pGEM-7Zf(+) (Promega, Madison, Wis., USA) was modified by addition of Nco I, Bgl II and Eco RV sites to the multiple cloning site as outlined in FIG. 21 to produce pNBE. The ampicillin resistance gene was isolated from pBR322 using PCR primers (Seq ID Nos 25 and 26) The ampicillin gene (Seq ID No 11) was added to pNBE as shown in FIG. 28. The resultant plasmid was called pNBEAmp.

The FRT recombinase recognition sites were added to pNBEAmp by annealing two single stranded DNAs (Seg. ID Nos 29 and 30), and the resultant annealed double-stranded DNA was inserted into pNBEAmp to derive pAmpFRT(R) as shown in FIG. 28.

Figure 12:
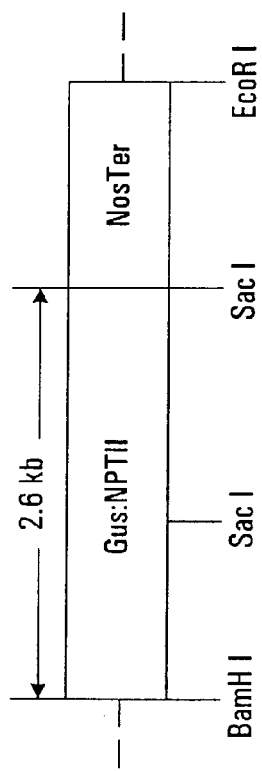
FIG. 12 provides a restriction map and a representation of the GUS:NPTII fusion DNA sequences used to construct the modified Ti-plasmids.
Figure 15:
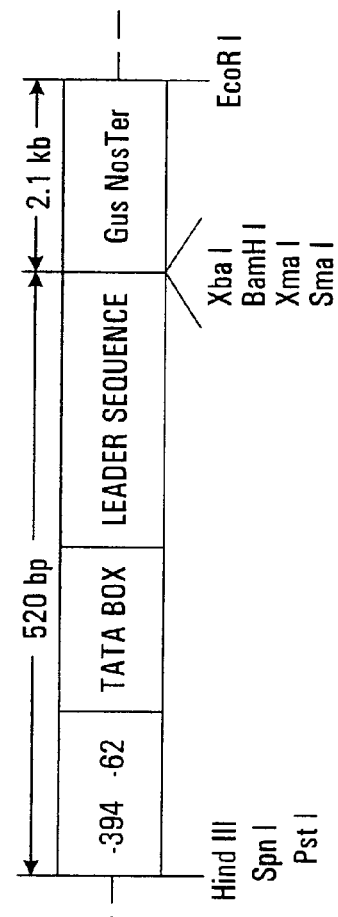
FIG. 15 provides a restriction map and a representation of the constitutive "EntCUP2" promoter DNA sequence used to construct the modified Ti-plasmids.
Figure 13:
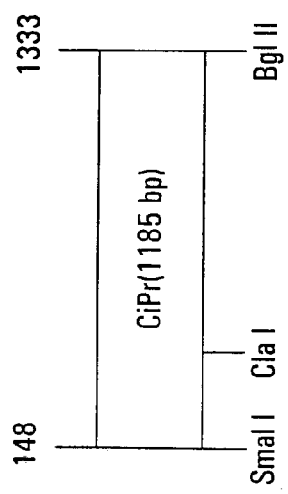
FIG. 13 provides a restriction map and a representation of the cold inducible promoter DNA sequence used to construct the modified Ti-plasmids.
Figure 17:
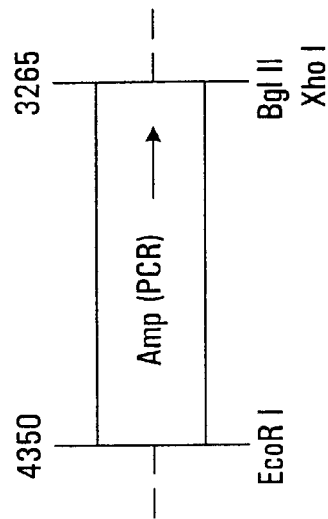
FIG. 17 provides a restriction map and a representation of the ampicillin bacterial marker DNA sequences used to construct the modified Ti-plasmids.

In addition to pAmpFRT(R) a number of other DNA components were isolated. A 35S polyadenylation signal (Seq ID No 10) was constructed from the plasmid pFF19 (Timmermans et. Al., J. Biotech 14:333–344, 1990) as outlined in FIG. 29 by the modification of pFF19 to form pFF19M by the elimination of the Sma I-Sph I region of the polylinker as shown. In addition, a visible marker gene was included for convenience of monitoring the transformation process. The visible marker gene, which is optional for this construct, comprised the GUS-NPTII fusion from the plasmid pGKK14, (Seq ID No. 8; Datla, R. S. S., Hammerlindl, J. K., Pelcher, L. E., Crosby, W. L., and G. Selvaraj, 1991, Gene 101: 239–246) kindly provided by Dr. Gopalan Selvaraj, Plant Biotechnology Institute, National Research Council of Canada, Saskatoon, Saskatchewan. The map of the gene is provided in FIG. 12.

Figure 30:
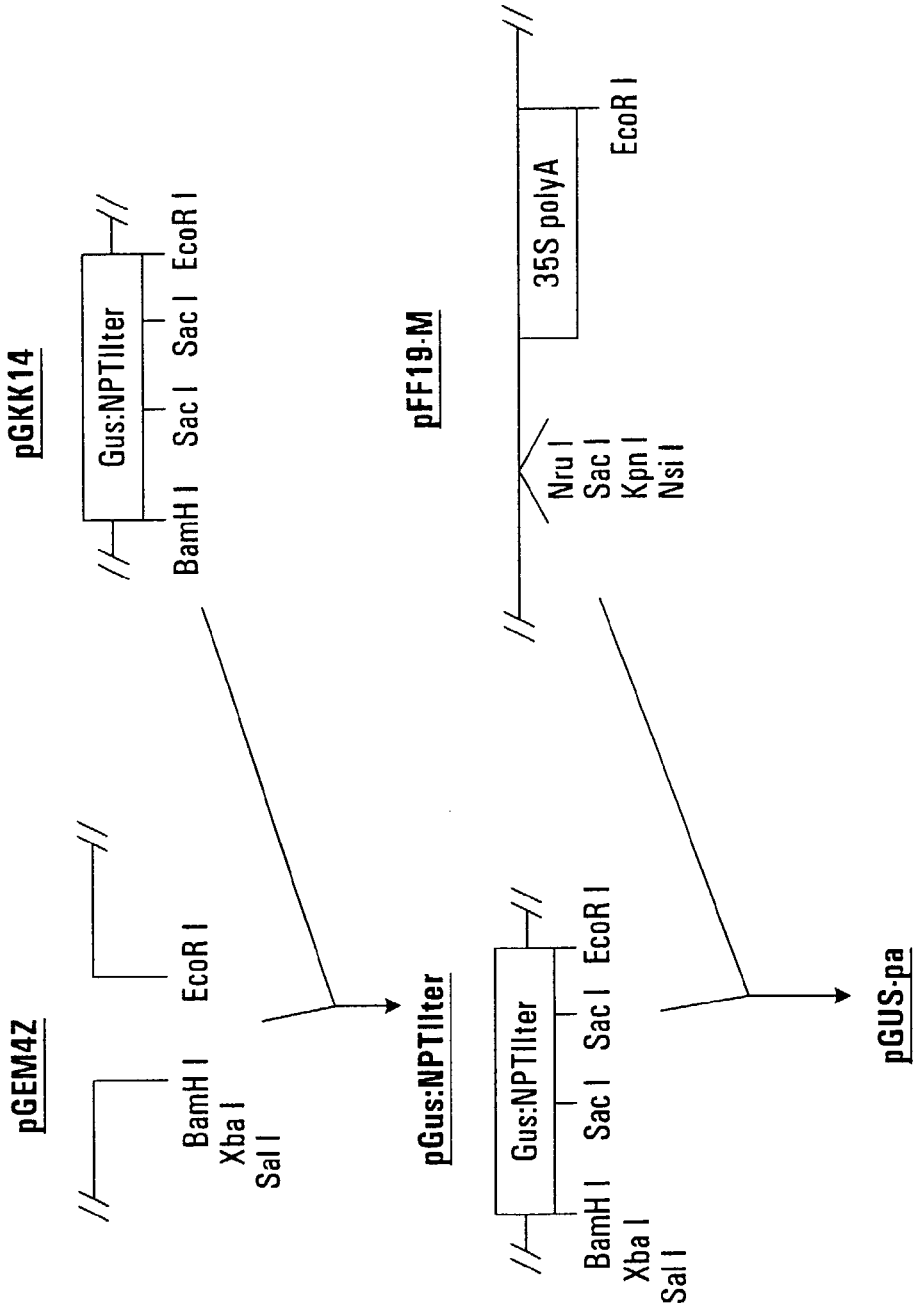
FIG. 30 illustrates the steps used to construct one of the intermediate vectors (pGUS-pA) used for the modification of the right border region of the T-DNA of the C58 Ti-plasmid.
Figure 31:
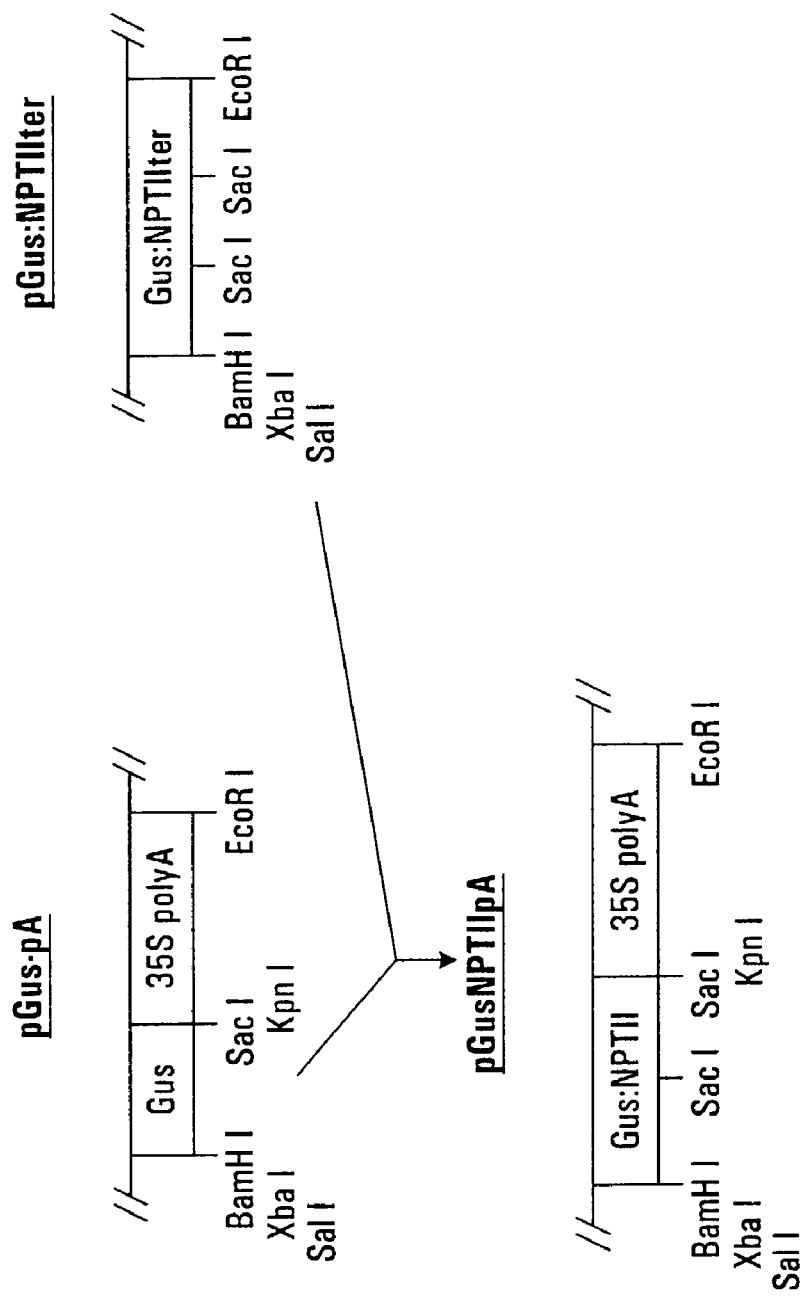
FIG. 31 illustrates the steps used to construct one of the intermediate vectors (pGUSNPTIIpA) used for the modification of the right border region of the T-DNA of the C58 Ti-plasmid.

The GUS-NPTII fusion gene was cloned into pGEM4Z as described in FIG. 30, using the Bam HI and Eco RI sites to form the plasmid called pGus:NPTIIter. The plasmid was digested with Sac I and Eco RI and the polyadenylation signal from pFF19-M was added as a Sac I-Eco RI fragment. This produced the plasmid pGUS-pA, which comprises the GUS gene and the 35S polyadenylation signal. This sequence of manipulations is described in FIG. 30.

Figure 32:
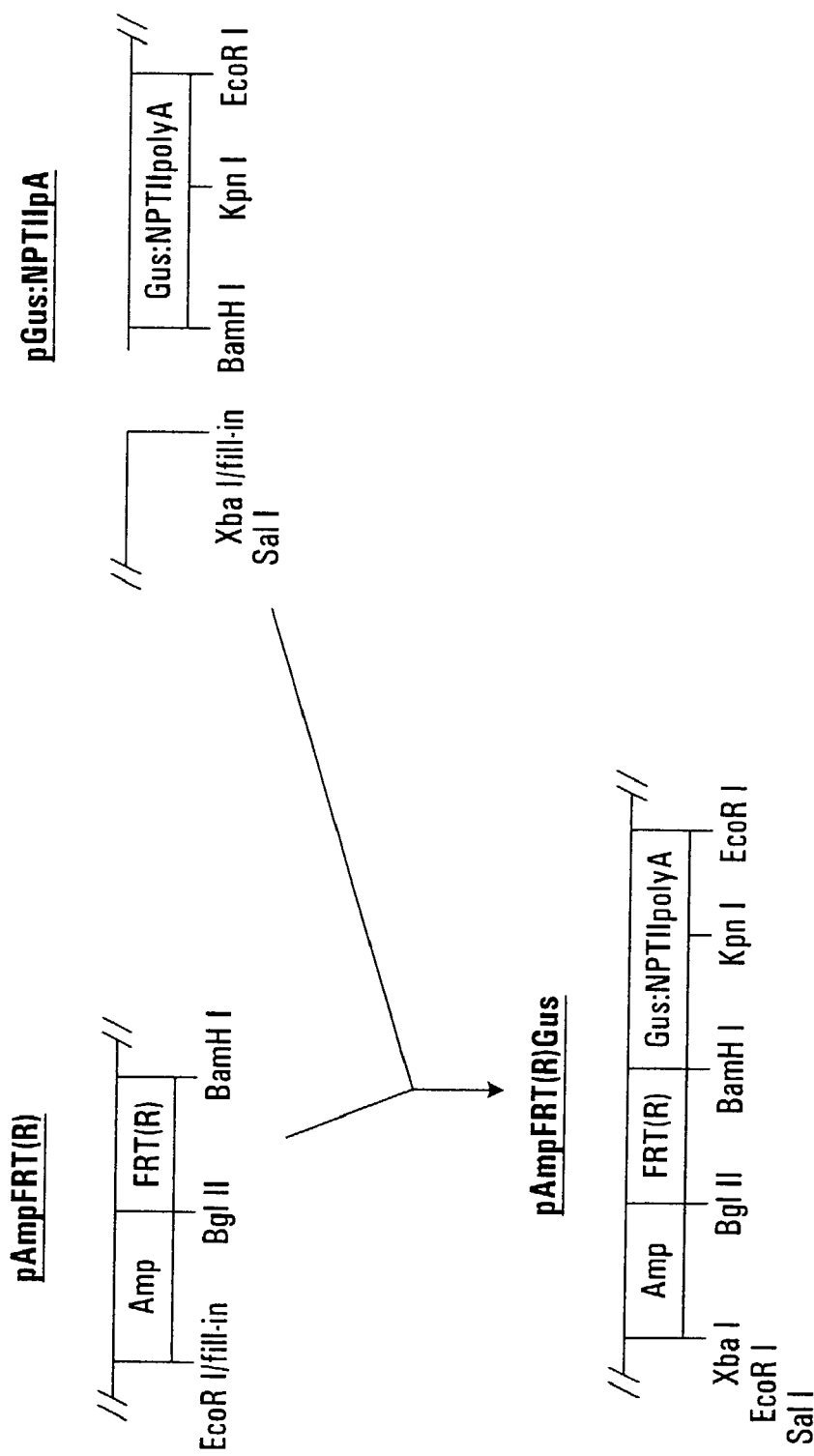
FIG. 32 illustrates the steps used to construct one of the intermediate vectors (pAMPFRT(R)Gus) used for the modification of the right border region of the T-DNA of the C58 Ti-plasmid.

The next series of manipulations involved the recombination of the GUS and NPTII gene in pGUS-pA by digesting pGUS-pA with Sac I and adding the Sac I fragment from pGUS:NPTIIter to derive the plasmid pGusNPTIIpA. To the plasmid pGusNPTIIpA was added the ampicillin gene linked to the FRT sites from the plasmid pAmpFRT(R) as shown in FIG. 32. This produced the vector pAmpFRT(R)Gus, shown in FIG. 32.

Figure 22:
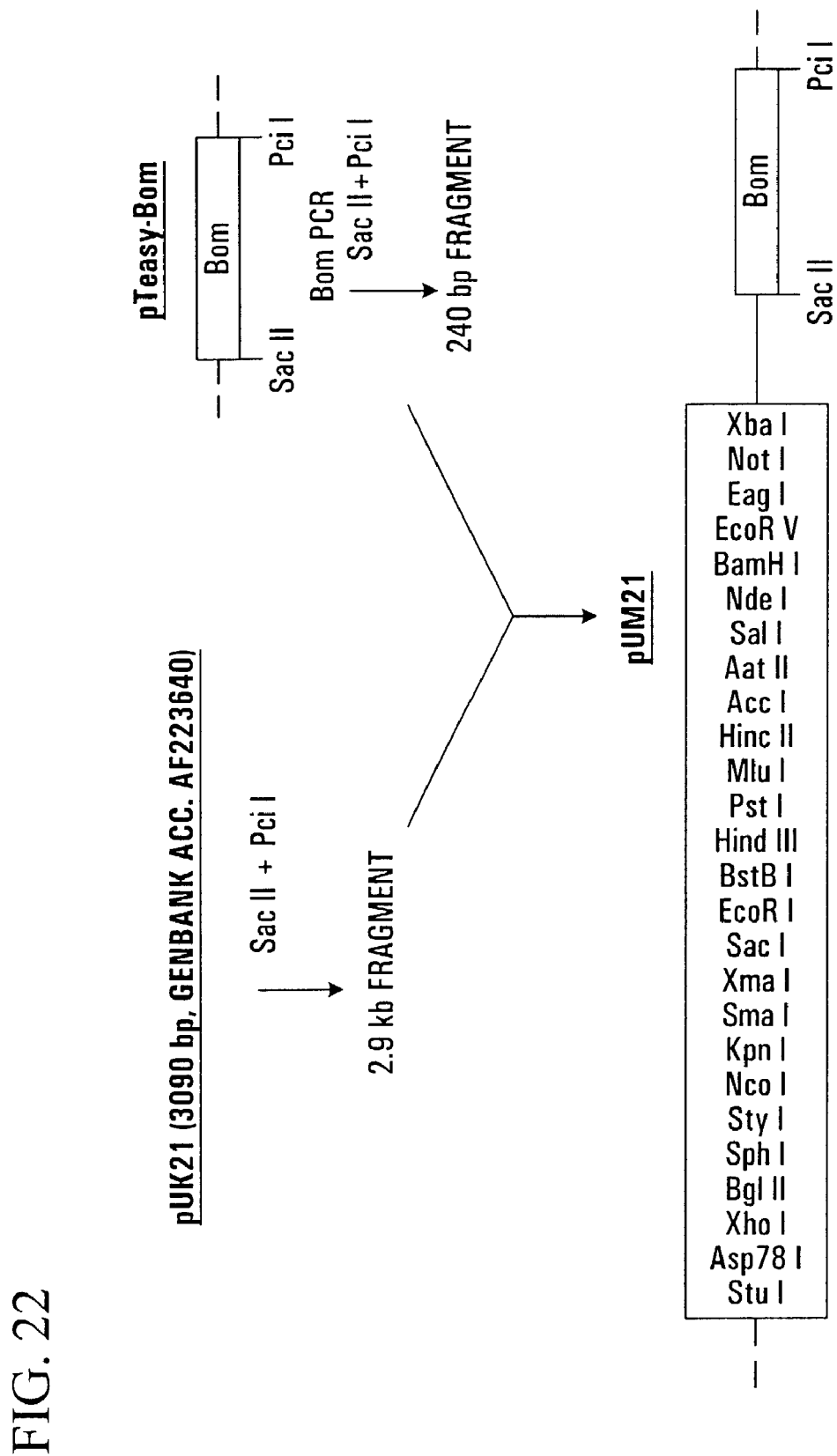
FIG. 22 provides restriction maps and depicts construction of the pUM21 vector used to construct the modified Ti-plasmids.

To accomplish the assembly of the final vector used for homologous recombination with the Ti-plasmid, a number of other components were used. The first is the vector pUM21, derived from pUK21 (GenBank acc. AF223640) by addition of the basis of mobilization site from a derivative of pBR322 (pTeasy, Promega, Madison, Wis., USA) using PCR primers (Seq ID Nos. 13 & 14) to derive a Sac II-Pci I fragment (Seq ID No 12) that was cloned as shown in FIG. 22. The resulting plasmid pUM21 has the pBR322 mobilization sequence.

Figure 33:
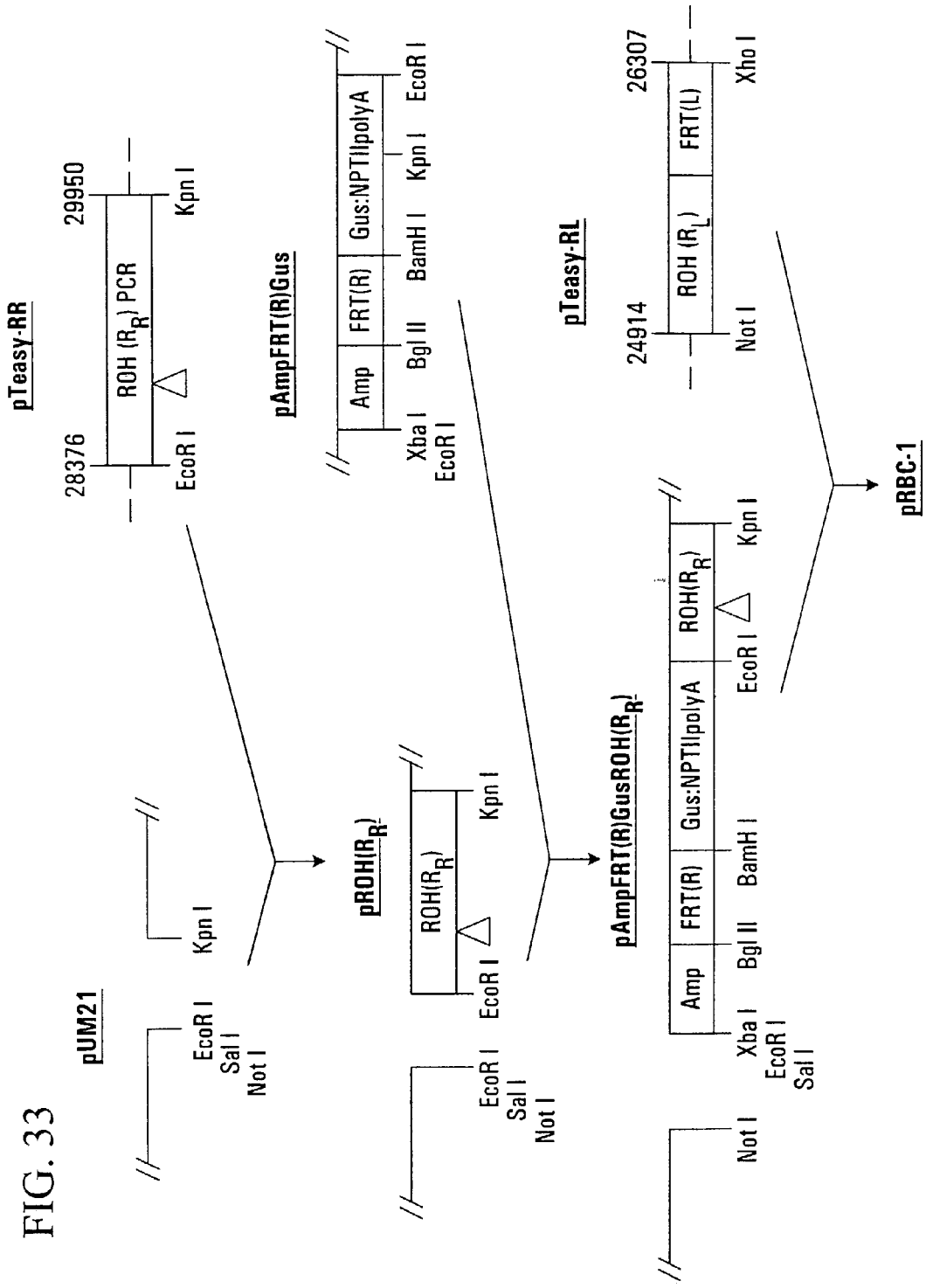
FIG. 33 illustrates the steps used to construct one of the intermediate vectors used for the modification of the right border region of the T-DNA of the C58 Ti-plasmid (final derivation of pRBC-1).

A region of homology (ROH) from the right region of the right border (ROH $R_R$) (Seq ID No 3) was isolated by PCR using the primers specified in Seq ID Nos. 17 & 18, and this fragment was cloned as a Eco RI-Kpn I fragment in pUM21 to derive PROH($R_R$) as shown in FIG. 33.

The plasmid pROH($R_R$) was digested with Eco RI and the Eco RI fragment of pAmpFRT(R)Gus was added to derive pAmpFRT(R)GusROH($R_R$). This plasmid was digested with Not I and Sal I and the Not I-Xho I fragment from pTeasy-RL was added. This fragment is derived from PCR amplification of the left region of the region of homology from the right border to the T-DNA from the Ti-plasmid in the Agrobacterium strain C58 (Seq ID No 4) and was isolated by PCR amplification with two primers (Seq ID Nos. 19 & 20) followed by digestion with Not I and Xho I. The fragment in pTeasy-RL has in addition to the region of homology, a FRT recombinase recognition site. The combination of the pTeasy-RL fragment inserted into pAmpFRT(R)GusROH ($R_R$) leads to the formation of pRBC-1 as detailed in the steps outlined in FIG. 33.

Figure 34:
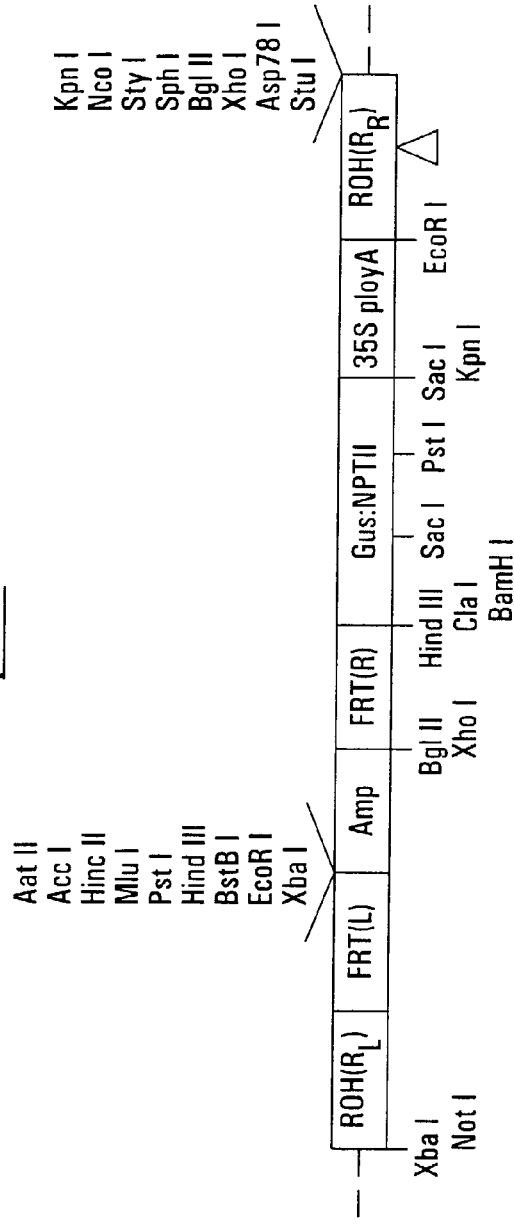
FIG. 34 depicts a detailed restriction map of the homologous recombination plasmid pRBC-1 designed for the insertion of a recombinase sequence into the Right border region of the T-DNA of the C58 nopaline Ti-plasmid. The plasmid contains, two flanking regions of homology and located between those regions are two recombinase recognition site (FRT) flanking an ampicillin resistance gene for selection of the homologous recombination event as well as a "promoterless" GUS-NPTII fusion gene that can be activated upon recombination within the modified Ti-plasmid.

The vector pRBC-1 comprises, in the 5'-3' direction, the following components: a DNA sequence representing the left portion of the region of homology for the right border of the T-DNA region of the Ti-plasmid from the *Agrobacterium* strain C58, a FRT recombinase recognition site, an ampicillin marker gene; a second FRT site, a promoter-less GUS-NPTII gene, a 35S polyadenylation signal, a region of DNA representing the right region of the region of homology from the right border of the T-DNA region of the Ti-plasmid from the *Agrobacterium* strain C58. The detailed restriction map is shown in FIG. 34.

EXAMPLE 2

This example describes the introduction of the plasmid pRBC-1 into C58 *Agrobacterium*.

In this example, the pRBC-1 vector as used to insert a sequence into the Ti-plasmid of the strain C58 by a combination of triparental mating (Rogers et al., Methods Enzymology 118:627–636, 1986) and homologous recombination. In this example, pRBC-1 in the *E. coli* strain DH5FT was combined with *Agrobacterium* C58 and a *E. coli* helper strain HB101 carrying the wide host range plasmid pRK 2013. Cells are plated on minimal media and the *Agrobacterium* is selected for resistance to the antibiotic carbinicillin, a structurally related analog of ampicillin and rifampicin as well as sensitivity to kanamycin.

*Agrobacterium* cells resistant to the appropriate antibiotics are selected and the integrity of the inserted DNA at the right border region is confirmed by PCR and restriction digest analysis. The resultant vector comprises a wild-type C-58 Ti-plasmid modified to contain a DNA sequence recognized by a site-specific recombinase at the right border of the T-DNA, (and optionally a marker coding region). The inserted DNA also contains an ampicillin resistance gene flanked by two FRT sites.

To remove the resistance gene, the FLP recombinase gene is expressed in trans to eliminate the ampicillin gene. To accomplish this, the FLP recombinase gene is modified to remove the intron found in the plasmid vector pOG44, and the gene is placed under the control of a bacterial promoter such as that found in the vector pLEX (Invitrogen, www-.invitrogen.com) as a Bgl II-Xho I fragment og POG44 into the Bam HI-Xho I region of the pLEX plasmid.

The plasmid is then introduced into *Agrobacterium* by triparental mating as described above, or alternatively by direct DNA transfection, and the cells are plated on minimal media without antibiotics. Alternatively, the pOG44 vector can be used directly since the typical "leakage" of eukaryotic coding sequences in bacterial cells may be sufficient to provide a level of recombinase protein capable of causing excision of the amp marker. The preferred method is to have the recombinase coding sequence under the control of an inducible bacterial promoter.

The cells are then replica plated on ampicillin containing media and cells are chosen that are ampicillin sensitive. The arrangement of DNA as a result of the activity of the FLP recombinase is verified by a combination of restriction mapping and PCR analysis. The plasmid containing the recombinase gene is lost since it is unable to be maintained in *Agrobacterium*. The modified Ti-plasmid is referred to as pTI-C58 RBC-1.

The resultant *Agrobacterium* strain is called C58 RBC-1 and carries a nopaline Ti-plasmid modified to contain a FRT recombinase recognition site at the right border region of the T-DNA.

EXAMPLE 3

This example demonstrates use of the strain C58 RBC-1 to produce transformed plant cells.

The C58 RBC-1 strain of *Agrobacterium* is used to form tumors on inoculated plants to demonstrate that the modification does not inhibit the oncogenic activity of the Ti-plasmid.

To form tumors, sterile seedlings of various *Brassica* (*napus, rapa, oleracea* and *carinata*) species and tobacco are inoculated with an overnight cultures of the *Agrobacterium* strains C58 and C58 RBC-1 by wounding the stem with a sterile needle containing the *Agrobacterium*. Tumor formation is scored and no difference is observed between the rate of tumor formation with the wild-type and the C58 strain with a modified right border.

EXAMPLE 4

This example illustrates construction of a vector for the introduction of a recombinase site in the left border region of the Ti-plasmid from the wild-type C-58 nopaline *Agrobacterium*.

In this example, the construction of a vector to introduce a second recombinase recognition site into a C-58 Ti-plasmid (pTi-C58 RBC-1) modified to contain, at the right border regions, DNA sequences recognized by a site-specific recombinase. In addition to the recombinase recognition sequence, addition DNA sequences are introduced that include a recombinase encoding gene, modified for expression in plant cells, under the control of an inducible promoter. The vector used to introduce the sequences into the left border region of the Ti-plasmid also comprises a series of unique restriction sites convenient for the introduction of a gene encoding a novel trait into the Ti-plasmid along with the recombinase site. The vector is called pLBC-1 (Left Border Construct), is capable of acting as a "shuttle vector" for the introduction of genes encoding novel traits and its assembly is detailed below.

Figure 20:
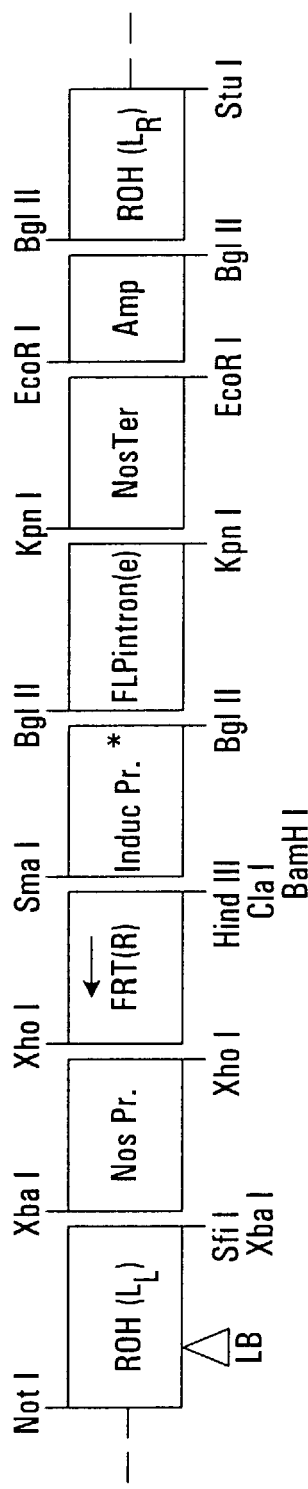
FIG. 20 provides a simplified restriction map and a representation of the components used to derive the homologous recombination plasmid pLBC-1 for insertion of a recombinase sequence into the Left border region of the T-DNA of the C58 nopaline Ti-plasmid.

The pLBC-1 vector was constructed for introduction of the recombinase region via homologous recombination with the pTi-C58 RBC-1 Ti-plasmid, with the region of homology being targeted to the left border region. A number of cloning steps were employed. The steps are outlined in FIGS. 23–26. These steps involved the assembly of various DNA components as follows:

In this assembly of the DNA components detailed herein, the "shuttle vector" pLBC-1 is used to introduce the specific DNA sequence (FRT) recognized by the recombinase into the modified Ti-plasmid pTiC58 RBC-1. pLBC-1 comprises: a region of homology with the left border region of the Ti-plasmid (ROH($L_L$) (Seq ID No. 1), a plant expressible promoter (NosPr) (Seq ID No. 7), a recombinase recognition sequence (FRT), a multiple cloning site, an inducible promoter (CiPr) (Seq ID No. 9), a modified FLP recombinase gene containing a plant intron (FLoP), a polyadenylation signal (NosTer), an ampicillin resistance gene (Amp) (Seq ID No. 11), and a region of homology with the right hand-side of the left border region of the C-58 plasmid (ROH($L_R$) (Seq ID No. 2). The arrangement of these components are shown in FIG. 20.

Figure 10A:
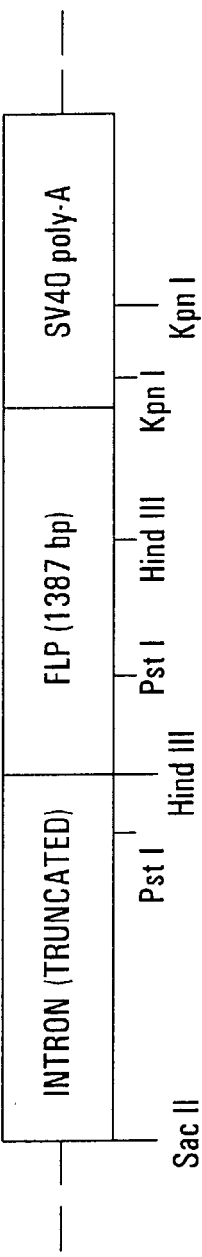
FIGS. 10A–10C provide restriction maps and a representation of the modified FLP recombinase DNA sequences used to construct the modified Ti-plasmids.
Figure 10B:
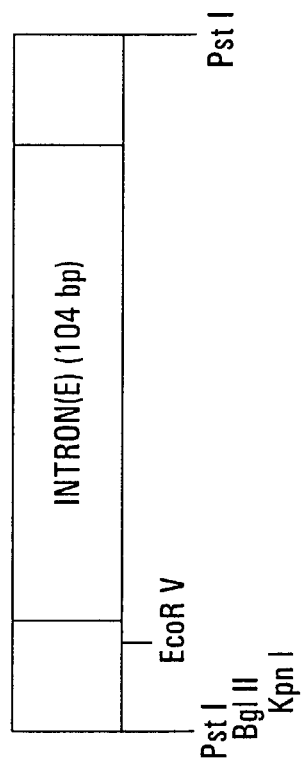
Figure 10C:
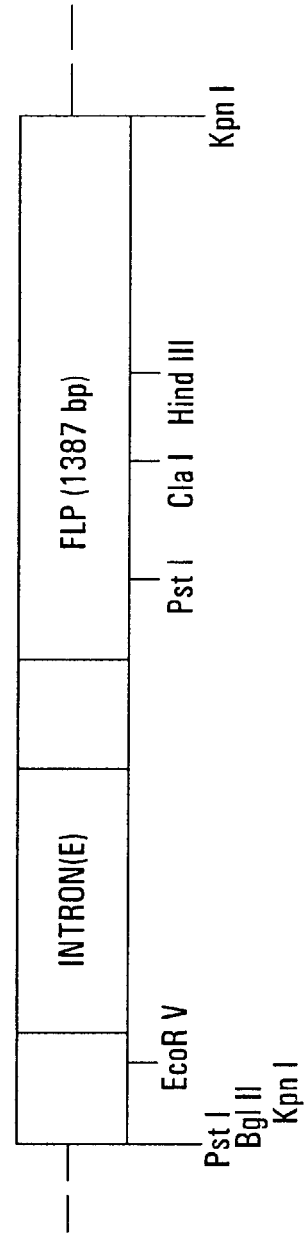
Figure 23:
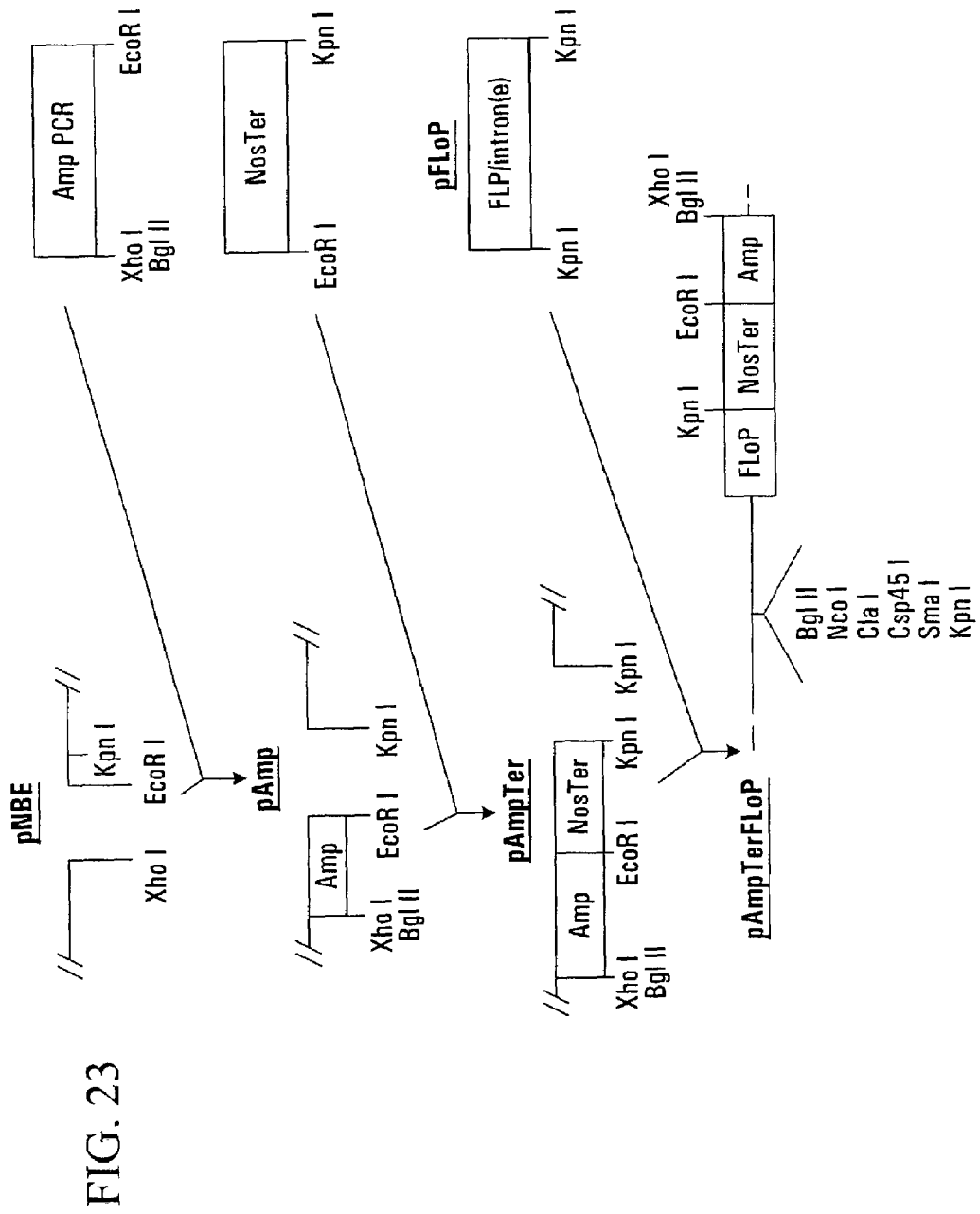
FIG. 23 illustrates the steps used to construct one of the intermediate vectors used for the modification of the left border region of the T-DNA of the C58 Ti-plasmid and construction of the intermediate vector pAmpTerFloP.

To assemble these components, the following steps were employed: The plasmid pNBE was used to clone the Amp resistance gene to derive the plasmid pAmp. The plasmid pAmp was digested with Eco RI and Kpn I and the NosTer fragment was added to derive pAmpTer (FIG. 23). This plasmid was then digested with Kpn I and the modified pFLop recombinase gene was added as a Kpn I fragment. The pFLoP gene was constructed as shown in FIG. 10. In this figure, the FLP recombinase was modified to contain a *Arabidopsis* eEF-1B intron (Gidekel et al., Gene 170:201–206, 1996), referred to as intron (e), by the insertion of a synthetic intron sequence (Seq ID No 6.) into the Pst I site of the FLP recombinase (Seq ID No 5.) to derive a plant expressible FLP recombinase with a plant intron, said intron containing multiple stop signals to eliminate expression in bacterial hosts through read-trough expression. The plasmid that incorporates the Amp, NosTer and pFLoP gene is called pAmpTerFLoP and is shown in FIG. 23.

Figure 24:
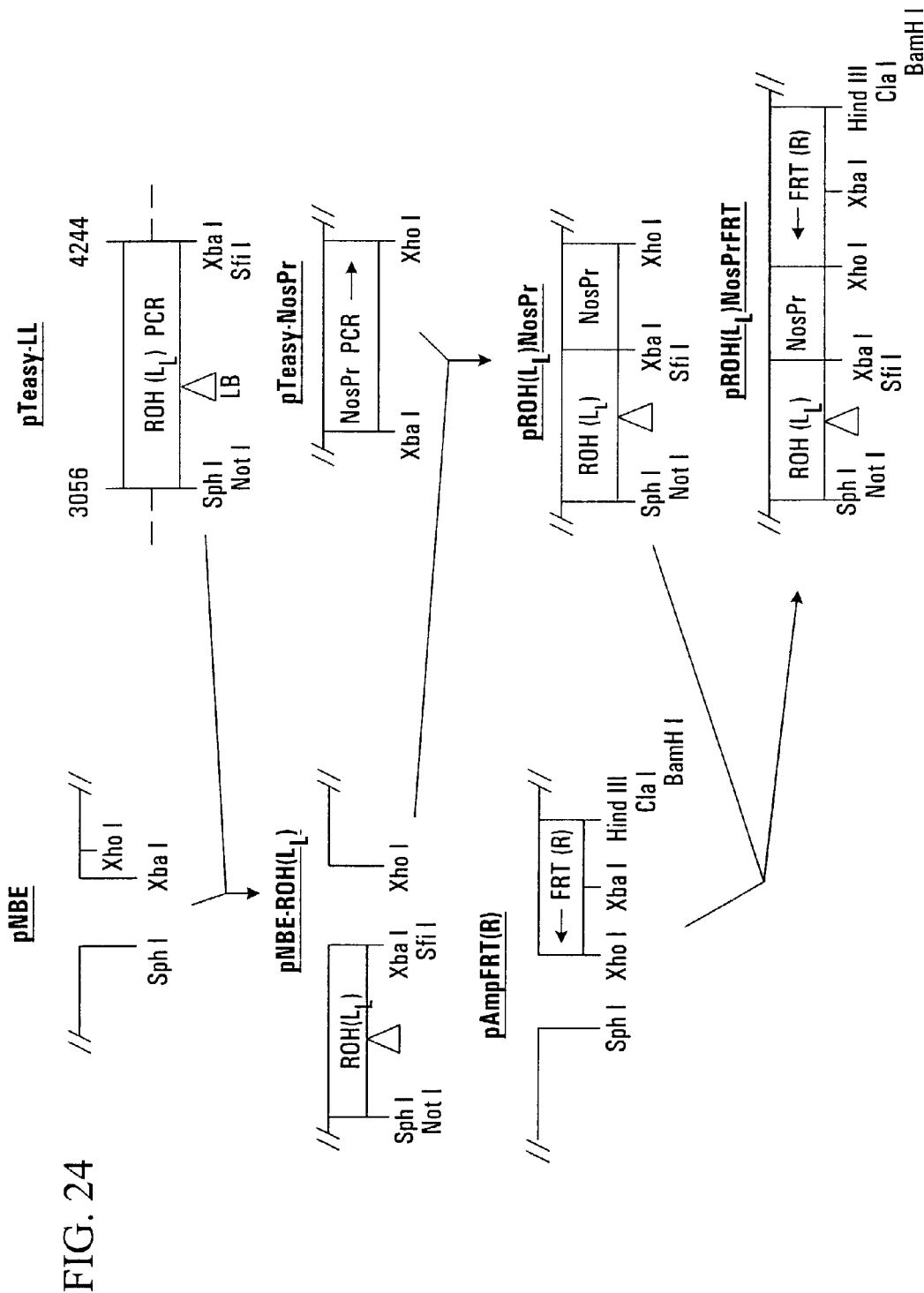
FIG. 24 illustrates the steps used to construct one of the intermediate vectors (pROH($L_L$)NosPrFRT) used for the modification of the left border region of the T-DNA of the C58 Ti-plasmid.

Another intermediate vector for the construction of pLBC-1 was constructed as outlined in FIG. 24. In this series of steps, the vector pNBE is digested with Sph I and Xba I and the Sph I-Xba I fragment of pTeasy-LL is added. PTeasy-LL is a vector that was derived by cloning the PCR product representing the left hand-side of the left border region of homology using the PCR primers described in Seq ID Nos. 21 & 22. The plasmid that incorporates the pTeasy-LL fragment and the pNBE vector is called pNBE-ROH ($L_L$).

Figure 11A:
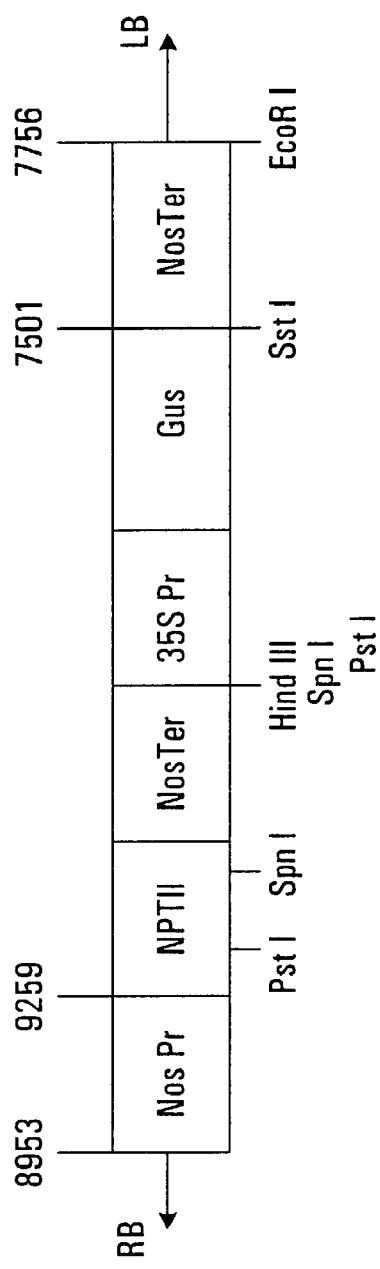
FIGS. 11A–11B provide restriction maps and a representation of the source (11A, pBin19) of the modified NOS promoter DNA sequence (PCR product, 11B) used to construct the modified Ti-plasmids.
Figure 11B:
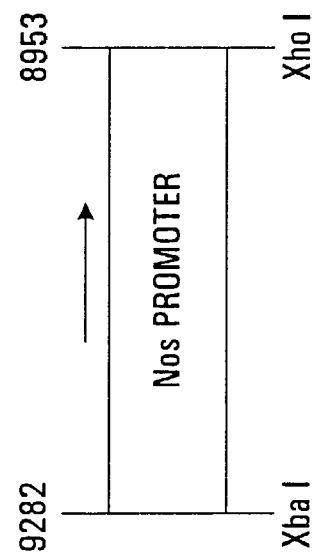
Figure 14:
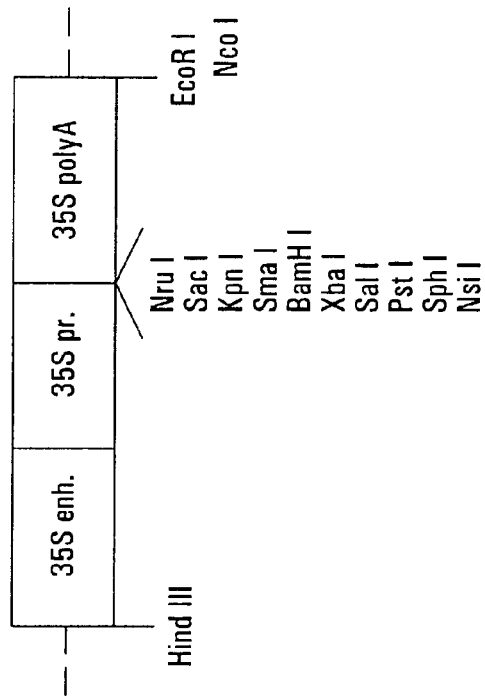
FIG. 14 provides a restriction map and a representation of the CaMV 35S DNA sequences used to construct the modified Ti-plasmids.

To pNBE-ROH($L_L$) was added the Nos promoter as a Xba I-Xho I fragment to derive pROH($L_L$)NosPro. The Nos promoter was isolated by PCR amplification as shown in FIG. 11, using the primers Seq ID Nos 15 & 16.

pROH($L_L$)NosPro was digested with Sph I and Xho I and cloned into pAmpFRT(R) to derive pROH($L_L$)NosPrFRT as shown in FIG. 24. The plasmid pAmpFRT(R) was derived as shown in FIG. 28. To construct pAmpFRT(R), PNBE and the Amp resistance gene were used to construct pNBEAmp. This plasmid was digested with Bgl II and Bam HI and a synthetic double stranded DNA comprising the FRT sites (Seq ID Nos 29 & 30) was added to derive pAmpFRT(R).

Figure 25:
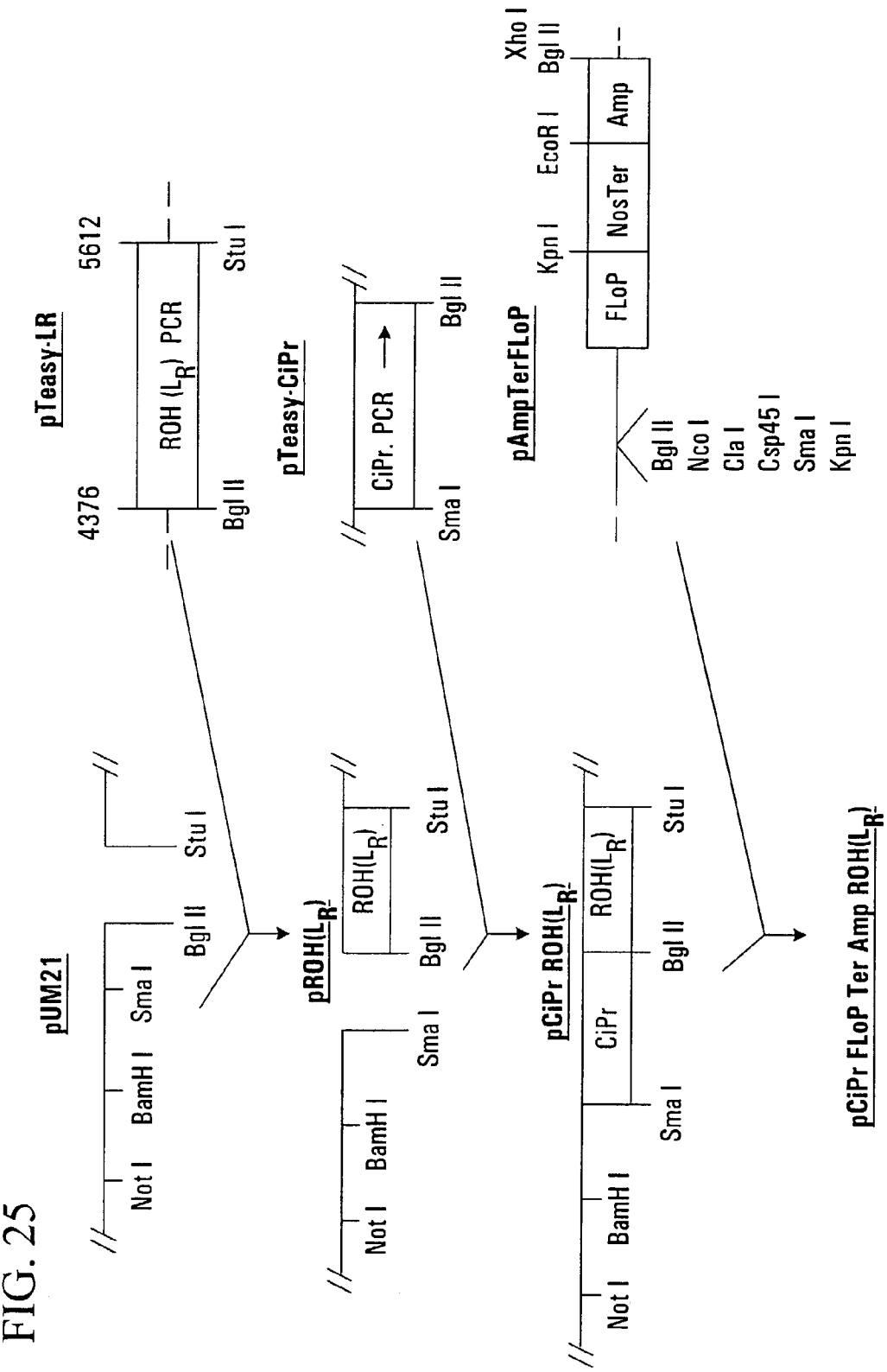
FIG. 25 illustrates the steps used to construct one of the intermediate vectors used for the modification of the left border region of the T-DNA of the C58 Ti-plasmid.

Another series of intermediate plasmids were constructed as outlined in FIG. 25. In this series of steps, pUM21 was used to clone the right-hand side of the region of homology from the Left Border region (ROH($L_R$)) following PCR amplification using primers Seq ID Nos. 23 & 24. The resultant plasmid was called pROH($L_R$). To this plasmid was added the cold-inducible promoter from Brassica (Seq ID No 9) following PCR amplification using primers Seq ID Nos. 27 & 28. The resultant plasmid was called pCiPrROH ($L_R$). To this plasmid was added a Bgl II fragment from pAmpTerFLoP (FIG. 23) to derive pCiPrFLoPTerAmpROH ($L_R$).

Figure 26:
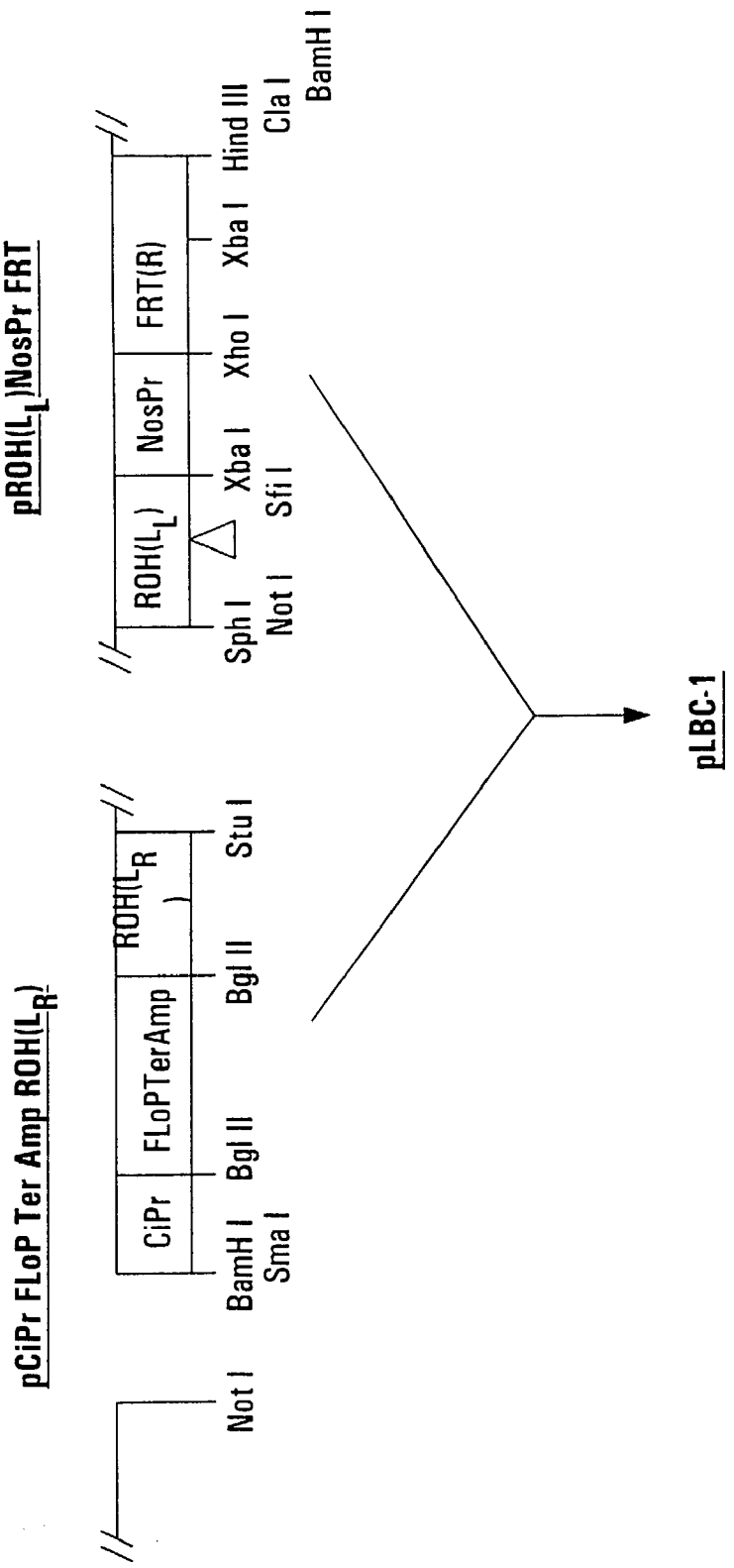
FIG. 26 illustrates the steps used to construct one of the intermediate vectors used for the modification of the left border region of the T-DNA of the C58 Ti-plasmid (final derivation of pLBC-1).
Figure 27:
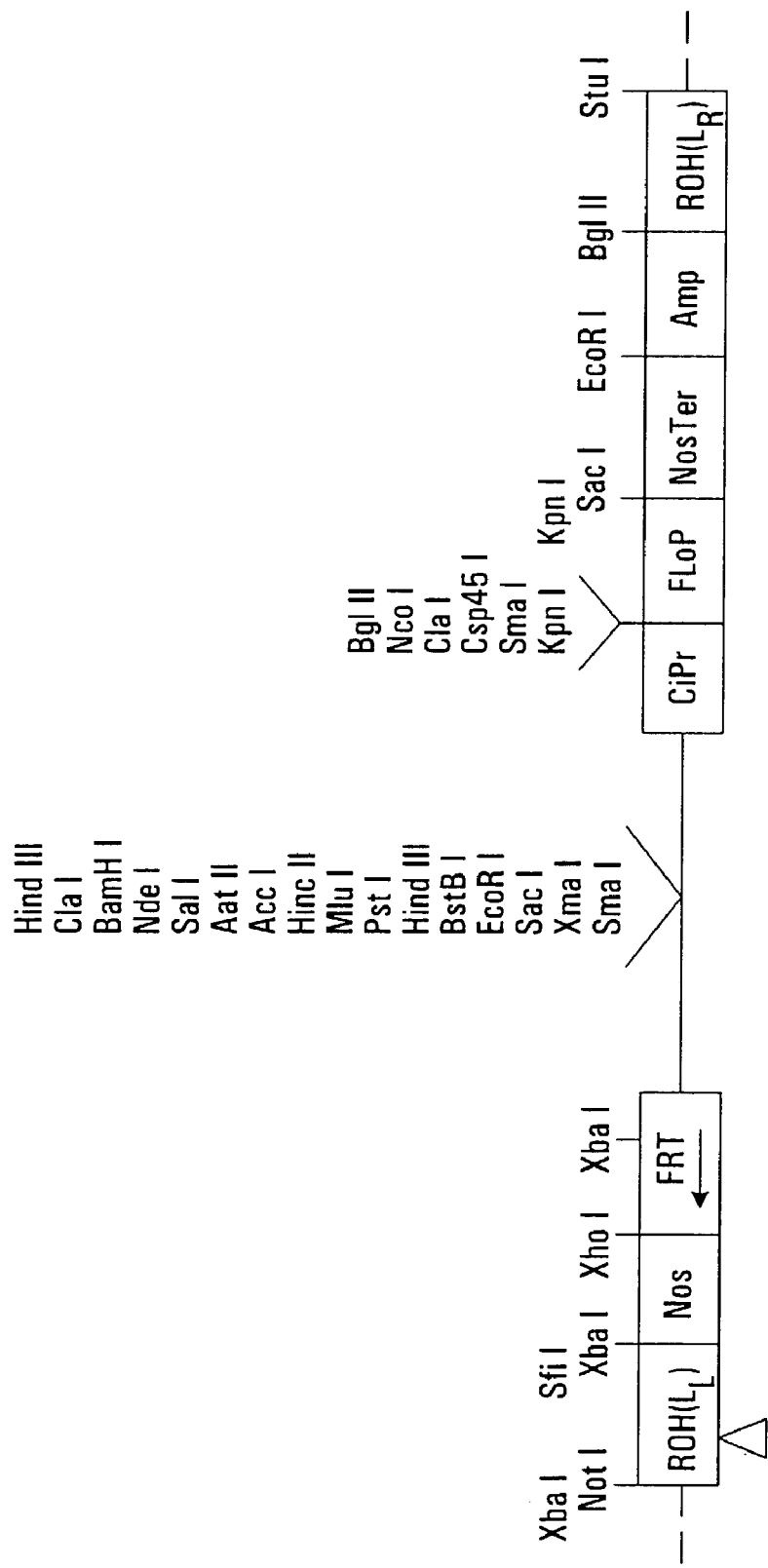
FIG. 27 depicts a detailed restriction map of the homologous recombination plasmid pLBC-1 designed for the insertion of a recombinase sequence into the Left border region of the T-DNA of the C58 nopaline Ti-plasmid. The plasmid contains, two flanking regions of homology and located between those regions is a recombinase recognition site (FRT) as well as a cold-inducible promoter (CiPr) controlling the expression of a FLP recombinase gene modified to contain a plant intron (FLoP) with a nos terminator (NosTer) linked to an ampicillin resistance gene for selection of the homologous recombination event.

This plasmid, pCiPrFLoPTerAmpROH($L_R$) was digested with Not I and Bam HI and the Not I-Bam HI fragment from pROH($L_L$)NosPrFRT was added to derive pLBC-1. This is shown in FIG. 26. The vector pLBC-1 contains: a region of homology with the left border region of the Ti-plasmid, a plant expressible promoter, a recombinase recognition sequence, a multiple cloning site, an inducible promoter, a modified FLP recombinase gene containing a plant intron, a polyadenylation signal, an ampicillin resistance gene and a region of homology with the left border region of the C-58 Ti-plasmid. The restriction map of pLBC-1 is shown in FIG. 27.

EXAMPLE 5

This example illustrates the introduction of the plasmid pLBC-1 into C58 RBC-1 *Agrobacterium*.

In this example, the pLBC-1 vector as used to insert the second recombinase site and associated DNA components into the pTi-C58 RBC-1 Ti-plasmid of the strain C58 RBC-1 by a combination of triparental mating and homologous recombination as described in example 2. In this example, pLBC-1 in the *E. coli* strain DH5FT was combined with *Agrobacterium* C58 RBC-1 and a *E. coli* helper strain HB101 carrying the wide host range plasmid pRK 2013. Cells are plated on minimal media and the *Agrobacterium* is selected for resistance to the antibiotics carbenicillin and rifampicin and sensitivity to kanamycin.

*Agrobacterium* cells resistant to the antibiotic are selected and the integrity of the inserted DNA at the left border region is confirmed by PCR and restriction digest analysis. The resultant vector comprises a wild-type C-58 Ti-plasmid modified to contain a DNA sequence recognized by a site-specific recombinase at both the right border and left border of the T-DNA, (and optionally a marker coding region). The plasmid further comprises a recombinase gene, under the control of a plant promoter inducible by cold treatment. The vector further contains a promoterless GUS-NPTII gene which contains at the 5' end a FRT site, and a nos promoter at the left border region, bounded at the 3' end by a FRT site, such that successful excision of the oncogenic region will eliminate the oncogenic effect and lead to the joining of the nos promoter and the GUS-NPTII gene, thus conferring a visible phenotype on the transformed cell. The modified Ti-plasmid is referred to as pTi-C58 CIMB (Cold Inducible Modified Borders).

EXAMPLE 6

This example illustrates the construction of a second vector for the introduction of a recombinase site in the Left border region of the Ti-plasmid from the wild-type C-58 nopaline *Agrobacterium*.

It is clear that the control of the expression of the recombinase enzyme contained within the modified Ti-plasmid can be by many different means. In the previous examples, a cold inducible promoter was employed. In this example, an inducible promoter system based on the tet repressor is employed within the pLBC-1 vector. The vector containing this alternative gene control system is called pLBC-2. In this example, the construction of this second vector to introduce the second recombinase recognition site into a C-58 Ti-plasmid (pTi-C58 RBC-1) modified to contain, at the right border regions, DNA sequences recognized by a site-specific recombinase. Said second vector pLBC-2 differs from the first vector described (pLBC-1) in the type of inducible promoter used to control the expression of the recombinase gene.

Figure 16A:
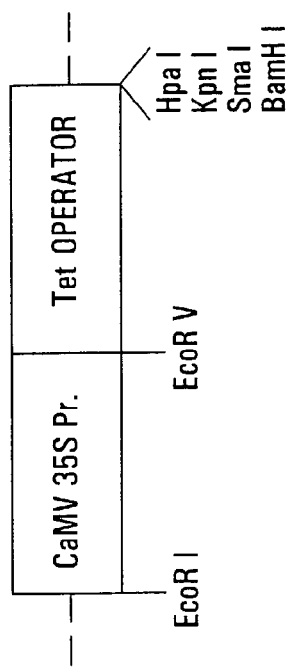
FIGS. 16A–16B provide restriction maps and a representation of the tet repressor/operator DNA sequences used to construct the modified Ti-plasmids.
Figure 16B:
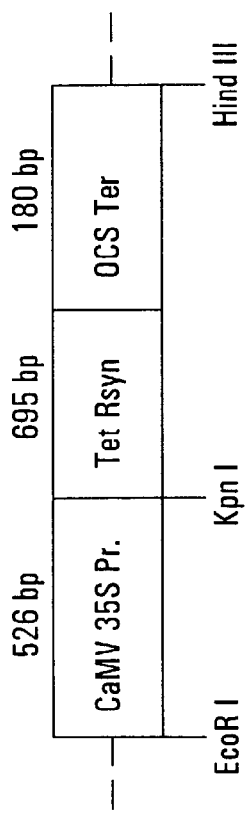
Figure 18B:
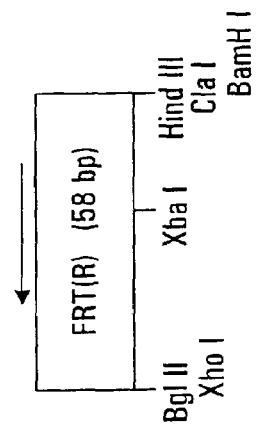
FIGS. 18A–18B provide restriction maps and a representation of the FRT recombinase recognition DNA sequences used to construct the modified Ti-plasmids.
Figure 19:
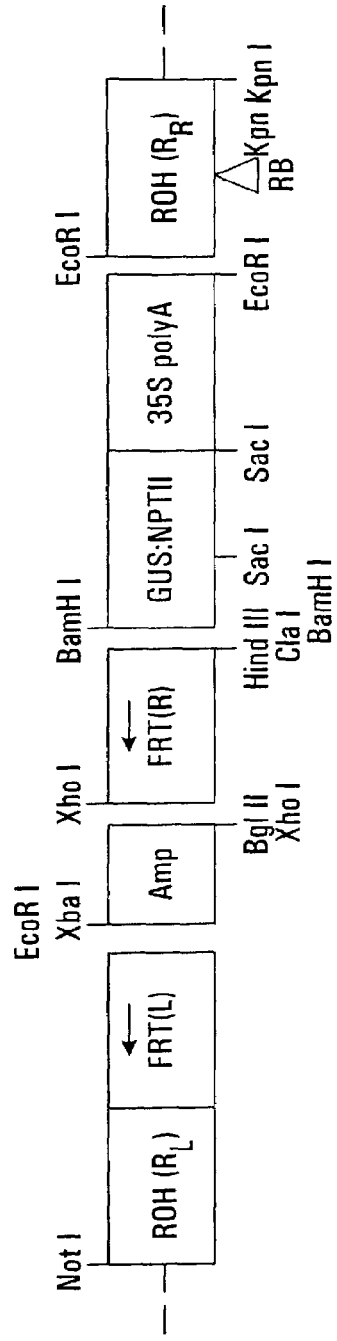
FIG. 19 provides a simplified restriction map and a representation of the components used to derive the homologous recombination plasmid pRBC-1 for insertion of a recombinase sequence into the Right border region of the T-DNA of the C58 nopaline Ti-plasmid.
Figure 18A:
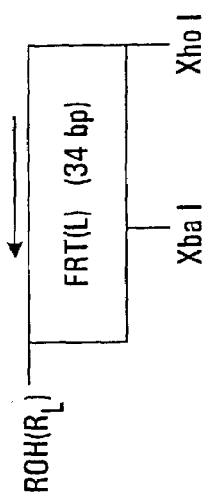
Figure 35:
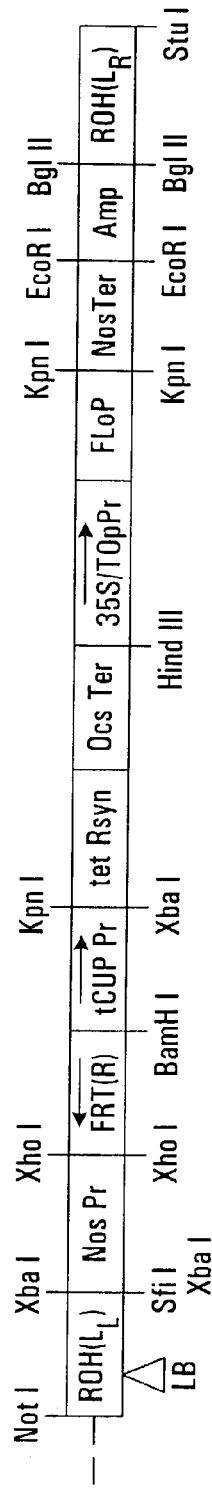
FIG. 35 depicts a simplified restriction map and representation of the components used to derive the homologous recombination plasmid pLBC-2 for insertion of a recombinase sequence into the Left border region of the T-DNA of the C58 nopaline Ti-plasmid. This plasmid comprises the tet repressor/operator system for the control of recombinase expression.

To modify the Ti-plasmid, a vector was constructed for the homologous recombination with the pTi-C58 RBC-1 Ti-plasmid. A number of cloning steps were employed. The steps are outlined in FIGS. 36–37. These steps involved the assembly of various DNA components as follows:

In the assembly of the DNA components detailed herein, the pLBC-2 "shuttle vector" as is used to introduce the specific DNA sequence (FRT) recognized by the recombinase into the modified Ti-plasmid pTiC58 RBC-1 as described previously. The shuttle vector is called pLBC-2 and comprises: a region of homology with the left border region of the Ti-plasmid (ROH($L_L$)) (Seq ID No. 1), a plant expressible promoter (Nos) (Seq ID No. 7), a recombinase recognition sequence (FRT), a multiple cloning site, an inducible promoter system, the tet promoter operator system as shown in FIG. 16 and modified to contain the tCUP promoter (Foster et al, Plant Mol Biol 41: 45–55, 1999), a modified FLP recombinase gene containing a plant intron (FLoP), a polyadenylation signal (NosTer), an ampicillin resistance gene (Amp) (Seq ID No. 11), and a region of homology with the right hand-side of the left border region of the C-58 plasmid (ROH($L_R$)) (Seq ID No. 2). The arrangement of these components in pLBC-2 are shown in FIG. 35.

The construction of pLBC-2 follows a parallel path to the construction outlined for pLBC-1, the primary difference between pLBC-1 and pLBC-2 is the inducible promoter system utilized to control the expression of the recombinase gene.

In pLBC-1 a cold-inducible promoter is used to control the expression of the recombinase gene, in pLBC-2 the tet repressor/operator system is used. The tet repressor/operator system has been used in plant cells and typically comprises the modification of a plant promoter to contain a DNA sequence capable of being recognized by the tet repressor protein, in this case 3 copies of the operator sequence are inserted into the 35S promoter as described by Gatz and Quail (Proc. Natl. Acad. Sci. USA 85: 1394–1397, 1988) to result in a 35S promoter capable of being repressed by the presence of a tet repressor.

The expression of the tet repressor is controlled by another plant promoter, in the present case the constitutive "tCUP" promoter is used. Typically the 35S promoter is used, however since both the repressor and operator sequences would have been in the same vector and both comprise the 35S, another constitutive promoter was employed to eliminate the possibility for re-arrangements and duplications due to the presence of two identical sequences on the same vector.

Thus, the tet repressor system employed in the present invention relies on the constitutive expression of the tet repressor from the "tCUP" promoter to produce repressor molecules capable of repressing gene expression from the 35S promoter modified to contain the tet operator and controlling the expression of the FLP recombinase. The tet repressor has been modified to more closely conform to plant codon usage and contains a nuclear localization signal. This modified tet repressor, referred to as Tet Rsyn, is designed for expression in plant cells. The DNA sequence is shown in Seq ID No. 31. Accordingly the expression of the FLP recombinase is permanently shut off under this arrangement of DNA components. However, the tet repression can be relieved by the presence of tetracycline, which binds to the tet repressor and causes it to dissociate from the tet operator. In this fashion, expression of the FLP recombinase can be induced by culturing in the presence of tetracycline.

Figure 36:
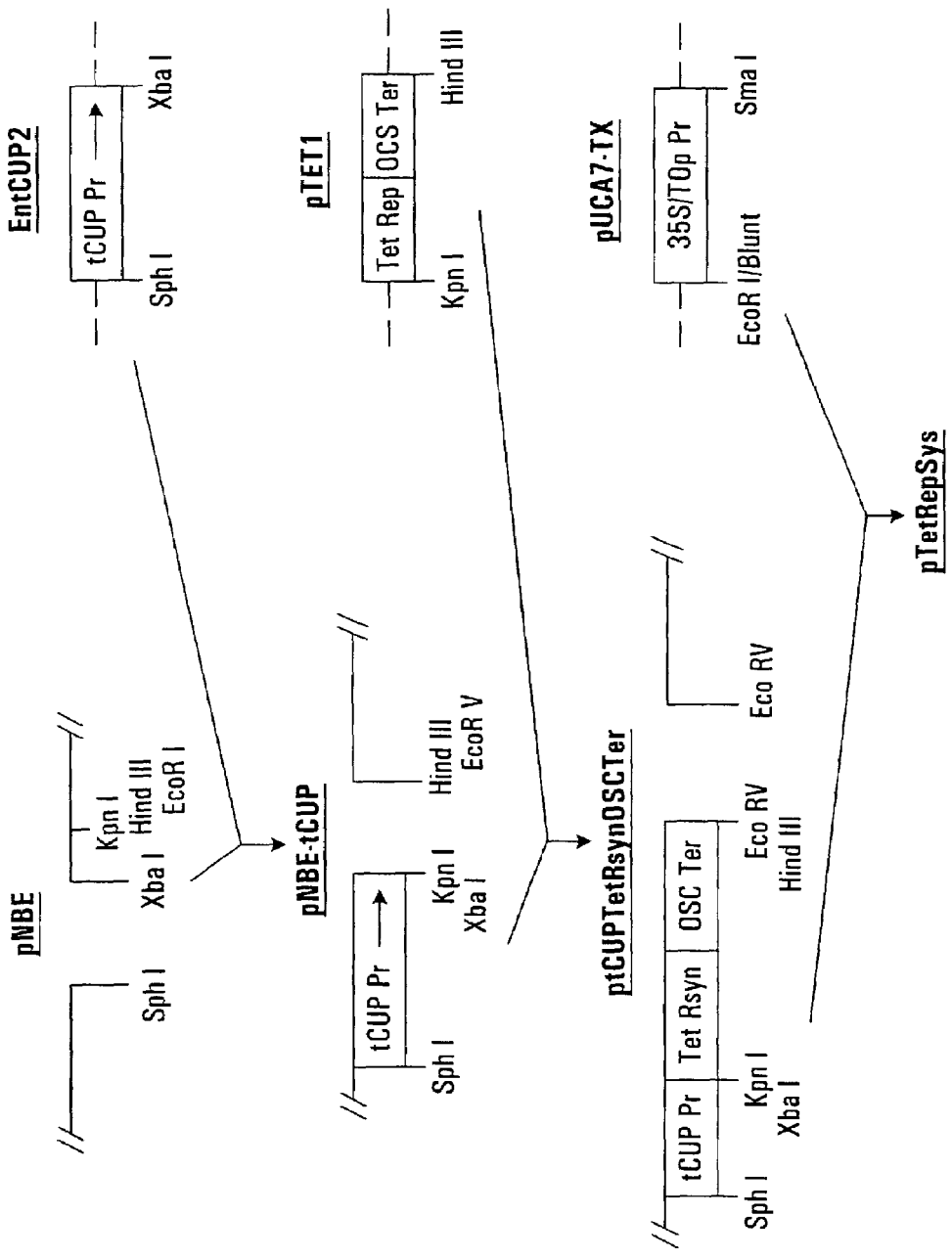
FIG. 36 illustrates the steps used to construct the plasmid encoding the tet repressor system, pTetRepSys.

The construction of pLBC-2 comprised the following steps: The vector pNBE was used to clone a Sph I-Xba I fragment of the tCUP promoter to produce the vector pNBE-tCUP. To this vector was added the pTET2 construct which comprises the modified coding sequence for the tet repressor and the octopine synthase terminator (OCS ter). The resultant plasmid was called ptCUPTetRsynOCSTer. To this construct was added the modified 35S promoter containing the tet operator sequences as found in the plasmid pUCA7-TX The sequence of the modified 35S promoter can be found in Gatz et al., Mol Gen Genet 227:229–237, 1991). The resultant plasmid was called pTetRepSys. These steps are shown in FIG. 36.

Figure 37:
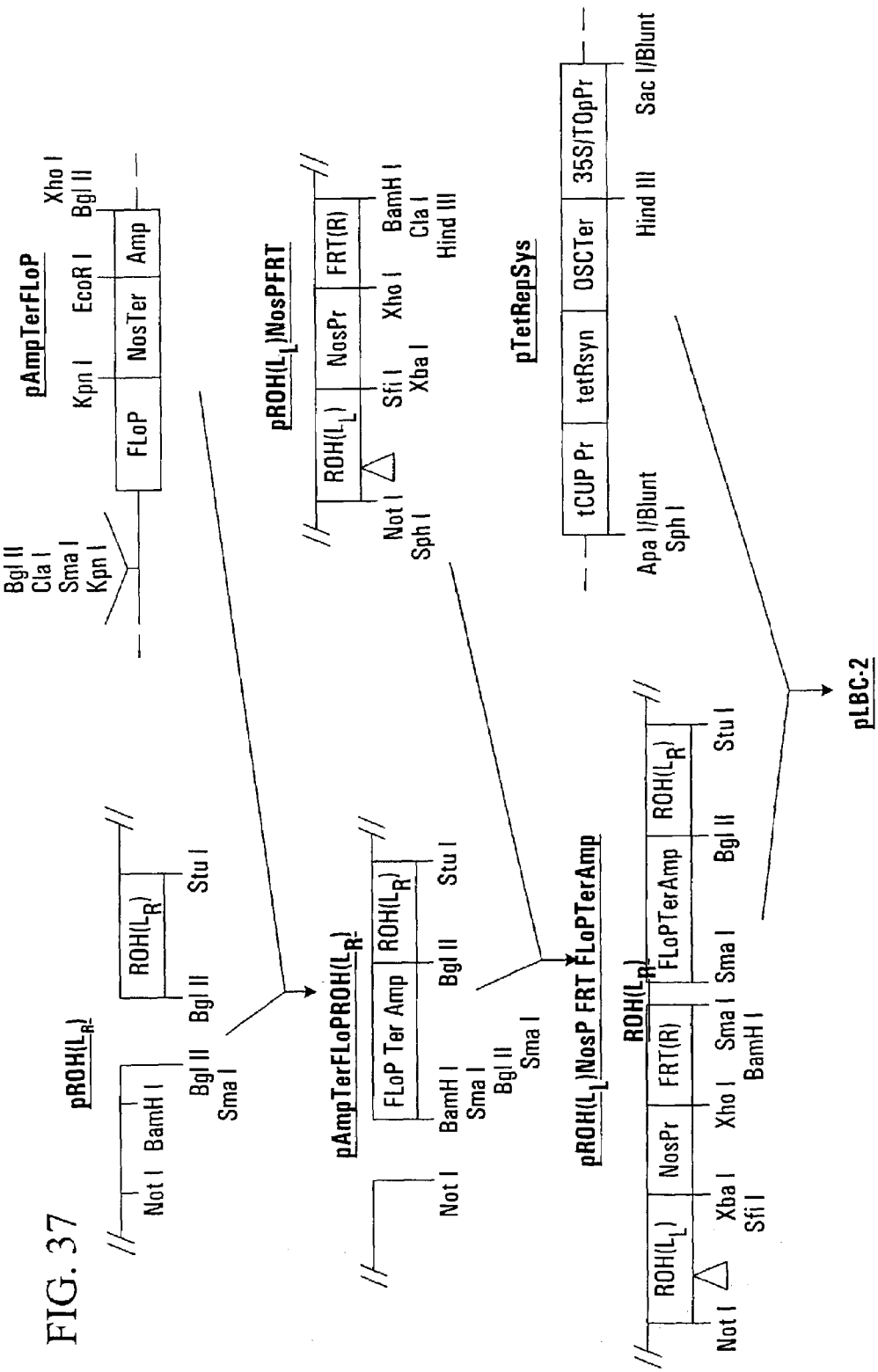
FIG. 37 illustrates construction of the vector pLBC-2. Details of the steps employed to produce a homologous recombination vector for insertion of DNA into the Left Border region of the T-DNA of the C58 Ti-plasmid.
Figure 38:
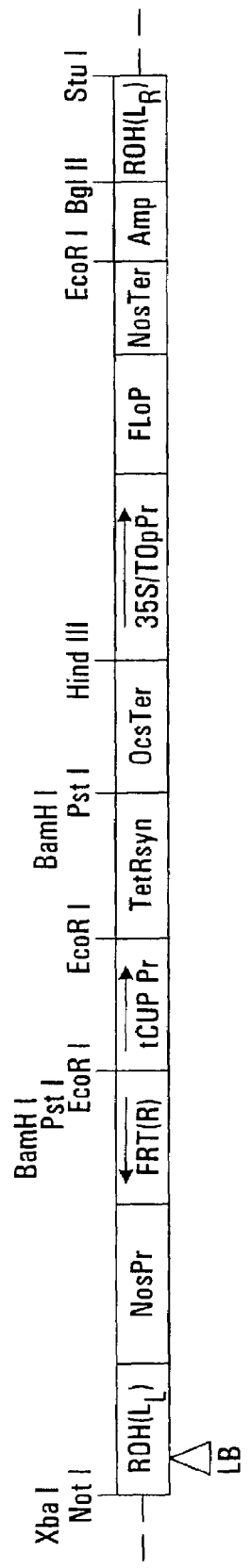
FIG. 38 depicts a detailed restriction map of the homologous recombination plasmid pLBC-2 designed for the insertion of a recombinase sequence into the Left border region of the T-DNA of the C58 nopaline Ti-plasmid. The plasmid contains, two flanking regions of homology and located between those regions is a recombinase recognition site (FRT) as well as the tet repressor/operator system controlling the expression of a FLP recombinase gene modified to contain a plant intron (FloP) with a nos terminator (NosTer) linked to an ampicillin resistance gene for selection of the homologous recombination event.
Figure 39:
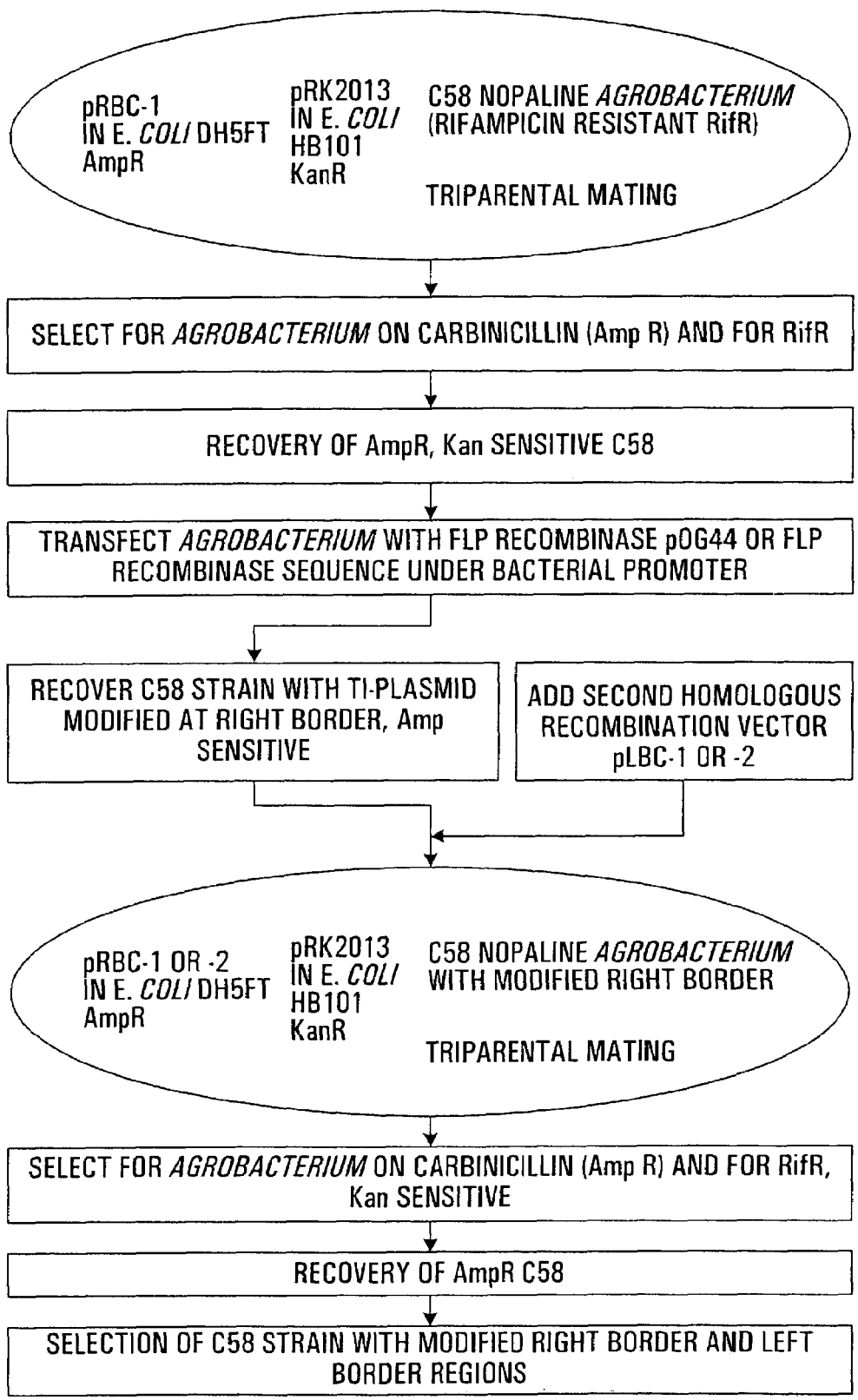
FIG. 39 illustrates the steps used to introduce the vectors pRBC-1, pLBC-1 and pLBC-2 into the C58 *Agrobacterium* and recovery of the modified Ti-plasmid.

The next steps in the assembly of pLBC-2 utilized a series of components used to derive pLBC-1 as described in example 3. The assembly of these components is shown in FIG. 37. The plasmid PROH($L_R$) was combined with pAmpTerFLoP to derive pAmpTerFLoPROH($L_R$) which was then combined with PROH($L_L$) NosFRT to derive PROH($L_L$)NosPFRTFLoPTerAmpROH($L_R$). This plasmid was then combined with the tet repressor system contained in the plasmid pTetRepSys as shown in FIG. 37 to derive pLBC-2. The final restriction map of pLBC-2 is as shown in FIG. 38.

EXAMPLE 7

This example illustrates the introduction of the plasmid pLBC-2 into C58 RBC-1 *Agrobacterium*.

The pLBC-2 vector was used to insert the second recombinase site and associated DNA components into the pTi-C58 RBC-1 Ti-plasmid of the strain C58 RBC-1 by a combination of triparental mating and homologous recombination as described in example 2. The resultant *Agrobacterium* strain is selected for resistance to carbenicillin and rifampicin, as well as sensitivity to kanamycin and the structure of the Ti-plasmid verified. The resultant plasmid is called pTi-C58 TIMB (Tet Inducible Modified Borders).

EXAMPLE 8

This example illustrates transformation of plant cells with pTi-C58 CIMB.

The modified C-58 CIMB Ti-plasmid is verified for function by inoculation on plant explants and observation of crown gall formation. The cold-inducible promoter is inactive at normal temperatures (e.g., 10–20° C.), but highly active at 4° C. Upon induction of the recombinase activity, by culturing tumor tissue at 4° C. overnight, excision of the region contained between the two flanking recombinase sequences occurs, leading to transgenic plant cells comprising the T-DNA border flanking the recombinase recognition DNA sequence. These plant cells now have an active GUS-NPTII fusion protein and the number of transformed cells are scored by staining for GUS activity or selection on kanamycin.

EXAMPLE 9

This example illustrates transformation of plant cells with pTi-C58 TIMB.

The modified C-58 TIMB Ti-plasmid is verified for function by inoculation on plant explants and observation of crown gall formation. Upon induction of the recombinase activity, by culturing crown gall tissue in the presence of 10 uM tetracycline, excision of the region contained between the two flanking recombinase sequences occurs, leading to transgenic plant cells comprising the T-DNA border flanking the recombinase recognition DNA sequence. These plant cells now have an active GUS-NPTII fusion protein and the number of transformed cells are scored by staining for GUS activity or selection on kanamycin.

All publications mentioned in this specification are indicative of the level of skill in the art to which this invention pertains. To the extent they are consistent herewith, all publications mentioned in this specification are herein Incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

The invention claimed is:

1. A method for preparing a transformed plant, comprising:
   (a) introducing into plant cells a construct comprising, in the 5' to 3' direction: a right *Agrobacterium* T-DNA border sequence; a T-DNA oncogenic region of an *Agrobacterium* Ti-plasmid, said T-DNA oncogenic region comprising the full complement of oncogenes found in wild-type *Agrobacterium* T-DNA; a left *Agrobacterium* T-DNA border sequence; and first and second recombinase recognition sites intermediate to said right and left T-DNA border sequences; said construct further comprising a recombinase coding sequence encoding a recombinase that recognizes said first and second recombinase recognition sites, said recombinase coding sequence being under the control of an inducible promoter; to obtain transformed cells comprising said construct; the presence of said T-DNA oncogenic region in said transformed cells resulting in tumor formation;

(b) culturing said transformed cells under conditions that are insufficient for the growth of untransformed cells and that are sufficient for said transformed cells to form tumor tissue, whereby transformed cells are selected; and (c) negating the effect of said T-DNA oncogenic region in said transformed cells by excising at least a portion of said T-DNA oncogenic region with said recombinase; and regenerating morphologically normal transformed plants from said transformed cells.

2. The method according to claim 1, wherein at least one of said first and second recombinase recognition sites is within said T-DNA oncogenic region.

3. The method according to claim 1, wherein neither of said first and second recombinase recognition sites is within said T-DNA oncogenic region.

4. The method according to claim 1, wherein said construct further comprises a novel trait coding sequence located either 5' to said first recombinase recognition site or 3' to said second recombinase recognition site, the expression of said novel coding sequence in a plant conferring a novel trait on said plant.

5. The method according to claim 1 wherein said recombinase coding sequence includes a plant intron.

6. The method according to claim 1 wherein said recombinase is selected from the group consisting of FLP recombinase, Cre recombinase, and R recombinase.

7. The method according to claim 1, wherein said plant cells are dicot cells.

8. The method according to claim 7, wherein said plant cells are cells of a member of the family Malvaceae, Linaceae, Compositae, Solanacae, Fabaceae, Euphorbiaceae, Oleaceae, or Brassicaceae.

9. The method according to claim 7, wherein said plant cells are cells of a member of the genus *Brassica*.

10. The method according to claim 7, wherein said plant cells are cells of broccoli, cabbage, cauliflower, kale, Chinese kale, collard, kohlrabi, Chinese cabbage, pak choi, or turnip.

11. The method according to claim 1, wherein said construct is introduced into said plant cell by *Agrobacterium*-mediated transformation.

* * * * *

SEQUENCE LISTING

```
<160> NUMBER OF SEQ ID NOS: 31

<210> SEQ ID NO 1
<211> LENGTH: 1189
<212> TYPE: DNA
<213> ORGANISM: Agrobacterium tumefaciens
<220> FEATURE:
<221> NAME/KEY: misc_feature
<222> LOCATION: (1)..(1189)
<223> OTHER INFORMATION: Left part of left region of homology
      GenBank Accession No. AJ237588 (3056-4244)

<400> SEQUENCE: 1
ccgctggcga agtggtatat ctcgatgttc atcgcatcga ggtcggcctg gcgggcaata     60
gcggcagggt cgatcagccg ggaatgcatc aggccgacag tcggaacttc gggtccccga    120
cctgtaccat tcggtgagca atggagaggg gagttgatat cgtcaaccgt tcacttctaa    180
agaaatagcg ccactcagct tcctcagcgg ctttatccag cgatttccta ttatgtcggc    240
atagttctca agatcgacag cctgtcacgg ttaagcgaga aatgaataag aaggctgata    300
attcggatct ctgcgaggga gatgatattt gatcacaggc aggaacgctc tgtcatcgtt    360
acaatcaaca tgctaccctc cgcgagatca tccgtgtttc aaacccggca gcttggttgc    420
cgttcttccg aatagcatcg gtaacatgag caaagtctgc cgccttacaa cggctctccc    480
gctgacgccg tcccggactg atgggctgcc tgtatcgagt ggtgattttg tgccgagctg    540
ccggtcgggg agctgttggc tggctggtgg caggatatat tgtggtgtaa acaaattgac    600
gcttagacaa cttaataaca cattgcggac gttttttaatg tactgaattc acatccgttt    660
gatacttgtc taaaattggc tgatttcgag tgcatctatg cataaaaaca atctaatgac    720
aattattacc aagcatcaat gagatgatgt gtgtgtctat gtgtaaatat agcgcggagt    780
cattacagtt ataattattt tacgagttat ttaaagttat aaatacattt atataccaag    840
atatatagac tattataaaa tatgaaactt atataagtaa ttcaatattg cagaggatag    900
atagataaca taaattgctt cctatgtctg atgtacagga ttctataata atatcacggt    960
acagattttc catcttgctc tataacgtcg agatgggggc agtggtgatc aaccctgcgg   1020
ggaacgcctt tgttacgcca ttcccagaat gacatctcat cctcagatcg gtctgatata   1080
acccagtcgg caatcgctgc tgcattgccg ggtattccat agccacggcg aatgtacttt   1140
cgttcatctg tctcgcgtgg catcggtctc cctgtcctga tgttaattg                1189

<210> SEQ ID NO 2
<211> LENGTH: 1237
<212> TYPE: DNA
<213> ORGANISM: Agrobacterium tumefaciens
<220> FEATURE:
<221> NAME/KEY: misc_feature
```

<222> LOCATION: (1)..(1237)
<223> OTHER INFORMATION: Right part of left region of homology
      GenBank Accession No. AJ237588 (4376-5612)

<400> SEQUENCE: 2

| | | | | |
|---|---|---|---|---|
| gcggcgtaat | ctgcgttgaa | ggctctaacg | atttccggtt | tgtcacagag | gcccagctgc | 60 |
| tcaggtttta | ccctggccat | cacaatgtga | actgcgacca | ctctcatcgg | ctgcctgagc | 120 |
| atcgaatcga | tccagatttt | gccgccttca | taaaggtcct | cgacggcgat | gtcgctaaga | 180 |
| tcgatcagtt | ttgccaacct | cggaagttct | tgaggaaaaa | tcaccggcat | gagcgcgacg | 240 |
| gtttccctcc | aatcaggctc | agggctaacc | tgtttgaccg | cgtcaaagaa | cgcttcgccg | 300 |
| ctggagtact | cgaaggtgta | aaagagaagg | accacacgct | gacggtattt | cggacggcgg | 360 |
| cttagccaag | cagtgataat | gtgggcttca | agtcgcgac | catctaaaaa | gaaggttgcg | 420 |
| cccggattga | cgtcgaaaac | cttatccaaa | agaggctcaa | gaaaagggat | gatgtcgttt | 480 |
| gttacggtgt | atgattctgt | gatctcacca | tttgaaacct | ctcgaatgat | caccggtata | 540 |
| ttcttaacat | ctgctgaatg | gagttctcgg | atcagtctat | ccggtaacgt | ggaaatccgc | 600 |
| caggtattga | agtcgtgaga | cacaacgggc | aaattgtcag | aagttagtgt | cgtatccaat | 660 |
| tcagaaagat | ttcgccgttc | catccctccg | agggcagtca | gtaatgaggt | ttcggtacac | 720 |
| tcctgtacgc | ccttccccaa | gttgtacatg | ccccggtgtt | ctatgacttg | aaaggcgttc | 780 |
| aagaaggtgt | ggtaccgaat | gacgagcaag | cacctcgtct | gaagttacgc | ctgctgggag | 840 |
| atcccactgg | atttcccacc | tgggccatcc | cgtacccttc | actgggaagg | gtttgcgctg | 900 |
| acagagtacc | tgaaaaaaac | cggttaaaaa | ctcggaatga | accggaaatc | aaaagaaaga | 960 |
| aaaagatgaa | cctacatcca | tatttcgaga | aaagcgtgtg | ttcgaaacgt | cggttcgggc | 1020 |
| tagagcagga | gggtaccgaa | tgatcgcagc | cgcacagaaa | gagcgcggtt | tagtttgtta | 1080 |
| tagcaagcgc | tacacaggtc | gtttgcccag | tttaaatgta | taagacaaga | ctgccagctg | 1140 |
| gaagttgagg | aatagcgtct | taaattcatc | atgatataag | catgcgcggg | aatcccgctc | 1200 |
| cttttttgaa | agctaaggtc | agtgtcggcc | gcaatgg | | | 1237 |

<210> SEQ ID NO 3
<211> LENGTH: 1594
<212> TYPE: DNA
<213> ORGANISM: Agrobacterium tumefaciens
<220> FEATURE:
<221> NAME/KEY: misc_feature
<222> LOCATION: (1)..(1594)
<223> OTHER INFORMATION: right part of right region of homology
      GenBank Accession No. AJ237588 and AB016260 (28376-29970)

<400> SEQUENCE: 3

| | | | | | | |
|---|---|---|---|---|---|---|
| tccgctcatg | atcagattgt | cgtttcccgc | cttcggttta | aactatcagt | gtttgacagg | 60 |
| atatattggc | gggtaaacct | aagagaaaag | agcgtttatt | agaataatcg | gatatttaaa | 120 |
| agggcgtgaa | aaggtttatc | cgttcgtcca | tttgtatgtg | catgccaacc | acagggttcc | 180 |
| cctcgggagt | gcttggcatt | ccgtgcgata | atgacttctg | ttcaaccacc | caaacgtcgg | 240 |
| aaagcctgac | gacggagcag | cattccaaaa | agatcccttg | gctcgtctgg | gtcggctaga | 300 |
| aggtcgagtg | ggctgctgtg | gcttgatccc | tcaacgcggt | cgcggacgta | gcgcagcgcc | 360 |
| gaaaaatcct | cgatcgcaaa | tccgacgctg | tcgaaaagcg | tgatctgctt | gtcgctcttt | 420 |
| cggccgacgt | cctggccagt | catcacgcgc | caaagttccg | tcacaggatg | atctggcgcg | 480 |
| agttgctgga | tctcgccttc | aatccgggtc | tgtggcggga | actccacgaa | aatatccgaa | 540 |

-continued

```
cgcagcaaga tatcgcggtg catctcggtc ttgcctgggc agtcgccgcc gacgccgttg      600
atgtggacgc cgggcccgat catattgtcg ctcaggatcg tggcgttgtg cttgtcggcc      660
gttgctgtcg taatgatatc ggcaccttcg accgcctgtt ccgcagaggt gcaggcctcg      720
atctgaaacc cgaaccgctg gagattgcgg gagcagcgag cagtagcctc ggggtcgatg      780
tcgtaaagtc gtatccgatc gacgccgatc agccgcttga aggccaaagc ctggaactca      840 cttttgggcac cgttgccgat cagcgccatc gtgcgcgaat ctttacgggc cagatacttt      900
gccgcgatcg cggaggtcgc ggccgttcgc aaggccgtca ggattgtcat ttccgacagc      960
agcagcggat agccgctatc gacatcggag agcacgccga acgcggtcac cgtctgccgt     1020
cccgacttcg tgttttcgg atgcccgttg acgtatttga agccatagag cgttccgtcg     1080
ctcgtcggca tgagttcaat cacgccgtcc cgcgaatgcg aggcgatgcg tggaatcttg     1140
tcgaagctct cccagcgccg gaaatcttct tcaatgtagc cggccagttg aacaaggaag     1200
ttctcgatcc cggtgctgac cgccagatcc atcatgtttt caacactgat gaacggaacg     1260
atgttgaggt tggcaagtgc aggcatcttt tggcccccctt tattggtttg ataggctgcc     1320
ggacgagccc cgatcacacg ggttcggccg tgatcgcgta cccggtaact acccgtttct     1380
tgagcgtggg cagatccagc gggccgaggt ctggaagcag gtcgttttct tcggagaagt     1440
cgcgtccgta gcaggcgctt aagatccgca cgccgctttc atgcaagggt gcagacaggc     1500
cggctgcttt tgccagatgc agggtgggga tcagaccaaa gggaacgtcc tcgagcacgt     1560
agcgcgtatc aaggctcttc gggcctgccg gatc                                 1594
```

<210> SEQ ID NO 4
<211> LENGTH: 1394
<212> TYPE: DNA
<213> ORGANISM: Agrobacterium tumefaciens
<220> FEATURE:
<221> NAME/KEY: misc_feature
<222> LOCATION: (1)..(1394)
<223> OTHER INFORMATION: left part of right region of homology
      GenBank Accession No. AJ237588 (24917-26307)

<400> SEQUENCE: 4

```
tcaatcgaac ccggaaaaac cagagataat tatattctta tttaagagta atgatgttaa       60
gttgttcatt gaattaattc aaatcacaat ctcacggtat ggttagaaat agacgcccgt      120
tagattgtta ccaggctaga ttcgaaaact gcaagcaaca cccatgatgg gtggtgatgt      180
tttccgaaaa aattccctgc ttttagacga agataacgta tttatttcgt tactagatga      240
cattggaaac acgaaaaata acagagatcc aaagcacact ctcatagatt atgcgacttt      300
attaggagtc gtcgacggga attatgccga aagatggcat gaccctaaag caatgatcgg      360
ataattgata aggtttcctg tctgagaatc tcttgtttcg cctccgccag tctcgtcttc      420
atcgtccatc tcatcgtcgt catcttctcc ttcctcagtg taatttcctc cccgggcata      480
aaaaccgtag ttttcattgt tgattacgtc ggtcccgaac cgaacaaagc agttgcttgg      540
catgatcgct aaaagaact gatttgtatg cgggccttga tagtagtgga cgaggccacc      600
ttgatcgcac cttcctgca taactcgatt cagcctgcgt gcatccatca accacggcgg      660
tattgcagtt gccattattc cggagttaga ggagttggac ggtaggtgtc gacgcaaggc      720
gcattggcgt gcaatatctt cacgaaggta aacatagacc agctcttgtc gagtgaggat      780
gtactcatca tcaaactcac caagtctaat cgcggaaggc tgaaagtata cagtttcggg      840
aagtaaagct ccgaaatccg ttctcgcctg ttccaagcga ctctgcatct cgccggtgcg      900
```

```
caggataagc gtcaaatctc gaacctgcca attagctacc gtcatcgcag ttttggatgt    960
actacaaaat acctgccgct ggtaaatctg agccgttggt tcttatattg acctgggaag   1020
cccattgacg ccattggtga ccgtttgatg ccgtgtgaaa acacgacaga ttgatagcat   1080
tgattagcgc ttttgaattt tcagctgctg agccccgaca cgctgtcgca aaagtcgccc   1140
taggcccgcc taacgatttg tcgtcacttg gcaaggtgtg tgacctgcac ctcatttgtg   1200
ggctcgcatg caccgaaaaa ctgctgcata attgaccgca agcttcatca acgcaagaca   1260
tgcgcacgac cgtctgacag gagaggaatt ccgacgagc acagaaagga cttgctcttg    1320
gaggtaggcc tatttctcag gcacatgtat caagtgttcg acgtgggtt ttcgatggtg    1380 tatcagccgc cgcc                                                     1394

<210> SEQ ID NO 5
<211> LENGTH: 1272
<212> TYPE: DNA
<213> ORGANISM: Saccharomyces
<220> FEATURE:
<221> NAME/KEY: misc_feature
<222> LOCATION: (1)..(1272)
<223> OTHER INFORMATION: FLP ORF on pOG44

<400> SEQUENCE: 5
atgccacaat tgatatatt atgtaaaaca ccacctaagg tgcttgttcg tcagtttgtg     60
gaaaggtttg aaagaccttc aggtgagaaa atagcattat gtgctgctga actaacctat   120
ttatgttgga tgattacaca taacggaaca gcaatcaaga gagccacatt catgagctat   180
aatactatca taagcaattc gctgagtttg gatattgtca acaagtcact gcagtttaaa   240
tacaagacgc aaaaagcaac aattctggaa gcctcattaa agaaattgat tcctgcttgg   300
gaatttacaa ttattcctta ctatggacaa aaacatcaat ctgatatcac tgatattgta   360
agtagtttgc aattacagtt cgaatcatcg gaagaagcag ataagggaaa tagccacagt   420
aaaaaaatgc ttaaagcact tctaagtgag ggtgaaagca tctgggagat cactgagaaa   480
atactaaatt cgtttgagta tacttcgaga tttacaaaaa caaaaacttt ataccaattc   540
ctcttcctag ctactttcat caattgtgga agattcagcg atattaagaa cgttgatccg   600
aaatcattta aattagtcca aaataagtat ctgggagtaa taatccagtg tttagtgaca   660
gagacaaaga caagcgttag taggcacata tacttcttta gcgcaagggg taggatcgat   720
ccacttgtat atttggatga atttttgagg aattctgaac cagtcctaaa acgagtaaat   780
aggaccggca attcttcaag caacaagcag gaataccaat tattaaaaga taacttagtc   840
agatcgtaca caaagctttt gaagaaaaat gcgccttatt caatctttgc tataaaaaat   900
ggcccaaaat ctcacattgg aagacatttg atgacctcat ttctttcaat gaagggccta   960
acggagttga ctaatgttgt gggaaattgg agcgataagc gtgcttctgc cgtggccagg   1020
acaacgtata ctcatcagat aacagcaata cctgatcact acttcgcact agtttctcgg   1080
tactatgcat atgatccaat atcaaggaa atgatagcat tgaaggatga gactaatcca   1140
attgaggagt ggcagcatat agaacagcta aagggtagtg ctgaaggaag catacgatac   1200
cccgcatgga atgggataat atcacaggag gtactagact accttttcatc ctacataaat   1260 agacgcatat aa                                                      1272

<210> SEQ ID NO 6
<211> LENGTH: 359
<212> TYPE: DNA
<213> ORGANISM: Artificial Sequence
```

```
<220> FEATURE:
<223> OTHER INFORMATION: Synthetic DNA fragment with Arbidopsis
      eEF-1beta intron

<400> SEQUENCE: 6
ctgcagagat ctggatccac catgccacag ttcgatatcc tctgcaagac cccacctaag    60
gttagaatct gttttctaac agctgtctac tttatctatc ttttttttgaa acaatagtag   120 taaccattac tttcttctgt ctctctatgt atatatgttt ataggtgctt gttaggcagt   180
tcgtggagag gtttgaaaga ccttctggtg agaagatcgc attgtgtgct gctgagctta   240
cttacttgtg ctggatgatt acccacaacg gaacagcaat caaaagagcc accttcatgt   300
cttacaacac tatcattagc aattccctca gcttcgacat cgtcaacaag tctctgcag    359

<210> SEQ ID NO 7
<211> LENGTH: 328
<212> TYPE: DNA
<213> ORGANISM: Agrobacterium tumefaciens
<220> FEATURE:
<221> NAME/KEY: misc_feature
<222> LOCATION: (1)..(328)
<223> OTHER INFORMATION: Nos promoter Bin19,
      GenBank Accession No. U09365 (8955-9282)

<400> SEQUENCE: 7
atccggtgca gattatttgg attgagagtg aatatgagac tctaattgga taccgagggg    60
aatttatgga acgtcagtgg agcatttttg acaagaaata tttgctagct gatagtgacc   120
ttaggcgact tttgaacgcg caataatggt ttctgacgta tgtgcttagc tcattaaact   180
ccagaaaccc gcggctgagt ggctccttca acgttgcggt tctgtcagtt ccaaacgtaa   240
aacggcttgt cccgcgtcat cggcgggggt cataacgtga ctcccttaat tctccgctca   300
tgatcagatt gtcgtttccc gccttcag                                      328

<210> SEQ ID NO 8
<211> LENGTH: 2654
<212> TYPE: DNA
<213> ORGANISM: Artificial Sequence
<220> FEATURE:
<223> OTHER INFORMATION: GUS:NPTII fusion: GenBank Accession No. M26402

<400> SEQUENCE: 8
atgttacgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa   120
gaaagccggg caattgctgt gccaggcagt tttaacgatc agttcgccga tgcagatatt   180
cgtaattatg cgggcaacgt ctggtatcag cgcgaagtct ttataccgaa aggttgggca   240
ggccagcgta tcgtgctgcg tttcgatgcg gtcactcatt acggcaaagt gtgggtcaat   300
aatcaggaag tgatggagca tcagggcggc tatacgccat ttgaagccga tgtcacgccg   360
tatgttattg ccgggaaaag tgtacgtatc accgtttgtg tgaacaacga actgaactgg   420
cagactatcc cgccgggaat ggtgattacc gacgaaaacg gcaagaaaaa gcagtcttac   480
ttccatgatt tctttaacta tgccggaatc catcgcagcg taatgctcta caccacgccg   540
aacacctggg tggacgatat caccgtggtg acgcatgtcg cgcaagactg taaccacgcg   600
tctgttgact ggcaggtggt ggccaatggt gatgtcagcg ttgaactgcg tgatgcggat   660
caacaggtgg ttgcaactgg acaaggcact agcgggactt tgcaagtggt gaatccgcac   720
ctctggcaac cgggtgaagg ttatctctat gaactgtgcg tcacagccaa aagccagaca   780
```

-continued

```
gagtgtgata tctacccgct tcgcgtcggc atccggtcag tggcagtgaa gggccaacag      840
ttcctgatta accacaaacc gttctacttt actggctttg gtcgtcatga agatgcggac      900
ttacgtggca aaggattcga taacgtgctg atggtgcacg accacgcatt aatggactgg      960
attggggcca actcctaccg tacctcgcat taccettacg ctgaagagat gctcgactgg     1020
gcagatgaac atggcatcgt ggtgattgat gaaactgctg ctgtcggctt taacctctct     1080
ttaggcattg gtttcgaagc gggcaacaag ccgaaagaac tgtacagcga agaggcagtc     1140
aacggggaaa ctcagcaagc gcacttacag gcgattaaag agctgatagc gcgtgacaaa     1200
aaccacccaa gcgtggtgat gtggagtatt gccaacgaac cggatacccg tccgcaagtg     1260
cacgggaata tttcgccact ggcggaagca acgcgtaaac tcgacccgac gcgtccgatc     1320
acctgcgtca atgtaatgtt ctgcgacgct cacaccgata ccatcagcga tctctttgat     1380
gtgctgtgcc tgaaccgtta ttacggatgg tatgtccaaa gcggcgattt ggaaacggca     1440
gagaaggtac tggaaaaaga acttctggcc tggcaggaga aactgcatca gccgattatc     1500
atcaccgaat acggcgtgga tacgttagcc gggctgcact caatgtacac cgacatgtgg     1560
agtgaagagt atcagtgtgc atggctggat atgtatcacc gcgtctttga tcgcgtcagc     1620
gccgtcgtcg gtgaacaggt atggaatttc gccgattttg cgacctcgca aggcatattg     1680
cgcgttggcg gtaacaagaa agggatcttc actcgcgacc gcaaaccgaa gtcggcggct     1740
tttctgctgc aaaaacgctg gactggcatg aacttcggtg aaaaaccgcg cagggaggca     1800
aacaatgaat caacaactct cctggcgcac catcgtcggc tacagcctcg ggaattgcta     1860
ccgagctcga gcttggatgg attgcacgca ggttctccgg ccgcttgggt ggagaggcta     1920
ttcggctatg actgggcaca acagacaatc ggctgctctg atgccgccgt gttccggctg     1980
tcagcgcagg ggcgcccggt tctttttgtc aagaccgacc tgtccggtgc cctgaatgaa     2040
ctgcaggacg aggcagcgcg gctatcgtgg ctggccacga cgggcgttcc ttgcgcagct     2100
gtgctcgacg ttgtcactga agcgggaagg gactggctgc tattgggcga agtgccgggg     2160
caggatctcc tgtcatctca ccttgctcct gccgagaaag tatccatcat ggctgatgca     2220
atgcggcggc tgcatacgct tgatccggct acctgcccat tcgaccacca agcgaaacat     2280
cgcatcgagc gagcacgtac tcggatggaa gccggtcttg tcgatcagga tgatctggac     2340
gaagagcatc aggggctcgc gccagccgaa ctgttcgcca ggctcaaggc gcgcatgccc     2400
gacggcgagg atctcgtcgt gacccatggc gatgcctgct tgccgaatat catggtggaa     2460
aatggccgct tttctggatt catcgactgt ggccggctgg gtgtggcgga ccgctatcag     2520
gacatagcgt tggctacccg tgatattgct gaagagcttg gcggcgaatg ggctgaccgc     2580
ttcctcgtgc tttacggtat cccgctcccg attcgcagcg catcgccttc tatcgccttc     2640
ttgacgagtt cttc                                                        2654
```

<210> SEQ ID NO 9
<211> LENGTH: 1186
<212> TYPE: DNA
<213> ORGANISM: Brassica napus
<220> FEATURE:
<221> NAME/KEY: misc_feature
<222> LOCATION: (1)..(1186)
<223> OTHER INFORMATION: Cold Inducible promoter. GenBank Accession No. U14665 (148-1333)

<400> SEQUENCE: 9

```
atcttgcggt cgacattgaa agattcatgt tctaagattt agttacaatt tgatgaacaa       60
```

```
ataagttaag tttaaagttt tttgcgatac aaatgttagg ttgaaagttt aaaatgctaa      120 tgaaaactt taaagtttta agtgttaat gaataccact ttgagggttt ttatgcaatt       180
ttatgcaatt ttctcaattt ttaagttacc catctaggta caaaaatatt ttaaaccatt    240
ttgtccaaga ttcgtgattt ctttgagccg gtcctgatgg cttggctctg atgtaccaga   300
aaatcgatgc accacgctaa tattttgtac aaaaaaaaat caatgttata tagcattcaa    360
tgaaacgatt taacccattt tgtaaatcct aattgaaaaa actaatcttg cacccggtga   420
ccgttatata tgcaactttg tgaaaatatg gtttgtagtt tttatttaag ctattacacc   480
atgtctgttt agaagttcct agtggatagg atatctctga aagtgacgtt aattaattgt   540
tatttatgta atggtatgcc ttttaaaatt acaaaaattg gttttagtag ataaatatgt    600
tgtttaaagg aaaataaata taatggtatg cctttttgaaa ttacaaatat gacgttaatt   660
aattgttatt tatgtaatgg aaccccatga ataccataa accatatatc actctataag    720
tgtgataggc ttgccatcat atacgttata tttttatatc tatattttga aaactttta    780 ggcttgccat catatacgtt tttttttttt ggggtagatt tactaacatg ttggccgacg    840 tatactttg tttttatcac aacaaaggtg gtacacgtga agtaacgata acgacccaca    900
actccgattt ctttgtgttt aattttgcaa aaaataaaag cagaaatgct aacatgtata    960
tcaccacaag ttttgatggc cgacctgttt tttcaatagt taaagaaaat aacatcaatg   1020
cattataaaa aaattctacg atgccacgtg atttggattg cagttggtct agtatctata  1080
aaactatgat actattggag aatagattat tactcatctc actcttgttc ctattaaaac  1140
tcctcctttg atttcttttg ctcgcttttg actctttaaa gagaac                 1186
```

<210> SEQ ID NO 10
<211> LENGTH: 195
<212> TYPE: DNA
<213> ORGANISM: Cauliflower mosaic virus
<220> FEATURE:
<221> NAME/KEY: misc_feature
<222> LOCATION: (1)..(195)
<223> OTHER INFORMATION: 35S polyA: pFF19

<400> SEQUENCE: 10

```
tttctccata ataatgtgtg agtagttccc agataaggga attaggggttc ttatagggtt    60 tcgctcacgt gttgagcata taagaaaccc ttagtatgta tttgtatttg taaaatactt   120
ctatcaataa aatttctaat tcctaaaacc aaaatccagt actaaaatcc agatcaccta  180
aagtccctat agatc                                                   195
```

<210> SEQ ID NO 11
<211> LENGTH: 1086
<212> TYPE: DNA
<213> ORGANISM: Artificial Sequence
<220> FEATURE:
<223> OTHER INFORMATION: Ampicillin resistance gene: pBR322 GenBank
      Accession No. J01749 ( 3265-4350

<400> SEQUENCE: 11

```
gtatatatga gtaaacttgg tctgacagtt accaatgctt aatcagtgag gcacctatct    60
cagcgatctg tctatttcgt tcatccatag ttgcctgact ccccgtcgtg tagataacta   120
cgatacggga gggcttacca tctggcccca gtgctgcaat gataccgcga gacccacgct   180
caccggctcc agatttatca gcaataaacc agccagccgg aagggccgag cgcagaagtg  240
gtcctgcaac tttatccgcc tccatccagt ctattaattg ttgccgggaa gctagagtaa   300
```

```
gtagttcgcc agttaatagt ttgcgcaacg ttgttgccat tgctgcaggc atcgtggtgt      360
cacgctcgtc gtttggtatg gcttcattca gctccggttc ccaacgatca aggcgagtta      420
catgatcccc catgttgtgc aaaaaagcgg ttagctcctt cggtcctccg atcgttgtca      480
gaagtaagtt ggccgcagtg ttatcactca tggttatggc agcactgcat aattctctta      540
ctgtcatgcc atccgtaaga tgcttttctg tgactggtga gtactcaacc aagtcattct      600
gagaatagtg tatgcggcga ccgagttgct cttgcccggc gtcaacacgg ataataccg       660 cgccacatag cagaacttta aaagtgctca tcattggaaa acgttcttcg gggcgaaaac      720
tctcaaggat cttaccgctg ttgagatcca gttcgatgta acccactcgt gcacccaact      780
gatcttcagc atcttttact ttcaccagcg tttctgggtg agcaaaaaca ggaaggcaaa      840
atgccgcaaa aaagggaata agggcgacac ggaaatgttg aatactcata ctcttccttt      900
ttcaatatta ttgaagcatt tatcagggtt attgtctcat gagcggatac atatttgaat      960
gtatttagaa aaataaacaa ataggggttc cgcgcacatt tccccgaaaa gtgccacctg     1020
acgtctaaga aaccattatt atcatgacat taacctataa aaataggcgt atcacgaggc     1080
cctttc                                                                1086

<210> SEQ ID NO 12
<211> LENGTH: 304
<212> TYPE: DNA
<213> ORGANISM: Artificial Sequence
<220> FEATURE:
<223> OTHER INFORMATION: Basis of mobilization ste: pBR322 GenBank
      Accession No. J01749 (2 217-2520

<400> SEQUENCE: 12
gacccagtca cgtagcgata gcggagtgta tactggctta actatgcggc atcagagcag       60
attgtactga gagtgcacca tatgcggtgt gaaataccgc acagatgcgt aaggagaaaa      120
taccgcatca ggcgctcttc cgcttcctcg ctcactgact cgctgcgctc ggtcgttcgg      180
ctgcggcgag cggtatcagc tcactcaaag gcggtaatac ggttatccac agaatcaggg      240
gataacgcag gaaagaacat gtgagcaaaa ggccagcaaa aggccaggaa ccgtaaaaag      300
gccg                                                                   304

<210> SEQ ID NO 13
<211> LENGTH: 36
<212> TYPE: DNA
<213> ORGANISM: Artificial Sequence
<220> FEATURE:
<223> OTHER INFORMATION: Forward PCR primer to amplify Bom site

<400> SEQUENCE: 13
atagaattcc cgcgggaccc agtcacgtag cgatag                                 36

<210> SEQ ID NO 14
<211> LENGTH: 29
<212> TYPE: DNA
<213> ORGANISM: Artificial Sequence
<220> FEATURE:
<223> OTHER INFORMATION: Reverse PCR primer to amplify Bom site

<400> SEQUENCE: 14
ataaagcttc ggccttttta cggttcctg                                         29

<210> SEQ ID NO 15
<211> LENGTH: 27
<212> TYPE: DNA
```

<210> SEQ ID NO 15
<211> LENGTH: 27 (implied)
<212> TYPE: DNA
<213> ORGANISM: Artificial Sequence
<220> FEATURE:
<223> OTHER INFORMATION: Forward PCR primer to amplify Nos promoter

<400> SEQUENCE: 15
atatctagac tgaaggcggg aaacgac                                27

<210> SEQ ID NO 16
<211> LENGTH: 28
<212> TYPE: DNA
<213> ORGANISM: Artificial Sequence
<220> FEATURE:
<223> OTHER INFORMATION: Reverse PCR primer to amplify Nos promoter

<400> SEQUENCE: 16
atactcgaga tccggtgcag attatttg                               28

<210> SEQ ID NO 17
<211> LENGTH: 33
<212> TYPE: DNA
<213> ORGANISM: Artificial Sequence
<220> FEATURE:
<223> OTHER INFORMATION: Forward PCR primer to amplify ROH-RR

<400> SEQUENCE: 17
atagaattct ccgctcatga tcagattgtc gtt                         33

<210> SEQ ID NO 18
<211> LENGTH: 29
<212> TYPE: DNA
<213> ORGANISM: Artificial Sequence
<220> FEATURE:
<223> OTHER INFORMATION: Reverse PCR primer to amplify ROH-RR

<400> SEQUENCE: 18
ataggtaccg atccggcagg cccgaagag                              29

<210> SEQ ID NO 19
<211> LENGTH: 34
<212> TYPE: DNA
<213> ORGANISM: Artificial Sequence
<220> FEATURE:
<223> OTHER INFORMATION: Forward PCR primer to amplify ROH-RL

<400> SEQUENCE: 19
catagcggcc gctcaatcga acccggaaaa acca                        34

<210> SEQ ID NO 20
<211> LENGTH: 63
<212> TYPE: DNA
<213> ORGANISM: Artificial Sequence
<220> FEATURE:
<223> OTHER INFORMATION: Reverse PCR primer to amplify ROH-RL (including
     FRT site)

<400> SEQUENCE: 20
atactcgagg aagttcctat tctctagaaa gtataggaac ttcggcggcg gctgatacac    60
cat                                                                 63

<210> SEQ ID NO 21
<211> LENGTH: 35
<212> TYPE: DNA
<213> ORGANISM: Artificial Sequence
<220> FEATURE:
<223> OTHER INFORMATION: Forward PCR primer to amplify ROH-LL

<400> SEQUENCE: 21
atagcatgcg cggccgcccg ctggcgaagt ggtat                    35

<210> SEQ ID NO 22
<211> LENGTH: 47
<212> TYPE: DNA
<213> ORGANISM: Artificial Sequence
<220> FEATURE:
<223> OTHER INFORMATION: Reverse PCR primer to amplify ROH-LL

<400> SEQUENCE: 22
gtattctaga ggccataatg gcccaattaa catcaggaca gggagac       47

<210> SEQ ID NO 23
<211> LENGTH: 31
<212> TYPE: DNA
<213> ORGANISM: Artificial Sequence
<220> FEATURE:
<223> OTHER INFORMATION: Forward PCR primer to amplify ROH-LR

<400> SEQUENCE: 23
ataagatctg cggcgtaatc tgcgttgaag g                        31

<210> SEQ ID NO 24
<211> LENGTH: 30
<212> TYPE: DNA
<213> ORGANISM: Artificial Sequence
<220> FEATURE:
<223> OTHER INFORMATION: Reverse PCR primer to amplify ROH-LR

<400> SEQUENCE: 24
tataggcctc cattgcggcc gacactgacc                          30

<210> SEQ ID NO 25
<211> LENGTH: 26
<212> TYPE: DNA
<213> ORGANISM: Artificial Sequence
<220> FEATURE:
<223> OTHER INFORMATION: Forward PCR primer to amplify Amp

<400> SEQUENCE: 25
atagaattcg aaagggcctc gtgata                              26

<210> SEQ ID NO 26
<211> LENGTH: 40
<212> TYPE: DNA
<213> ORGANISM: Artificial Sequence
<220> FEATURE:
<223> OTHER INFORMATION: Reverse PCR primer to amplify Amp

<400> SEQUENCE: 26
atactcgaga gatctgtata tatgagtaaa cttggtctga               40

<210> SEQ ID NO 27
<211> LENGTH: 31
<212> TYPE: DNA
<213> ORGANISM: Artificial Sequence
<220> FEATURE:
<223> OTHER INFORMATION: Forward PCR primer to amplify cold inducible
      promoter

<400> SEQUENCE: 27
atacccggga tcttgcggtc gacattgaaa g                        31

<210> SEQ ID NO 28

```
<211> LENGTH: 34
<212> TYPE: DNA
<213> ORGANISM: Artificial Sequence
<220> FEATURE:
<223> OTHER INFORMATION: Reverse PCR primer to amplify cold inducible
      promoter

<400> SEQUENCE: 28 ataagatct gttctcttta aagagtcaaa agcg                              34

<210> SEQ ID NO 29
<211> LENGTH: 58
<212> TYPE: DNA
<213> ORGANISM: Artificial Sequence
<220> FEATURE:
<223> OTHER INFORMATION: Synthetic DNA sequence for FRT(R)

<400> SEQUENCE: 29
gatctctcga ggaagttcct atactttcta gagaatagga acttcaagct tatcgatg    58

<210> SEQ ID NO 30
<211> LENGTH: 58
<212> TYPE: DNA
<213> ORGANISM: Artificial Sequence
<220> FEATURE:
<223> OTHER INFORMATION: Synthetic DNA sequence for FRT(R)

<400> SEQUENCE: 30
gatccatcga taagcttgaa gttcctattc tctagaaagt ataggaactt cctcgaga     58

<210> SEQ ID NO 31
<211> LENGTH: 669
<212> TYPE: DNA
<213> ORGANISM: Artificial Sequence
<220> FEATURE:
<223> OTHER INFORMATION: Synthetic DNA sequence for the tet repressor

<400> SEQUENCE: 31
cgagaaaatg tctagattag ataaaagtaa agtgattaac agcgcattag agctgcttaa    60
tgaggtcgga atcgagggct taacgacccg taaactcgcg cagaagctag gagtagagca   120
gcctacgttg tactggcatg ttaagaacaa gcgggctttg ctcgacgccc tcgcgattga   180
gatgttagac aggcaccata ctcacttctg ccctctcgaa ggggagagct ggcaagattt   240
cctccgtaac aacgctaagt ccttcagatg tgctctccta tcccatcgcg acggagcaaa   300
agttcatctg ggtacacggc ctacagaaa acagtatgag actctcgaaa atcaactggc    360
ctttctgtgc caacagggtt tctcactaga gaatgcgctt tacgcactct cagctgtggg   420
gcattttact cttggttgcg ttttggagga tcaagagcat caagtcgcta aggaagagag   480
ggaaacacct actactgata gtatgccgcc acttcttcga caagccatcg aacttttga    540 tcaccagggt gcagagccag ccttcttgtt cggccttgaa ttgatcatat gcggattgga   600
aaagcagctt aaatgtgaat cggggtctct taagccaaaa aagaagcgta aggtctgact   660
taagtgaat                                                          669
```